US010144927B2

(12) United States Patent
Kampmann et al.

(10) Patent No.: US 10,144,927 B2
(45) Date of Patent: Dec. 4, 2018

(54) METHODS FOR GENOME-WIDE SCREENING AND CONSTRUCTION OF GENETIC INTERACTION MAPS

(71) Applicant: The Regents of the University of California, Oakland, CA (US)

(72) Inventors: Martin Kampmann, San Francisco, CA (US); Michael Bassik, San Francisco, CA (US); Jonathan Weissman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 145 days.

(21) Appl. No.: 14/458,114

(22) Filed: Aug. 12, 2014

(65) Prior Publication Data

US 2015/0072893 A1    Mar. 12, 2015

Related U.S. Application Data

(63) Continuation of application No. PCT/US2013/025215, filed on Feb. 7, 2013.

(60) Provisional application No. 61/598,296, filed on Feb. 13, 2012.

(51) Int. Cl.
| | |
|---|---|
| *C12N 15/10* | (2006.01) |
| *C12N 15/11* | (2006.01) |
| *C12Q 1/68* | (2018.01) |
| *G06F 19/18* | (2011.01) |
| *G01N 33/50* | (2006.01) |
| *C12Q 1/6886* | (2018.01) |

(52) U.S. Cl.
CPC ........ *C12N 15/1075* (2013.01); *C12N 15/111* (2013.01); *C12Q 1/68* (2013.01); *C12Q 1/6886* (2013.01); *G01N 33/502* (2013.01); *G06F 19/18* (2013.01); *C12N 2310/14* (2013.01); *C12N 2310/531* (2013.01); *C12N 2320/12* (2013.01); *C12Q 2600/136* (2013.01); *C12Q 2600/142* (2013.01)

(58) Field of Classification Search
CPC ............ C12N 15/1075; C12N 15/1079; C12N 15/1086; C12N 15/111; C12N 2320/11–2320/13; C12N 15/113; C12N 15/1135–15/1138; C12Q 2600/136
See application file for complete search history.

(56) References Cited

FOREIGN PATENT DOCUMENTS

WO    WO 2010111712 A2 *  9/2010    ......... A01K 67/0271

OTHER PUBLICATIONS

Bassik et al. Rapid creation and quantitative monitoring of high coverage shRNA libraries. Nature Methods, vol. 6, No. 6, pp. 443-447, Jun. 2009, published online May 17, 2009.*
Luo et al. Highly parallel identification of essential genes in cancer cells. Proceedings of the National Academy of Sciences, USA, vol. 105, No. 51, pp. 20380-20385, Dec. 2008, and pp. 1/22-2/22 of Supporting Information.*
Grimm et al. Combinatorial RNAi: A winning strategy for the race against evolving targets? Molecular Therapy, vol. 15, No. 5, pp. 878-888, 2007.*
Zalckvar et al. A systems level strategy for analyzing the cell death network: implication in exploring the apoptosis/autophagy connection. Cell Death and Differentiation, vol. 17, pp. 1244-1253, Dec. 2010, including pp. 1/20-20/20 of Supplementary Information.*
Lambeth et al. A direct comparison of stratetgies for combinatorial RNA interference. BMC Molecular Biology, vol. 11, p. 77, 2010, printed as pp. 1/15-15/15.*
Horn et al. Mapping of signaling networks through synthetic genetic interaction analysis by RNAi. Nature Methods. vol. 8, No. 4, pp. 341-346, pp. 1/3-3/3 of Online Methods, and pp. 1/28-28/28 of Supplementary Figures and Tables, Mar. 6, 2011.*
Kaelin Jr, WG. The concept of synthetic lethality in the context of anticancer therapy. Nature Reviews Cancer, vol. 5, pp. 689-698, Sep. 2005.*
Ketela et al. A comprehensive platform for highly multiplexed mammalian functional genetic screens. BMC Genomics. vol. 12, p. 213, Jan. 1, 2011, printed as pp. 1/13-13/13.*
Kuiken et al. Exploration of synthetic lethal interactions as cancer drug targets. Future Oncology, vol. 6, No. 11, pp. 1789-1802, 2010.*
Sahin et al. Combinatorial RNAi for quantitative protein network analysis. Proceedings of the National Academy of Sciences, USA. vol. 104, No. 16, pp. 6579-6584, Apr. 2007.*
Tedesco et al. Abstract A36: Viability screens in leukemic and breast cancer cells with pooled lentiviral shRNA libraries identify potential therapeutic targets and synerrgistic lethal interactions. Cancer Genomics, vol. 71, Issue 18 Supplement, p. A36, Sep. 15, 2011, printed as pp. 1/2-2/2.*
Rottenberg et al. High sensitivity of BRCA1-deficient mammary tumors to the PARP inhibitor AZD2281 alone and in combination with platinum drugs. Proceedings of the National Academy of Sciences, USA, vol. 105, No. 44, pp. 17079-17084, Nov. 2008.*

(Continued)

*Primary Examiner* — Jennifer Dunston
(74) *Attorney, Agent, or Firm* — Mintz Levin, Cohn, Ferris, Glovsky and Popeo, P.C.

(57) ABSTRACT

The present invention provides methods for conducting screens using nucleic acid elements (e.g., interfering RNAs) to confidently identify hit genetic elements. The present invention further comprises constructing vectors that contain two or more nucleic acid elements to knock down all pairwise combinations of the hit genetic elements identified from the screen. Following quantitation of the single and double-knockdown phenotypes, genetic interactions between all gene pairs can be calculated. Genes can then be clustered according to the similarity of the pattern of their interactions with all of the other genes to obtain a genetic interaction map, which can advantageously be used to predict functional associations between genes and identify drug targets for therapy such as combination cancer therapy.

10 Claims, 51 Drawing Sheets

(56) References Cited

OTHER PUBLICATIONS

Adamson, B. et al. (Feb. 19, 2012). "A genome-wide homologous recombination screen identifies the RNA-binding protein RBMX as a component of the DNA-damage response," *Nat Cell Biol* 14(3):318-328.

Brummelkamp, T.R. et al. (Apr. 2006, e-published Feb. 13, 2006). "An shRNA barcode screen provides insight into cancer cell vulnerability to MDM2 inhibitors," *Nat Chem Biol* 2(4):202-206.

Bushman, F.D. et al. (May 2009, e-published May 29, 2009). "Host cell factors in HIV replication: meta-analysis of genome-wide studies," *PLoS Pathog* 5(5):e1000437.

Collins, S.R. et al. (2006). "A strategy for extracting and analyzing large-scale quantitative epistatic interaction data," *Genome Biol* 7(7):R63.

Collins, S.R. et al. (Oct. 2009). "From information to knowledge: new technologies for defining gene function," *Nat Methods* 6(10):721-723.

Fellmann, C. et al. (Mar. 18, 2011, e-published Feb. 25, 2011). "Functional identification of optimized RNAi triggers using a massively parallel sensor assay," *Mol Cell* 41(6):733-746.

International Search Report dated May 15, 2013, for PCT Application No. PCT/US2013/025215, filed Feb. 7, 2013, 5 pages.

Schultz, N. et al. (Mar. 14, 2011). "Off-target effects dominate a large-scale RNAi screen for modulators of the TGF-β pathway and reveal microRNA regulation of TGFBR2," *Silence* 2:3.

Silva, J.M. et al. (Nov. 2005, e-published Oct. 2, 2005). "Second-generation shRNA libraries covering the mouse and human genomes," *Nat Genet* 37(11):1281-1288.

Storey, J.D. et al. (Aug. 5, 2003, e-published Jul. 25, 2003). "Statistical significance for genomewide studies," *Proc Natl Acad Sci* 100(16):9440-9445.

Written Opinion dated May 15, 2013, for PCT Application No. PCT/US2013/025215, filed Feb. 7, 2013, 6 pages.

Zenders, L. et al. (Nov. 28, 2008, e-published Nov. 13, 2008). "An oncogenomics-based in vivo RNAi screen identifies tumor suppressors in liver cancer," *Cell* 135(5):82-864.

\* cited by examiner

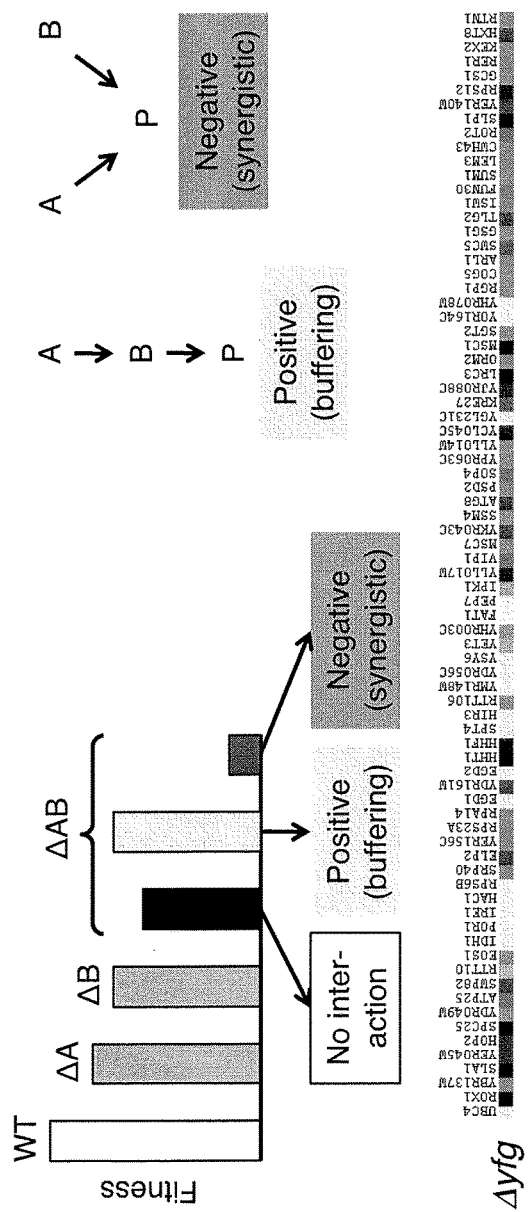

FIG. 18A
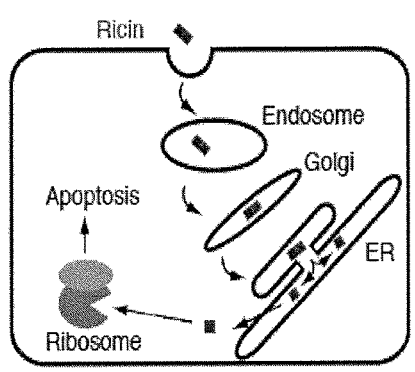
FIG. 18B
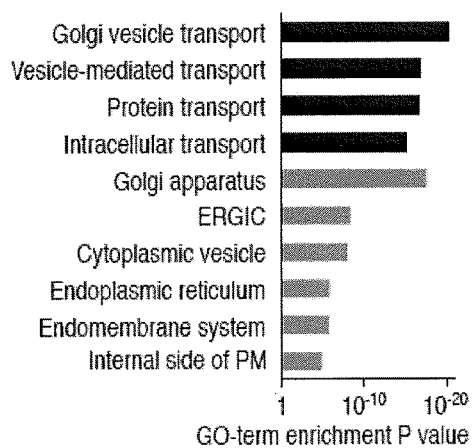
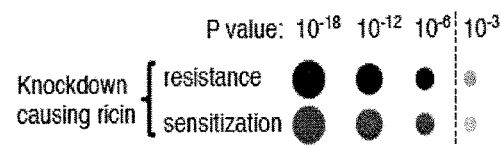
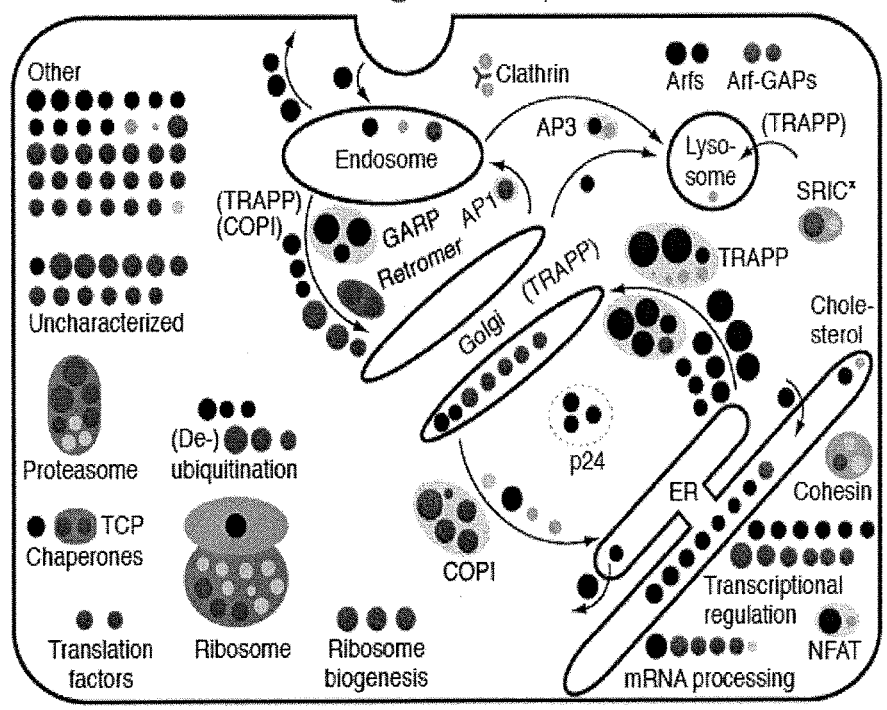
FIG. 18C

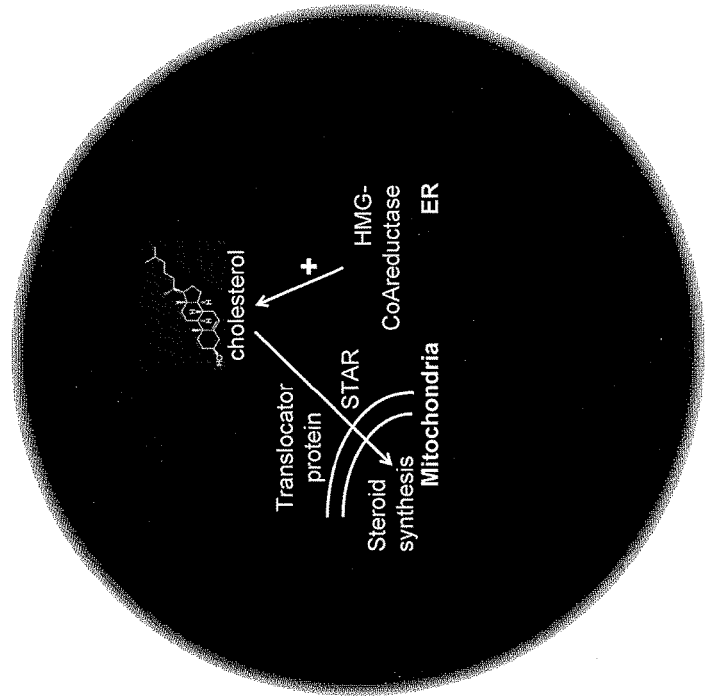
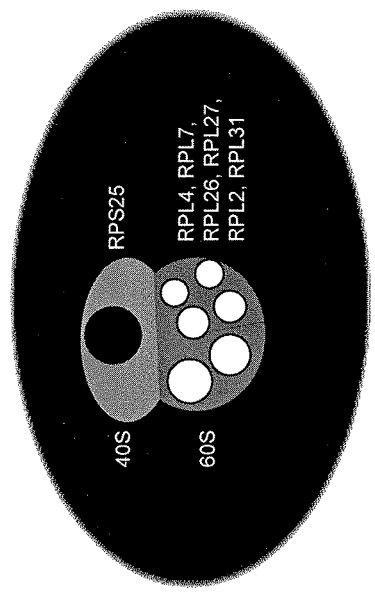
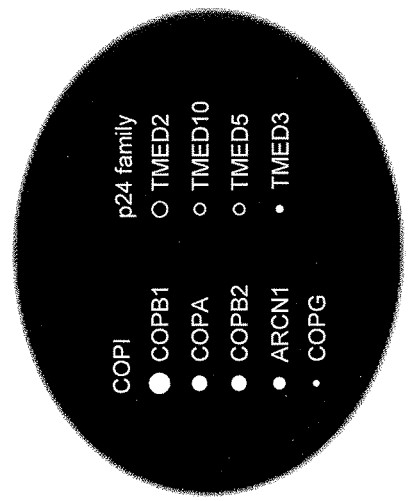

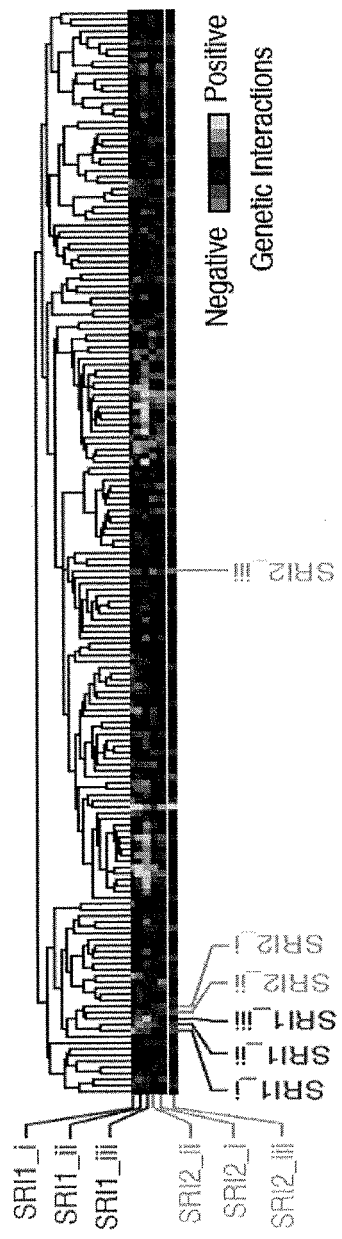
FIG. 23A
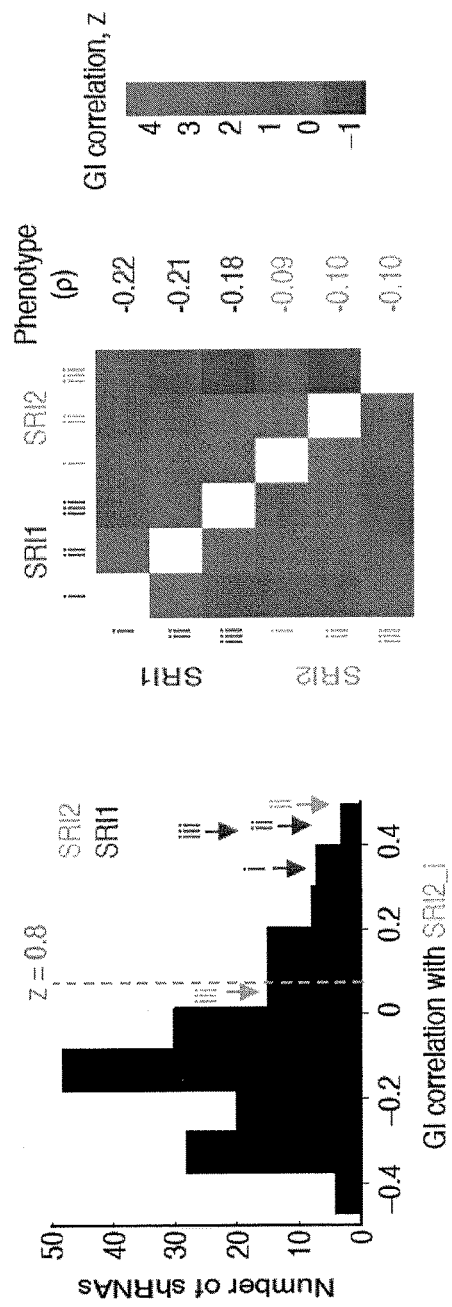
FIG. 23B
FIG. 23C

FIG. 26A
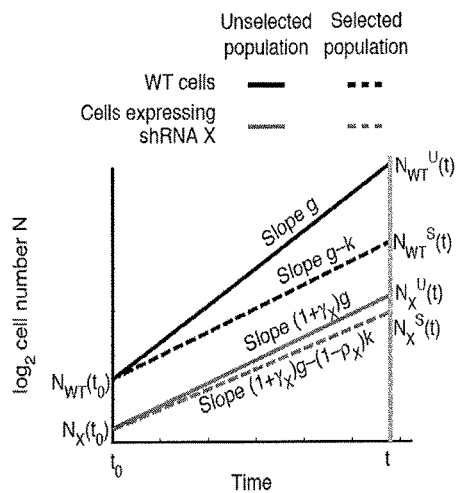
FIG. 26B
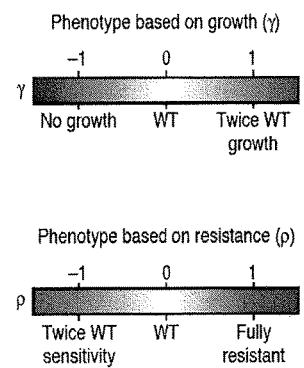
FIG. 26C
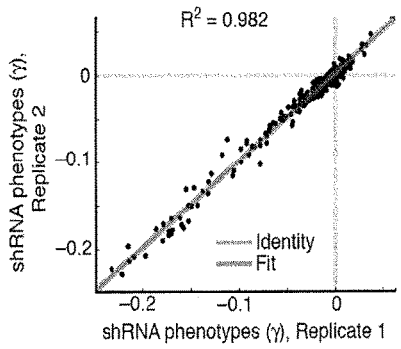
FIG. 26D
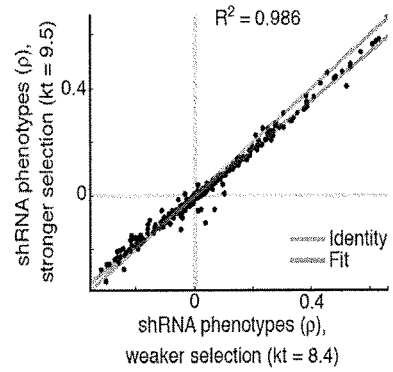
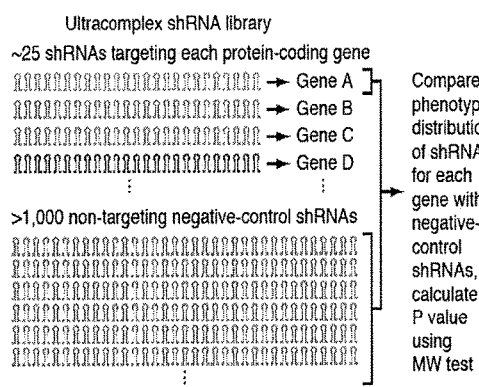
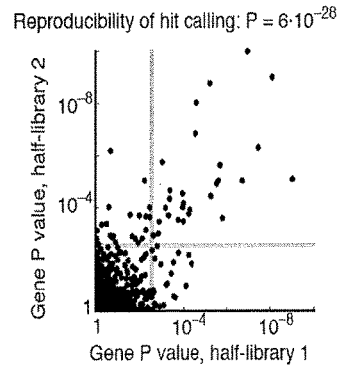
FIG. 26E
FIG. 26F

FIG. 32A
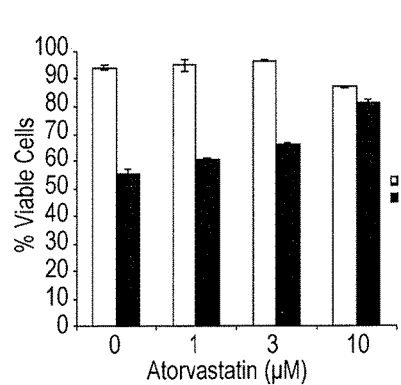
FIG. 32B
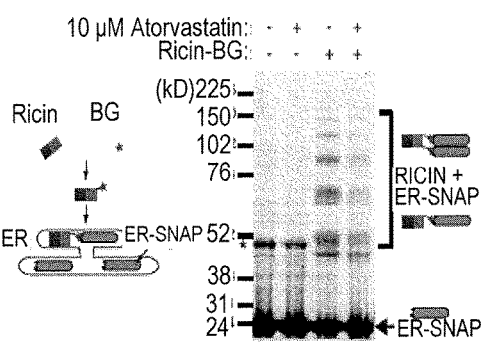
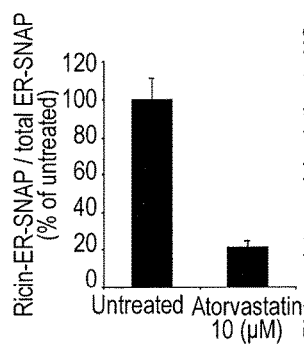
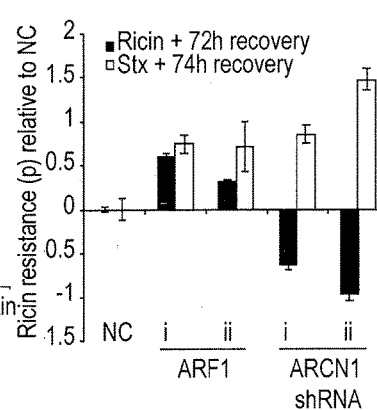
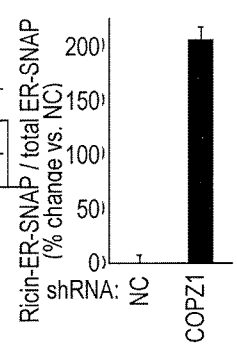
FIG. 32C  FIG. 32D  FIG. 32E

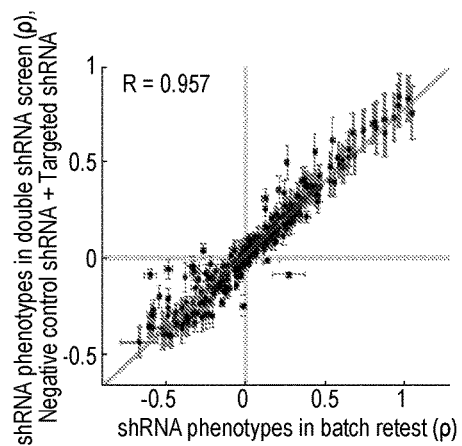
FIG. 33B
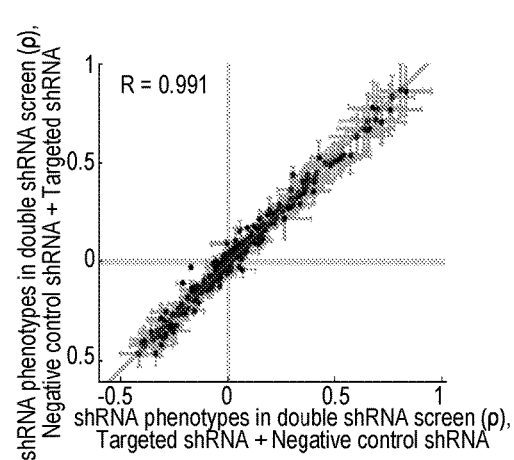
FIG. 33C
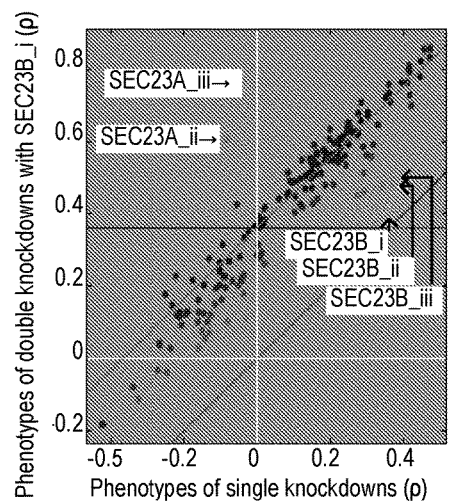
FIG. 33D
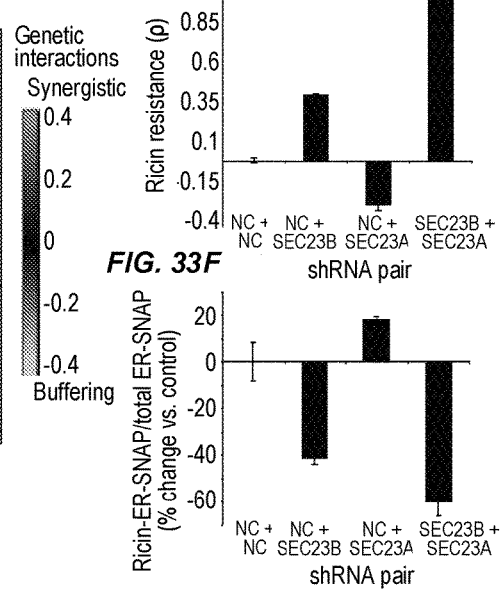
FIG. 33E
FIG. 33F

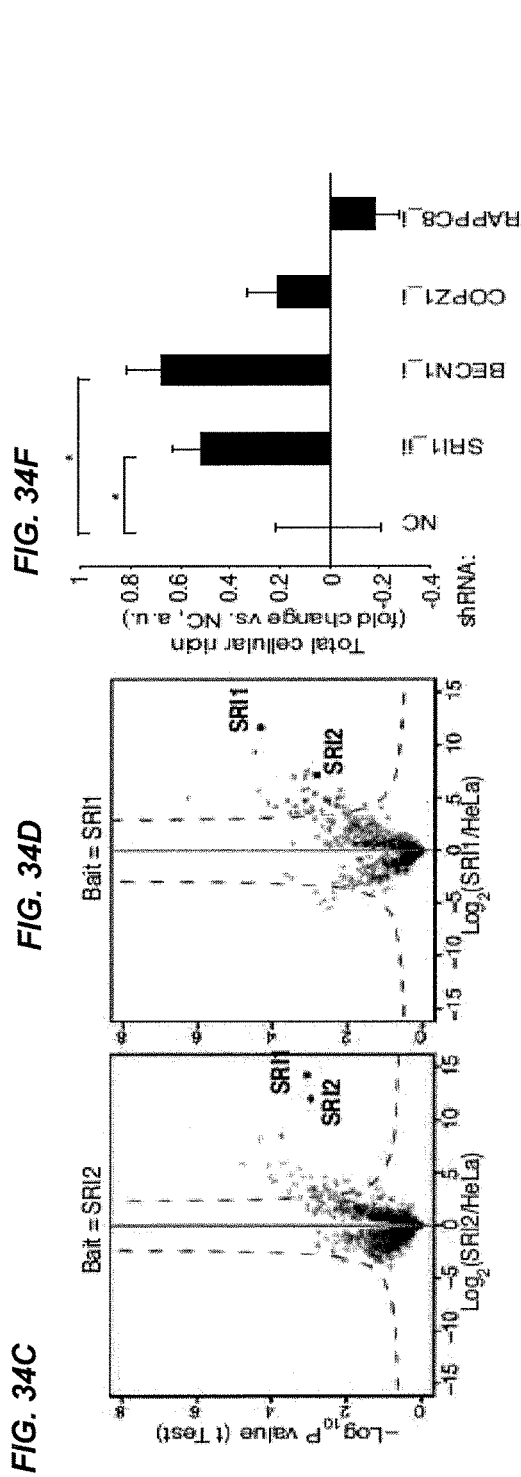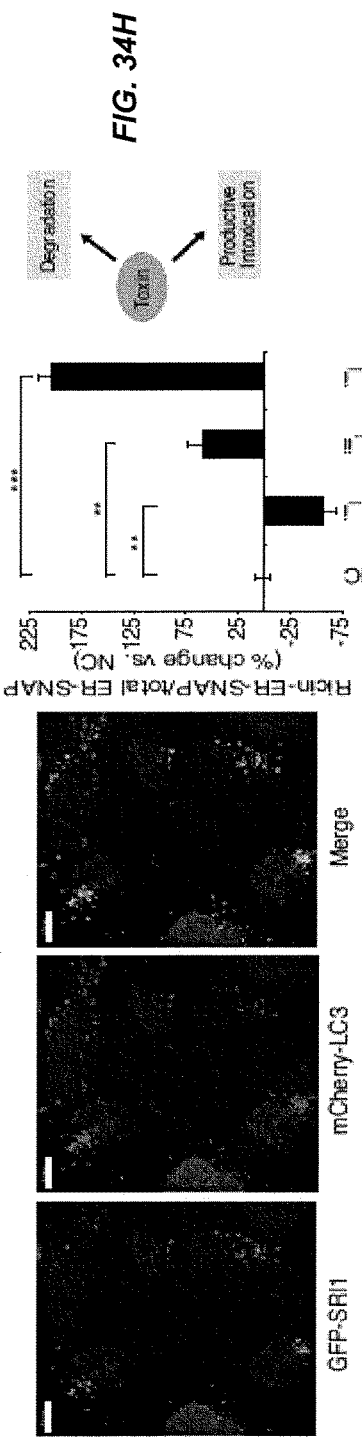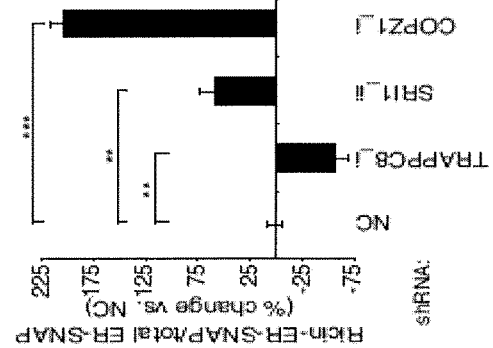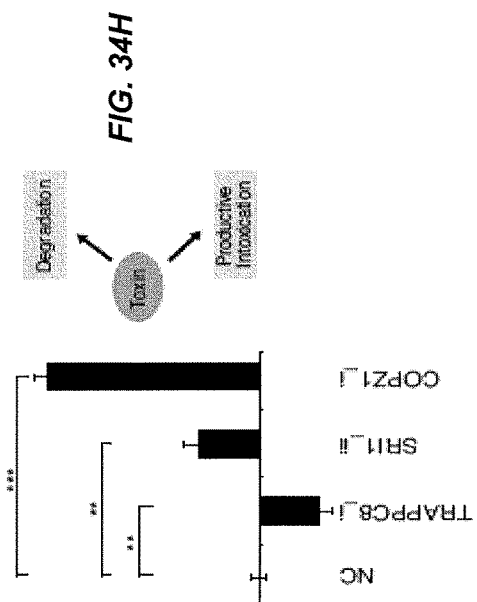

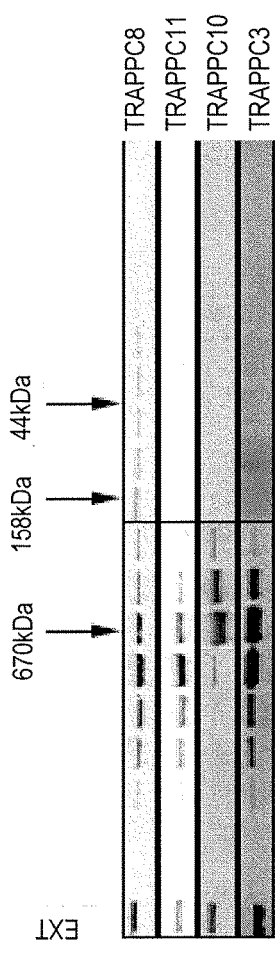
*FIG. 35E*
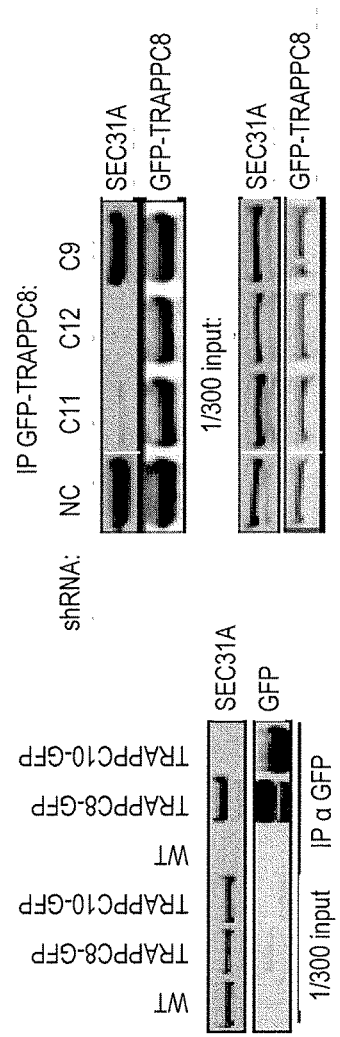
*FIG. 35G*
*FIG. 35F*

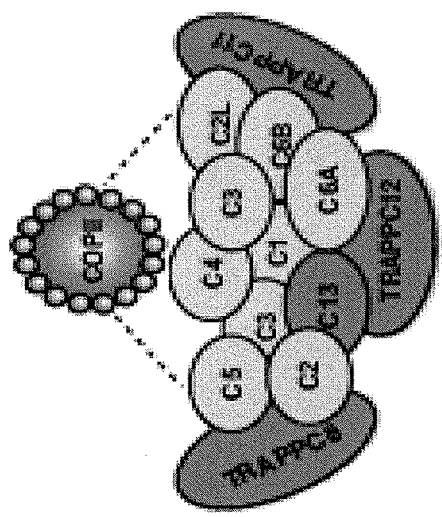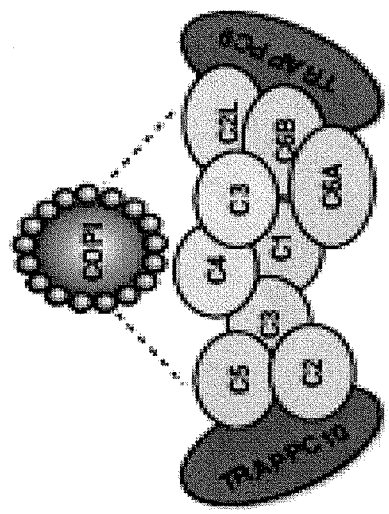
FIG. 35H

METHODS FOR GENOME-WIDE SCREENING AND CONSTRUCTION OF GENETIC INTERACTION MAPS

CROSS-REFERENCE TO RELATED APPLICATION

The present application is a continuation of PCT/US2013/025215, filed Feb. 7, 2013, which application claims priority to U.S. Provisional Application No. 61/598,296, filed Feb. 13, 2012, and the disclosure of each such application is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant (or Contract) No. 1U01CA168370-01, awarded by the National Institutes of Health/National Cancer Institute. The Government has certain rights in this invention.

BACKGROUND OF THE INVENTION

Genetic screens are an essential tool in molecular biology, leading to the discovery of new genes and molecular pathways that are essential for health and disease regulation. RNA interference (RNAi), a natural cellular process by which short double-stranded RNA sequences target expressed genes for degradation and silencing, is widely used as a genetic screening tool. For RNAi screens, shRNA/siRNA libraries are screened for a particular cellular or physiological response. The advantage of an RNAi screen, as opposed to traditional mutagenesis, is that the shRNA hits identify the affected genes, abrogating the need for positional cloning analysis. However, RNAi screening technology is currently hampered by technical challenges. For instance, the high incidence of off-target effects complicates the identification of genuine hits. Furthermore, RNAi screens identify large numbers of hit genes, which must be validated on an individual basis by time-consuming secondary screens. In addition, there are no current methods for assessing if, or how, the hit genes interact to form cellular pathways. The present invention satisfies these needs and provides related advantages as well.

BRIEF SUMMARY OF THE INVENTION

The present invention provides, inter alia, methods for conducting screens using nucleic acid elements (e.g., interfering RNAs) to confidently identify hit genetic elements (e.g., genes associated with cancer). The present invention further comprises constructing vectors that contain two or more nucleic acid elements (e.g., double-RNAi constructs) to knock down all pairwise combinations of the hit genetic elements identified from the screen. Following quantitation of the single and double-knockdown phenotypes, genetic interactions between all gene pairs can be calculated. Genes can then be clustered according to the similarity of the pattern of their interactions with all of the other genes to obtain a genetic interaction map, which can advantageously be used to predict functional associations between genes and identify drug targets for therapy such as combination cancer therapy.

As such, the present invention provides an integrated platform for genome-wide screening and mapping of genetic interactions. In particular embodiments, the methods of the invention provide an integrated suite of experimental and computational approaches to robustly identify genes of interest using pooled RNAi-based screens in mammalian cells and to systematically map genetic interactions (GIs) between these genes to uncover functional relationships.

In one aspect, the present invention provides a method for conducting a primary screen for identifying one or a plurality of genetic elements phenotypically responsive to one or a plurality of modulating nucleic acid elements, the method comprising:
  (a) infecting a plurality of mammalian cells with (1) at least 10 different modulating nucleic acid elements per genetic element and (2) a plurality of different non-modulating nucleic acid elements, thereby forming a plurality of test-infected mammalian cells each comprising a different modulating nucleic acid element and a plurality of control-infected mammalian cells each comprising a different non-modulating nucleic acid element;
  (b) separating a selected pool of the plurality of test-infected mammalian cells and the plurality of control-infected mammalian cells expressing a detectable phenotype from a non-selected pool of the plurality of test-infected mammalian cells and the plurality of control-infected mammalian cells not expressing the detectable phenotype;
  (c) quantitating the frequencies of the modulating nucleic acid elements and the non-modulating nucleic acid elements in the selected pool relative to the frequencies of the modulating nucleic acid elements and the non-modulating nucleic acid elements in the non-selected pool, thereby generating (1) a test enrichment value for the at least 10 different modulating nucleic acid elements per genetic element and (2) a control enrichment value for the plurality of different non-modulating nucleic acid elements; and
  (d) detecting statistically significant differences between the test and control enrichment values, thereby identifying one or a plurality of genetic elements phenotypically responsive to one or a plurality of the modulating nucleic acid elements.

In some embodiments, the plurality of mammalian cells in step (a) is infected with at least 15, 20, or 25 different modulating nucleic acid elements per genetic element. In other embodiments, the plurality of mammalian cells in step (a) is infected with at least 25, 50, 75, 100, 250, 500, 750, 1000, 2000, or 5000 different non-modulating nucleic acid elements. In some embodiments, the modulating and non-modulating nucleic acid elements are interfering RNAs. In certain instances, the modulating nucleic acid elements target genetic elements. In certain other instances, the non-modulating nucleic acid elements comprise negative control interfering RNAs that do not target genetic elements. Non-limiting examples of interfering RNAs include siRNAs, shRNAs, aiRNAs, miRNAs, Dicer-substrate dsRNAs, antisense oligonucleotides, ssRNAi oligonucleotides, RNAs directing the activity of proteins that affect genome sequence or gene expression (e.g., the bacterial CRISPR system), and combinations thereof.

In particular embodiments, the one or a plurality of genetic elements identified by the methods of the present invention corresponds to one or a plurality of genes that promote tumor growth and/or resistance to one or more anticancer drugs.

A pool of infected mammalian cells (e.g., a plurality of test-infected mammalian cells and/or plurality of control-infected mammalian cells) can be selected based upon the presence of a detectable phenotype. Examples of detectable phenotypes include, but are not limited to, cell growth, cell survival, reporter gene expression, physical characteristics of the cell (e.g., shape, size, mass, and/or density), cell mobility or migration behavior, cellular appearance or morphology, and combinations thereof.

In some embodiments, the pool of the plurality of test-infected mammalian cells and plurality of control-infected mammalian cells is selected based upon survival in the presence of at least one anticancer drug. Examples of anticancer drugs include, but are not limited to, monoclonal antibodies, tyrosine kinase inhibitors, anti-proliferative agents, chemotherapeutic agents, toxins, and combinations thereof.

In certain embodiments, the pool of the plurality of test-infected mammalian cells and plurality of control-infected mammalian cells is selected based upon reporter gene expression. In certain instances, the reporter comprises a fluorescent reporter. In some instances, the reporter is used for affinity purification.

In other embodiments, the pool of the plurality of test-infected mammalian cells and plurality of control-infected mammalian cells is selected based upon one or more physical characteristics of the cells, such as, e.g., shape, size, mass, and/or density. In still yet other embodiments, the pool of the plurality of test-infected mammalian cells and plurality of control-infected mammalian cells is selected based upon their mobility and/or migration behavior. In further embodiments, the pool of the plurality of test-infected mammalian cells and plurality of control-infected mammalian cells is selected based upon their appearance or morphology, e.g., using a microscope-coupled cell sorting device.

In certain embodiments, the statistically significant differences between the test and control enrichment values are detected using a non-parametric statistical analysis. Examples of non-parametric statistical analyses include, without limitation, the Mann-Whitney U test, the Kolmogorov-Smirnov test, and combinations thereof.

In some embodiments, the modulating and non-modulating nucleic acid elements are cloned into different vectors each comprising a unique barcode. In other embodiments, step (c) comprises quantitating the frequencies of the modulating and non-modulating nucleic acid elements by a sequencing technique such as, e.g., deep sequencing.

In another aspect, the present invention provides a method for retesting modulating nucleic acid elements selected from the primary screen above to which genetic elements were phenotypically responsive. In one embodiment, individually barcoded vectors for expression of the modulating nucleic acid elements selected from the primary screen are constructed. In some instances, these vectors are pooled for batch retesting of the RNAi phenotypes. In other instances, these vectors can be used to compare the role of the targeted genes in different cell lines, or with different selective pressures. As such, this aspect of the invention identifies one or a plurality of active modulating nucleic acid elements for the same and/or different genetic elements (e.g., hit genes). In some embodiments, a "hit" interfering RNA library is produced comprising a focused library of active interfering RNAs and negative control (NC) interfering RNAs.

In yet another aspect, the present invention provides a composition comprising one or a plurality of modulating nucleic acid elements (e.g., identified from the primary screening method described above), wherein one or a plurality of genetic elements are phenotypically responsive to one or a plurality of the modulating nucleic acid elements. In certain instances, one or a plurality of modulating nucleic acid elements selected from the primary screen are identified as active modulating nucleic acid elements based upon retesting these modulating nucleic acid elements, e.g., using batch retesting of the RNAi phenotypes. In some instances, a modulating nucleic acid element is identified as active when it inhibits the expression of the genetic element by at least 50% (e.g., at least 55%, 60%, 65%, 70%, 75%, 80%, 85%, 90% or 95%).

In still yet another aspect, the present invention provides a method for conducting a secondary screen for identifying a first and a second modulating nucleic acid element that target a first and a second genetic element, the method comprising:
  (a) cloning a first modulating nucleic acid element with a second modulating nucleic acid element to form a double-modulating vector comprising the first modulating nucleic acid element linked to the second modulating nucleic acid element, wherein the first modulating nucleic acid element targets a first genetic element and the second modulating nucleic acid element targets a second genetic element;
  (b) repeating step (a) using a plurality of different first modulating nucleic acid elements and a plurality of different second modulating nucleic acid elements, thereby forming a plurality of different double-modulating vectors;
  (c) infecting a plurality of mammalian cells with the plurality of different double-modulating vectors, thereby forming a plurality of double-modulating vector-infected mammalian cells;
  (d) separating a selected pool of the plurality of double-modulating vector-infected mammalian cells expressing a detectable phenotype from a non-selected pool of the plurality of double-modulating vector-infected mammalian cells not expressing the detectable phenotype; and
  (d) quantitating the frequencies of the first modulating nucleic acid element linked to the second modulating nucleic acid element in the selected pool relative to the frequencies of the first modulating nucleic acid element linked to the second modulating nucleic acid element in the non-selected pool, thereby identifying a first and a second modulating nucleic acid element that target a first and a second genetic element.

In certain embodiments, the secondary screening method further comprises:
  (1) cloning a first non-modulating nucleic acid element with a second non-modulating nucleic acid element to form a double-non-modulating vector; and/or
  (2) cloning the first or second modulating nucleic acid element with a non-modulating nucleic acid element to form a mixed-modulating/non-modulating vector.

In one particular embodiment, the method further comprises:
  (a) cloning a first non-modulating nucleic acid element with a second non-modulating nucleic acid element to form a double non-modulating vector comprising the first non-modulating nucleic acid element linked to the second non-modulating nucleic acid element, wherein the first non-modulating nucleic acid element and the second modulating nucleic acid element do not target a genetic element;
  (b) repeating step (a) using a plurality of different first non-modulating nucleic acid elements and a plurality of different second non-modulating nucleic acid elements, thereby forming a plurality of different double non-modulating vectors;

(c) infecting a plurality of mammalian cells with the plurality of different double non-modulating vectors, thereby forming a plurality of double non-modulating vector-infected mammalian cells;

(d) separating a selected pool of the plurality of double non-modulating vector-infected mammalian cells expressing a detectable phenotype from a non-selected pool of the plurality of double non-modulating vector-infected mammalian cells not expressing the detectable phenotype; and (e) quantitating the frequencies of the first non-modulating nucleic acid element linked to the second non-modulating nucleic acid element in the selected pool relative to the frequencies of the first non-modulating nucleic acid element linked to the second non-modulating nucleic acid element in the non-selected pool.

In certain instances, the frequencies of the first and second non-modulating nucleic acid elements in the selected pool and/or non-selected pool are compared to the frequencies of the first and second modulating nucleic acid elements.

In another particular embodiment, the method further comprises:

(a) cloning the first or second modulating nucleic acid element with a first non-modulating nucleic acid element to form a mixed-modulating/non-modulating vector comprising the first or second modulating nucleic acid element linked to the first non-modulating nucleic acid element, wherein the first non-modulating nucleic acid element does not target a genetic element;

(b) repeating step (a) using a plurality of different first or second modulating nucleic acid elements and a plurality of different first non-modulating nucleic acid elements, thereby forming a plurality of different mixed-modulating/non-modulating vectors;

(c) infecting a plurality of mammalian cells with the plurality of different mixed-modulating/non-modulating vectors, thereby forming a plurality of mixed-modulating/non-modulating vector-infected mammalian cells;

(d) separating a selected pool of the plurality of mixed-modulating/non-modulating vector-infected mammalian cells expressing a detectable phenotype from a non-selected pool of the mixed-modulating/non-modulating vector-infected mammalian cells not expressing the detectable phenotype; and (e) quantitating the frequencies of the first or second modulating nucleic acid element linked to the first non-modulating nucleic acid element in the selected pool relative to the frequencies of the first or second modulating nucleic acid element linked to the first non-modulating nucleic acid element in the non-selected pool.

In certain instances, the frequencies of the first or second modulating nucleic acid element and the first non-modulating nucleic acid element in the selected pool and/or non-selected pool are compared to the frequencies of the first and second modulating nucleic acid elements.

In some embodiments, step (a) comprises cloning all of the pairwise combinations of (1) two or more modulating nucleic acid elements that each target a first genetic element, (2) two or more modulating nucleic acid elements that each target a second genetic element, and (3) one or a plurality of non-modulating nucleic acid elements, to form a plurality of vectors containing all pairwise combinations of the modulating and non-modulating nucleic acid elements.

In other embodiments, the method further comprises:
detecting differences between the frequencies of the first modulating nucleic acid element linked to the second modulating nucleic acid element in the selected pool relative to a calculated control frequency, thereby identifying a genetic interaction between the first and second genetic elements.

In some embodiments, the genetic interaction corresponds to a buffering genetic interaction or a synergistic genetic interaction. In certain embodiments, the presence of a synergistic genetic interaction indicates that the first and second genetic elements act in parallel pathways. In some instances, the first genetic element and second genetic element act synergistically, e.g., to promote tumor growth and/or resistance to one or more anticancer drugs. In other embodiments, the presence of a buffering genetic interaction indicates that the first and second genetic elements act in a linear pathway.

In yet other embodiments, the method further comprises screening the vectors set forth herein (e.g., double-modulating vectors, double-non-modulating vector, and/or mixed-modulating/non-modulating vectors) for different phenotypes and/or in different cell lines.

In still yet other embodiments, the vectors set forth herein (e.g., double-modulating vectors, double-non-modulating vector, and/or mixed-modulating/non-modulating vectors) comprise (1) a unique barcode for each of the modulating and non-modulating nucleic acid elements or (2) a combinatorial barcode that detects both nucleic acid elements cloned into the vectors. In further embodiments, step (e) comprises quantitating the frequencies of the nucleic acid elements cloned into the vectors set forth herein by a sequencing technique such as deep sequencing.

In yet another particular embodiment, the method (e.g., step (a)) further comprises:

(1) cloning a first modulating nucleic acid element with a second modulating nucleic acid element and a third modulating nucleic acid element to form a triple-modulating vector comprising the first modulating nucleic acid element linked to the second and third modulating nucleic acid elements, wherein the first modulating nucleic acid element targets a first genetic element, the second modulating nucleic acid element targets a second genetic element, and the third modulating nucleic acid element targets a third genetic element; and/or (2) cloning (i) the first, second, or third modulating nucleic acid element with two different non-modulating nucleic acid elements, and/or (ii) two of the first, second, or third modulating nucleic acid elements with a non-modulating nucleic acid element, to form one or more different types of mixed-modulating/non-modulating vectors; and/or (3) cloning three different non-modulating nucleic acid elements to form a triple-non-modulating vector.

Other objects, features, and advantages of the present invention will be apparent to one of skill in the art from the following detailed description and figures.

BRIEF DESCRIPTION OF THE DRAWINGS

FIGS. 14A-C illustrate an example of quantitative genetic interactions identified by the methods of the invention. (A) Two mutants, AA and AB, both reduce fitness. The phenotype of the double mutant is either typical (no interaction between A and B), less severe (positive/buffering interaction) or more severe (negative/synergistic interaction). (B) Possible pathways between A, B and the phenotype underlying positive and negative interactions. (C) The interaction pattern of a given gene with all other genes is its phenotypic signature.

FIGS. 18A-C illustrate that hits from a genome-wide screen recapitulate known ricin biology. (A) Overview of ricin intoxication of mammalian cells. Ricin is taken up by endocytosis and traffics retrogradely to the ER, where ricin A and B chains dissociate. The A chain retrotranslocates to the cytoplasm and cleaves ribosomal RNA, thereby inhibiting protein synthesis and ultimately triggering apoptosis. (B) GO-term enrichment analysis for top hits. Top hits were defined as the set of 73 protective genes with an FDR<0.05 and 83 sensitizing genes with an FDR<0.02. Non-redundant GO-terms with an FDR<0.05 are shown; biological process (black bars), cellular component (gray bars). (C) Visualization of top hits in cellular pathways as blue circles (protective hits) and red circles (sensitizing hits); circle area is proportional to –log 10 P value. Selected hits below the top hit cutoff were included (pink and light blue circles) if they were part of a known physical complex containing a top hit, or if they were part of the GI map presented in FIG. 20. Gray ovals indicate known physical complexes, the asterisk identifies the SRI complex identified in this study.

FIG. 19A illustrates that 60S depletion sensitizes to ricin, but RPS25 knockdown protects. FIG. 19B illustrates that COPI depletion sensitizes to ricin. FIG. 19C illustrates that cholesterol metabolism modulates ricin sensitivity.

FIGS. 23A-C illustrate the correlation of genetic interaction patterns for shRNAs targeting the same gene. shRNAs with insufficient correlation of their genetic interaction pattern to other shRNAs designed to target the same gene are removed during data analysis and calculation of the genetic interaction map before.

FIGS. 26A-F illustrate a quantitative framework for phenotypes and primary hit detection. (A) Illustration of exponential growth of WT cells (black) and cells expressing an shRNA X (gray) under standard conditions (unselected population, solid lines) or selective pressure (selected population, dotted lines). shRNA X affects the growth rate g for unselected cells by a factor $(1+\gamma_X)$ and the selective pressure k by a factor $(1-\rho_X)$. (B) Illustration of the biological meaning of the quantitative phenotypes $\gamma$ and $\rho$. (C) Calculation of $\gamma$ for shRNAs from two independent experimental replicates shows excellent agreement. Grey lines: WT phenotype. (D) Calculation of $\rho$ for shRNAs from experiments with slightly different selective pressures kt show good agreement. Grey lines: WT phenotype. (E) The current ultracomplex shRNA library targets each human protein-coding gene with ~25 shRNAs and also contains >1,000 negative-control shRNAs not targeting any human transcript. To detect hits in the primary screen, P values for each gene were calculated using the Mann-Whitney U test (MW test), by comparing phenotypes of shRNAs targeting each gene to the phenotypes of negative-control shRNAs. (F) A ricin resistance screen was carried out with a test library targeting 1,079 genes with 50 shRNAs each. For analysis, the shRNAs targeting each gene were randomly divided into two groups of 25 shRNAs, and P values for each gene were calculated based on these "half-libraries" and are plotted here. Genes were called hits for a false-discovery rate (FDR)<5% (grey lines). The overlap in called hits based on the two half-libraries is highly significant (P=2·10-29, Fisher's exact test).

FIGS. 32A-E illustrate that characterization of hit genes from the primary screen. (A) K562 cells were treated with ricin in the presence or absence of atorvastatin for 24 h, and then allowed to recover in the continued presence of atorvastatin. The percentage of viable cells was quantified using flow cytometry. (B) Cells expressing ER-localized SNAP were intoxicated with benzylguanine-labeled ricin and covalent ricin-SNAP complexes were detected by anti-SNAP Western blot. (C) Quantification of ricin modified fraction of ER-SNAP. (D) Raji B cells were infected with shRNAs targeting the indicated genes, and a competitive growth assay was performed in the presence of either ricin or shiga toxin. (E) COPZ1 knockdown increases levels of ER-localized ricin as measured by the SNAP assay.

FIGS. 33A-F illustrate the effects of combinatorial gene knockdowns by double-shRNAs. (A) Experimental strategy: Active shRNAs targeting hit genes from the primary screen were individually cloned and barcodes are added upstream and downstream of the mir30 context. Pooled ligation yielded a library of all pairwise combinations of shRNAs. Ricin resistance phenotypes of double-shRNAs were determined as for the primary screen; double-shRNA were identified by sequencing the combinatorial barcode. (B) Reproducibility between phenotypes of individual shRNAs in a batch retest (mean of two experiments +/− spread) and the same shRNAs paired with negative control shRNAs in a double-shRNA screen (mean+/−SD for combinations with 12 different negative control shRNAs). (C) Reproducibility between two permutations of double shRNA constructs representing (negative control+targeted) or (targeted+negative control), mean+/−SD for combinations with 12 different negative control shRNAs. (D) Genetic interactions are calculated as deviations from the typical double-mutant phenotype. The relationship between single shRNA phenotypes and double-shRNA phenotypes in combination with an shRNA of interest (in this example SEC23B_i) is typically linear (solid line). Deviations from this line are defined as genetic interactions. Buffering interactions are closer to WT phenotype than expected, as in this case found for double-shRNAs targeting SEC23B twice. Synergistic interactions are further away from WT than expected, as in this case found for double-shRNAs targeting both isoforms of SEC23, SEC23A and SEC23B. (E) Phenotypes for individual and combinatorial SEC23A, SEC23B knockdown measured in competitive growth assay (mean of triplicate experiments +/−SD). (F) Quantification of ER localization of ricin measured by the SNAP assay in different knockdown strains (mean of triplicate experiments +/−SD).

FIGS. 34A-H illustrate novel interactions predicted from the GI Map: RPS25/NFAT and SRIC. (A) Buffering genetic interactions between shRNAs targeting ILF3, the ribosomal subunit RPS25, and ILF2/ILF3. (B) Correlation and buffering genetic interactions between shRNAs targeting ILF2, ILF3 and RPS25 in an shRNA-based genetic interaction map. (C, D) The poorly characterized, genetically correlated proteins SRI1 and SRI2 interact physically, as shown by reciprocal co-immunoprecipitation and MS. (E) GFP-SRI1 partially colocalizes with the autophagosome/lysosome marker mCherry-LC3 in HeLa cells. (F) Total cellular ricin levels after intoxication, as quantified by western blotting, are increased upon knockdown of degradation-related genes and SRI1 (which sensitizes to ricin). The asterisk indicates statistically significant differences (P<0.05, Student's t test). (G) SRI1 and COPZ1 knockdown increase levels of ER-localized ricin as measured by the SNAP assay, whereas TRAPPC8 knockdown decreases levels of ER-localized ricin. The asterisks indicate statistically significant differences (, P<0.01; *, P<0.001; Student's t test). (H) Model: Ricin partitions between degradation and productive intoxication pathways; inhibition of degradation increases productive intoxication.

FIGS. 35A-H illustrate the functional dissection of the TRAPP complex. (A-B) All TRAPP complex members (other than TRAPPC9/10) specifically coimmunoprecipitate with TRAPPC11 (A) and TRAPPC8 (B), as quantified by mass spectrometry. (C) Correlation of genetic interactions with TRAPPC11 and buffering genetic interaction with TRAPPC11 is shown for each gene included in the genetic interaction map. TRAPP complex members and the functionally related SEC22B are shown. TRAPPC9 shows a strongly anti-correlated genetic interaction pattern when compared to other TRAPP complex members. (D) Abundance (quantified as LFQ) of each TRAPP subunit in the immunoprecipitation is indicated by scale. (E) Extracts from K562 cells were fractionated by size exclusion chromatography on a superose 6 column. Western blot could detect co-migration of TRAPPC8 and TRAPPC11, which were larger in size than TRAPPC10. The core component TRAPPC3 migrated with both components. EXT=unfractionated extract. (F) Immunoprecipitation of TRAPPC8 or TRAPPC10 tagged with GFP showed specific association of TRAPPC8 with SEC31A. (G) Association of GFP-TRAPPC8 with SEC31A was assessed by immunoprecipitation in extracts from cells stably expressing shRNAs targeting the indicated TRAPP components. (H) Hypothetical model for mammalian TRAPP complexes. At least two complexes are proposed to exist, which contain a core set of proteins and unique subunits, either TRAPPC9/10 or TRAPPC8/11/12/13, which associate with COPI or COPII vesicles, respectively.

DETAILED DESCRIPTION OF THE INVENTION

I. Introduction

Figure 1:
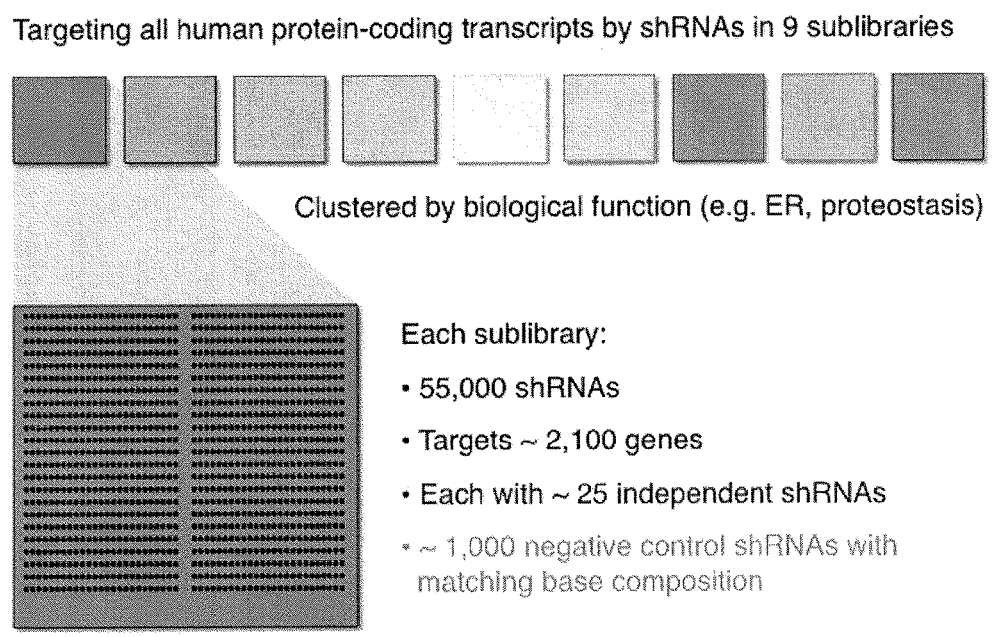
FIG. 1 illustrates the design of an exemplary human genome-wide ultra-complex shRNA library of the invention.

The use of RNA interference (RNAi) technology to conduct genetic screens is a widespread technique for identifying genes required for a given process. The potential for doing comprehensive forward genetic screens in mammalian systems is enormous, but in practice the utility has been hampered by a number of technical challenges. Moreover, even when successful, such screens often identify large numbers of "hit" genes, but there is no systematic method for understanding how these hit genes may function together. In addition, RNAi technologies have been plagued by off-target effects, where a potential hit cannot be verified as genuine because the shRNA or siRNA designed to target a single gene has unknown secondary targets with functional consequences.

The present invention overcomes these and other limitations associated with current RNAi-based screening tools by providing methods and statistical analyses (e.g., algorithms) that enable, for the first time, the creation of genetic interaction maps from genome-wide primary RNAi screen data. These methods and statistical analyses (e.g., algorithms) of the invention are particularly useful for distinguishing true hit genes from off-target effects. The ability to create high-fidelity genetic interaction maps represents a great advance in RNAi screening technology, as it enables the identification of the functions of novel genes, the discovery novel biological pathways relevant to health and disease, and the optimization of strategies for targeted secondary screens. Furthermore, the methods and statistical analyses (e.g., algorithms) of the invention of the invention can be used to discover novel drug targets and inform combination drug therapy by enabling the mapping of cellular pathways as they are impacted by a particular drug or disease process.

In certain aspects, the present invention provides methods for conducting an RNAi screen and confidently identifying hit genes, and then using double-RNAi constructs to knock down all pairwise combinations of these hit genes. Following quantitation of the single and double-knockdown phenotypes, genetic interactions between all gene pairs can be calculated. Genes are then clustered according to the similarity of the pattern of their interactions with all of the other genes to obtain a genetic interaction map. This map can then be used to predict functional associations between genes.

In particular embodiments, the present invention provides high-coverage shRNA libraries synthesized by microarray, which are used to conduct screens and then analyzed by deep sequencing. The present invention also provides statistical analyses (e.g., algorithms) to analyze the data from primary screens in order to identify both hit genes and individual active shRNAs targeting these hit genes. The present invention further provides an optimized chip design to facilitate the detection of statistically significant hit genes and active shRNAs in the presence of experimental noise and off-target effects. In some instances, the individual shRNAs that are identified as actively targeting hits can be cloned into a barcoded vector, and these barcoded shRNAs can be concatenated by ligation to yield a double-barcoded vector expressing two shRNAs. The resulting double barcode can then be read by deep sequencing. Sequencing bias can be minimized by directly sequencing the barcode rather than a hairpin with extensive secondary structure.

In yet other embodiments, the present invention provides statistical analyses (e.g., algorithms) to quantify genetic interactions from the double shRNA data. Internal measures of reproducibility enable one to separate signal from noise and to assign confidence levels to the detected genetic interactions. In certain instances, double-shRNA constructs can be directly synthesized by microarray with a barcode that can be read by deep sequencing to identify the unique pair.

Accordingly, the methods of the present invention are advantageous because they represent the only methods for generating genetic interaction maps from genome-wide RNAi genetic screen data and for informing secondary screening strategy by identifying promising true hits, thereby reducing the need for time-consuming individual validation. As such, the present invention provides the ability to create genetic interaction maps from primary RNAi screen data, thereby enabling the discovery of novel cellular pathways and the identification of novel gene functions. The present invention also provides the ability to distinguish on and off-target effects of shRNA hits, improving the fidelity of RNAi screen data. In addition, the present invention can be used as a foundation for software to analyze primary screening data, to inform secondary screening strategy, to identify drug targets, and to enable the rapid and rational design of combination therapies in which pairs of drugs lead to synergistic beneficial effects.

II. Definitions

As used herein, the following terms have the meanings ascribed to them unless specified otherwise.

The term "interfering RNA" or "RNAi" includes single-stranded RNA (e.g., mature miRNA, ssRNAi oligonucleotides, antisense oligonucleotides), double-stranded RNA (i.e., duplex RNA such as siRNA, shRNA, Dicer-substrate dsRNA, aiRNA, pre-miRNA), RNAs directing the activity of proteins that affect genome sequence or gene expression (e.g., the bacterial CRISPR system and applications thereof), single-stranded DNA (e.g., morpholino oligonucleotides), a DNA-RNA hybrid, or a DNA-DNA hybrid that is capable of reducing or inhibiting the expression of a target gene or sequence (e.g., by mediating the degradation and/or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof.

Interfering RNA includes "small hairpin RNA," "short hairpin RNA," or "shRNA." An shRNA includes a short RNA sequence that makes a tight hairpin turn that can be used to silence gene expression via RNA interference (RNAi). shRNAs can be expressed from a vector (e.g., transcribed from a transcriptional cassette in a DNA plasmid) or chemically synthesized. The shRNA hairpin structure is cleaved by the cellular machinery into siRNA, which is then bound to the RNA-induced silencing complex (RISC). shRNAs can typically comprise a sense strand and a complementary antisense strand linked by a hairpin structure, which sense and antisense strands form a double-stranded (e.g., duplex) region of about 15-60, 15-50, 15-40, 15-30, 15-25, or 19-25 nucleotides (e.g., base pairs) in length. In certain instances, shRNA duplexes may comprise 3' overhangs and/or 5'-phosphate termini. Non-limiting examples of shRNAs include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions.

Interfering RNA also includes "small-interfering RNA" or "siRNA." An siRNA includes a short double-stranded RNA sequence that can be used to silence gene expression via RNA interference (RNAi). siRNAs can be expressed from a vector (e.g., transcribed from a transcriptional cassette in a DNA plasmid) or chemically synthesized. siRNAs can typically comprise a sense strand and a complementary antisense strand, which sense and antisense strands form a double-stranded (e.g., duplex) region of about 15-60, 15-50, 15-40, 15-30, 15-25, or 19-25 nucleotides (e.g., base pairs) in length. In certain instances, siRNA duplexes may comprise 3' overhangs and/or 5'-phosphate termini. Examples of siRNAs include, without limitation, double-stranded polynucleotide molecules assembled from two separate stranded molecules, wherein one strand is the sense strand and the other strand is the complementary antisense strand.

Interfering RNA also includes an RNA directing the activity of proteins that affect genome sequence or gene expression, such as, e.g., in applications of the bacterial CRISPR system. "CRISPRs" or Clustered Regularly Interspaced Short Palindromic Repeats are loci containing multiple short direct repeats that are found in the genomes of bacteria and archaea. Small RNAs target invaders for silencing in the CRISPR-Cas pathways that protect bacteria and archaea from viruses and plasmids. The CRISPR RNAs (crRNAs) contain sequence elements acquired from invaders that guide CRISPR-associated (Cas) proteins back to the complementary invading DNA or RNA. Hale et al. (Molecular Cell, 45:292-302 (2012)) analyzed essential features of the crRNAs associated with the Cas RAMP module (Cmr) effector complex, which cleaves targeted RNAs, and found that Cmr crRNAs contain an 8 nucleotide 5' sequence tag that is critical for crRNA function and can be used to engineer crRNAs that direct cleavage of novel targets. In particular embodiments, the CRISPR RNA-Cmr protein pathway of the CRISPR system is exploited to cleave RNAs to thereby affect genome sequence or gene expression, e.g., by knocking down or inhibiting the expression of a target gene of interest.

A "nucleic acid" includes a polymer comprising at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of siRNA, shRNA, Dicer-substrate dsRNA, asymmetrical interfering RNA (aiRNA), microRNA (miRNA), mRNA, tRNA, rRNA, tRNA, viral RNA (vRNA), RNAs directing the activity of proteins that affect genome sequence or gene expression (e.g., applications of the bacterial CRISPR system), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). "Nucleotides" contain a sugar deoxyribose (DNA) or ribose (RNA), a base, and a phosphate group. Nucleotides are linked together through the phosphate groups. "Bases" include purines and pyrimidines, which further include the natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "genetic element" or "gene" includes a nucleic acid (e.g., DNA or RNA) sequence comprising partial length or entire length coding sequences necessary for the production of a polypeptide or precursor polypeptide. The term "genetic element" or "gene" also includes a nucleic acid (e.g., DNA or RNA) sequence comprising non-coding sequences (e.g., non-coding RNAs).

The term "modulating nucleic acid element" includes a nucleic acid element that targets and modulates (e.g., inhibits such as decreases or down-regulates, or activates such as increases or upregulates) the expression of one or a plurality of genetic elements of interest.

The term "non-modulating nucleic acid element" includes a nucleic acid element that does not target or modulate one or a plurality of genetic elements of interest, and thus serves as a negative control in the methods of the invention. In some embodiments, a non-modulating nucleic acid element corresponds to a negative control interfering RNA (e.g., a negative control shRNA) that contains the same overall base composition as a modulating nucleic acid element, but that does not match the sequence of any human transcript.

The term "enrichment value" includes a measure of the frequency of a modulating or non-modulating nucleic acid element in a selected pool compared to a non-selected pool. In particular embodiments, the enrichment value comprises a ratio of the frequency of a modulating or non-modulating nucleic acid element in a selected pool compared to a non-selected pool. As a non-limiting example, the logarithm of the ratio of the frequency of a modulating or non-modulating nucleic acid element in a selected pool over the frequency in a non-selected pool is calculated. In certain embodiments, the enrichment value is a "test enrichment value" that is calculated by comparing the frequency of a modulating nucleic acid element of interest in selected and non-selected pools. In other embodiments, the enrichment value is a "control enrichment value" that is calculated by comparing the frequency of a non-modulating nucleic acid element of interest in selected and non-selected pools.

The term "detectable phenotype" includes any cellular phenotype that can be detected and used to separate or split one population or pool of cells from another. In particular embodiments, cells of interest can be selected based upon the presence of a detectable phenotype. Examples of detectable phenotypes include, but are not limited to, cell growth, cell survival, reporter gene expression, physical characteristics of the cell (e.g., shape, size, mass, and/or density), cell mobility or migration behavior, cellular appearance or morphology, and combinations thereof. In certain embodiments, a detectable phenotype is used to determine whether a genetic element is phenotypically responsive to a modulating nucleic acid element. In other embodiments, a detectable phenotype is a phenotype that is observed with one (single-mutant phenotype), two (double-mutant phenotype), three, four, five, six, seven, eight, nine, ten, or more mutations and used to identify one or a plurality of genetic elements, one or a plurality of nucleic acid elements that modulate genetic elements, and/or genetic interactions between genetic elements.

The term "selected pool" includes a population or pool of cells that is selected based upon one or more detectable phenotypes. In general, the selected pool of cells expresses the detectable phenotype of interest. As non-limiting examples, cells can be selected based upon survival, e.g., in the presence of at least one anticancer drug, cell growth and/or proliferation, reporter gene expression, physical characteristics of the cell, such as, e.g., shape, size, mass, or density, cell mobility or migration behavior, cellular appearance or morphology, as well as combinations thereof. A "non-selected pool" as used herein includes a population or pool of cells that is separated or split from the selected pool because it does not express the detectable phenotype.

As used herein, a genetic element is "phenotypically responsive" to a modulating nucleic acid element when the genetic element is modulated by the modulating nucleic acid element to produce a detectable phenotype.

The term "control frequency" as used herein includes an expected frequency that is calculated based at least in part on a demonstrated independent effect of a nucleic acid element (e.g., a first nucleic acid element or a second nucleic acid element) on a detectable phenotype. In particular embodiments, the control frequency is calculated from the individual frequencies for a first and second modulating nucleic acid element. In certain embodiments, the calculated control frequency is obtained from detection (e.g., quanititation) of a control (e.g., expected) phenotype (e.g., detecting an amount of an expected phenotype). In certain instances, if the phenotype is directly related to fitness or growth rate, the expected phenotype is commonly defined as the product or sum of the detected amount of single mutant phenotypes. For more complex phenotypes, such as the activation of a reporter gene, the expected phenotype can be defined empirically for each gene. In other instances, the expected phenotype is based on the assumption that strong GIs are rare, such that a fit of the observed phenotypes to a rationally chosen function is used to define the expected phenotype, and GIs are quantified as deviations from this fitted function.

The term "genetic interaction", "GI", or "functional interaction" refers to a measure of the extent to which simultaneous modulation of two or more genes or gene products modulate a phenotype (e.g., a detactable phenotype). For example, a GI includes a measure of the extent to which the phenotype of a first mutation is modified by the presence of one, two, three, four, five, six, seven, eight, nine, ten, or more additional mutations to reveal a potential functional relationship between genes. A GI also includes a measure of the extent to which a phenotype is changed where first nucleic acid sequence that modulates expression of a first gene is combined with one ore more additional nucleic acids that modulate expression of one or more additional genes thereby revealing a potentioal functional relationship between the genes. In some embodiments, the pattern of GIs of a gene provides an information-rich description of its phenotype, which is useful to detect functional similarities between genes and reveal pathways without any prior assumptions about cellular functions. In general, GIs are defined as the deviation of observed double-mutant phenotypes from the phenotype expected based on the two individual mutant phenotypes.

The term "buffering genetic interaction" or "buffering GI" as used herein includes a genetic interaction with a deviation of an amount of an observed phenotype compared to the phenotype of wild-type cells. In some embodiments, a "buffering GI" includes a genetic interaction with a deviation of an observed phenotype towards the phenotype of wild-type cells. In certain embodiments, two or more modulating nucleic acid elements targeting the same gene typically show buffering GIs. In other embodiments, two or more modulating nucleic acid elements targeting the same pathway typically show buffering GIs.

The term "synergistic genetic interaction" or "synergistic GI" includes a genetic interaction in which the amount of an observed phenotype change is greater than the amount of calculated phenotype change based on modulation of each genetic element independently added together. In some embodiments, a "synergistic GI" includes a genetic interaction with a deviation of an observed phenotype that is away from wild-type cells. In certain instances, two or more modulating nucleic acid elements targeting genes acting in parallel may exhibit synergistic GIs.

The term "barcode" includes a sequence of nucleotides uniquely associated with an individual modulating or non-modulating nucleic acid element that enables identification of the individual modulating or non-modulating nucleic acid element from other modulating or non-modulating nucleic acid elements. In some embodiments, the barcode is detected using sequencing techniques (e.g., deep sequencing). In certain instances, the barcode comprises a sequence of about 4 to about 50 nucleotides, of about 4 to about 25 nucleotides, of about 4 to about 20 nucleotides, of about 4 to about 15 nucleotides, of about 8 to about 12 nucleotides, or about 4, 5, 6, 7, 8, 9, 10, 11, 12, 13, 14, 15, 16, 17, 18, 19, or 20 nucleotides. In particular embodiments, each individual modulating or non-modulating nucleic acid element is cloned into a vector containing a unique random barcode (e.g., a 10-nucleotide random barcode). In other embodiments, a combination of two or more different modulating and non-modulating nucleic acid elements are cloned into a vector, and a combinatorial barcode is created by the unique random barcodes for each of two of the nucleic acid elements that are present at the junction between the two nucleic acid elements.

The term "deep sequencing" as used herein includes sequencing a nucleic acid sequence multiple times (e.g., a large number of times relative to the length of the sequence), thereby increasing sequencing accuracy.

The term "algorithm" or "statistical analysis" includes any of a variety of statistical methods and models which can be used to determine relationships between variables. Non-limiting examples of algorithms include logistic regression, linear regression, random forests, classification and regression trees (C&RT), boosted trees, neural networks (NN), artificial neural networks (ANN), neuro fuzzy networks (NFN), network structures, perceptrons such as multi-layer perceptrons, multi-layer feed-forward networks, support vector machines (e.g., Kernel methods), multivariate adaptive regression splines (MARS), Levenberg-Marquardt algorithms, Gauss-Newton algorithms, mixtures of Gaussians, gradient descent algorithms, learning vector quantization (LVQ), and combinations thereof.

The term "mammal" includes any mammalian species such as a human, mouse, rat, dog, cat, hamster, guinea pig, rabbit, livestock, and the like.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, gastric cancer (e.g., stomach cancer), colorectal cancer, gastrointestinal stromal tumors (GIST), gastrointestinal carcinoid tumors, colon cancer, rectal cancer, anal cancer, bile duct cancer, small intestine cancer, esophageal cancer, lung cancer (e.g., non-small cell lung cancer), breast cancer, gallbladder cancer, liver cancer, pancreatic cancer, appendix cancer, prostate cancer, ovarian cancer, renal cancer (e.g., renal cell carcinoma), cancer of the central nervous system, skin cancer, lymphomas, gliomas, choriocarcinomas, head and neck cancers, osteogenic sarcomas, and blood cancers. As used herein, a "tumor" comprises one or more cancerous cells.

III. Description of the Embodiments

Figure 25:
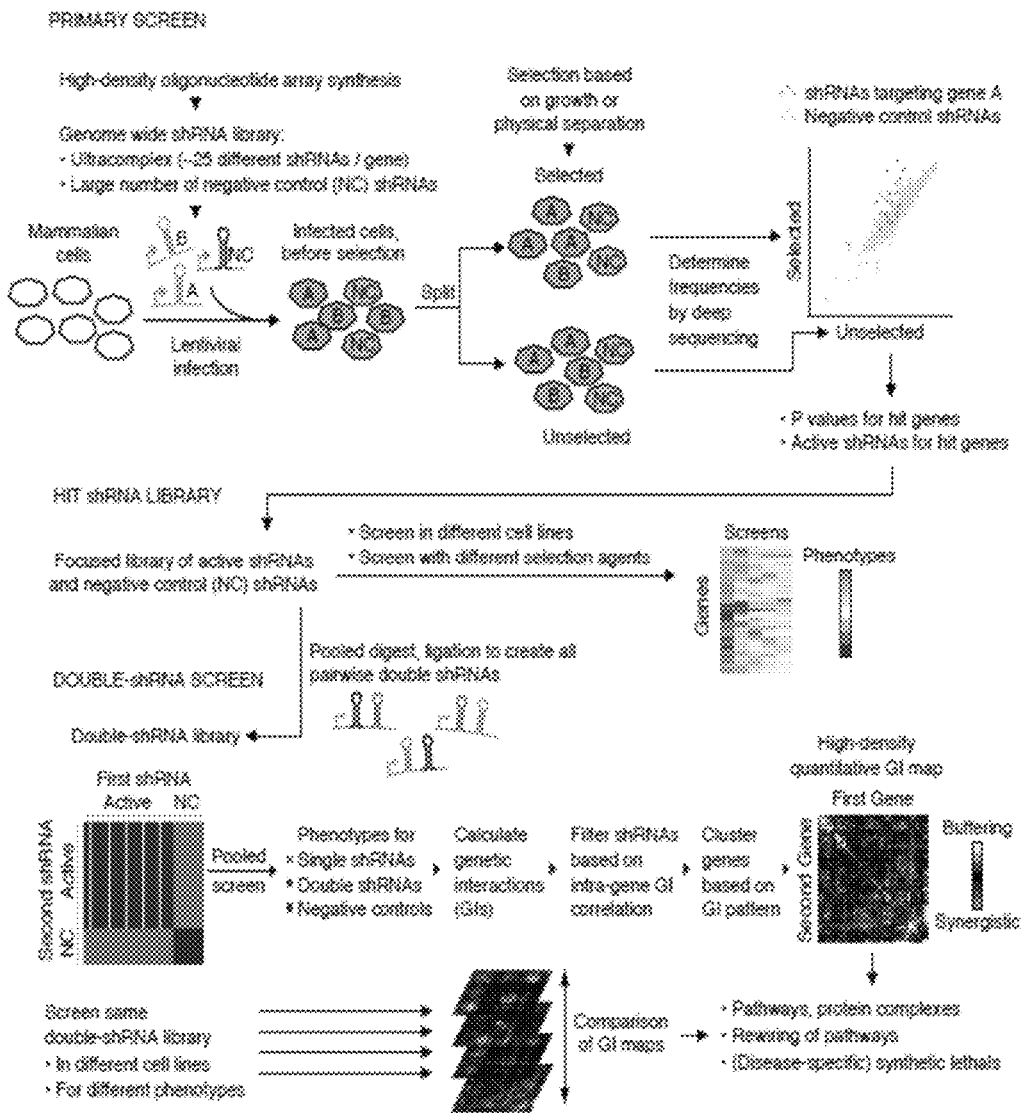
FIG. 25 illustrates an overview of the technology platform of the invention.

In certain aspects, the present invention provides an integrated platform for genome-wide screening and mapping of genetic interactions. In particular embodiments, the methods of the invention provide an integrated suite of experimental and computational approaches to robustly identify genes of interest using pooled RNAi-based screens in mammalian cells and to systematically map genetic interactions (GIs) between these genes to uncover functional relationships. FIG. 25 provides an exemplary overview of the strategy of the invention.

In some embodiments, a pooled ultracomplex library comprising both modulating and non-modulating nucleic acid elements (e.g., interfering RNAs that either target genetic elements or do not target genetic elements) is introduced into cells (e.g., mammalian cells) via viral (e.g., lentiviral) infection at a low multiplicity of infection to conduct an initial primary genome-wide screen. In certain instances, a fraction of this infected cell population can be subjected to selection for a detectable phenotype of interest. Depending on the biological system being interrogated or modulated, this selection can be a period of growth under standard conditions, or growth in the presence of a drug, toxin, or other selective pressure, or selection for cell migration, cell size, or reporter gene expression. The frequencies of RNAi-encoding cassettes in the selected population and in an unselected control population are determined by a sequencing method such as deep sequencing. Genetic elements phenotypically responsive to modulating nucleic acid elements are identified as hit genes, and interfering RNAs that effectively target these hit genes are identified.

In further embodiments, individually barcoded lentiviral vectors for expression of the modulating nucleic acid elements selected from the primary screen described above are constructed. These vectors are pooled for batch retesting of the RNAi phenotypes, and can also be used to compare the role of the targeted genes in different cell lines, or with different selective pressures.

In further embodiments, the barcoded vectors are digested and ligated in a pooled format to generate a library expressing one or more combinations of the modulating and/or non-modulating nucleic acid elements of interest (e.g., all pairwise combinations for double-RNAi constructs). The phenotypes of these multiple interfering RNA-containing vectors can be measured in a pooled screen, combinations of modulating nucleic acid elements targeting different genes can be identified, and from these, genetic interactions (GIs) can be calculated. In some instances, GI patterns of modulating nucleic acid elements targeting the same gene are then averaged and genes are clustered based on their GI pattern to obtain a high-density GI map. Advantageously, the same library comprising multiple interfering RNA-containing vectors can be screened for different phenotypes or in different cell lines to generate a set of GI maps. Comparison of these GI maps can reveal condition- and background-specific GIs and pathways.

As such, in one aspect, the present invention provides a method for identifying one or a plurality of genetic elements (e.g., one or more hit genes) phenotypically responsive to one or a plurality of modulating nucleic acid elements, the method comprising:

(a) infecting a plurality of mammalian cells with (1) at least 10 different modulating nucleic acid elements per genetic element and (2) a plurality of different non-modulating nucleic acid elements, thereby forming a plurality of test-infected mammalian cells each comprising a different modulating nucleic acid element and a plurality of control-infected mammalian cells each comprising a different non-modulating nucleic acid element;

(b) separating a selected pool of the plurality of test-infected mammalian cells and the plurality of control-infected mammalian cells expressing a detectable phenotype from a non-selected pool of the plurality of test-infected mammalian cells and the plurality of control-infected mammalian cells not expressing the detectable phenotype;

(c) quantitating the frequencies of the modulating nucleic acid elements and the non-modulating nucleic acid elements in the selected pool relative to the frequencies of the modulating nucleic acid elements and the non-modulating nucleic acid elements in the non-selected pool, thereby generating (1) a test enrichment value for the at least 10 different modulating nucleic acid elements per genetic element and (2) a control enrichment value for the plurality of different non-modulating nucleic acid elements; and (d) detecting statistically significant differences between the test and control enrichment values, thereby identifying one or a plurality of genetic elements phenotypically responsive to one or a plurality of the modulating nucleic acid elements.

In some embodiments, the plurality of mammalian cells in step (a) is infected with at least 10, 15, 20, 25, 30, 35, 40, 45, 50, or more (e.g., from about 10 to about 30, about 10 to about 20, or about 20 to about 30) different modulating nucleic acid elements per genetic element. In such embodiments, each genetic element can be targeted by at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 independent modulating nucleic acid elements. In certain embodiments, the methods of the present invention comprise identifying a plurality of (e.g., at least 2, 3, 4, 5, 6, 7, 8, 9, 10, 15, 20, 25, 50, 75, or 100) genetic elements phenotypically responsive to (e.g., modulated by) one or a plurality of the modulating nucleic acid elements (e.g., a library comprising at least 10, 15, 20, 25, 30, 35, 40, 45, 50, 55, or more independent modulating nucleic acid elements that target each genetic element).

In other embodiments, the plurality of mammalian cells in step (a) is infected with at least about 25, 50, 75, 100, 250, 500, 750, 1000, 2000, 5000, 7500, 10,000, 20,000, 50,000 or more (e.g., from about 500 to about 2000, about 500 to about 1500, or about 750 to about 1250) different non-modulating nucleic acid elements. In particular embodiments, each of the non-modulating nucleic acid elements is designed to match the base composition pattern of a modulating nucleic acid element, but do not match the sequence of any human transcript.

In some embodiments, the modulating and non-modulating nucleic acid elements comprise interfering RNAs. In certain instances, the modulating nucleic acid elements target genetic elements and/or the non-modulating nucleic acid elements comprise negative control interfering RNAs that do not target genetic elements. Non-limiting examples of interfering RNAs include siRNAs, shRNAs, aiRNAs, miRNAs, Dicer-substrate dsRNAs, antisense oligonucleotides, ssRNAi oligonucleotides, RNAs directing the activity of proteins that affect genome sequence or gene expression (e.g., application of the bacterial CRISPR system), and combinations thereof. In preferred embodiments, the test and control nucleic acid elements comprise shRNAs and/or siRNAs.

In some embodiments, the modulating and non-modulating nucleic acid elements are cloned into vectors suitable for infecting mammalian cells. Examples of such vectors include, without limitation, lentiviral vectors, adenoviral vectors, retroviral vectors, adeno-associated viral (AAV) vectors, and combinations thereof.

In some embodiments, mammalian cells can be infected with vectors comprising the modulating or non-modulating nucleic acid elements using techniques known to those skilled in the art, e.g., as described in Bassik et al., *Nature Methods*, 6:443-5 (2009). In certain instances, many of the plurality of mammalian cells are infected with the same nucleic acid element. As a non-limiting example, about 50 million cells can be infected with about 50,000 nucleic acid elements such as shRNAs, such that on average, each shRNA is represented in about 1,000 cells. In particular embodiments, each cell in the plurality of mammalian cells contains one modulating or non-modulating nucleic acid element.

Any mammalian cell type can be infected in accordance with the methods of the present invention. In particular embodiments, the screening methods described herein can comprise infecting mammalian cells such as cancer cells. Examples of cancer cells include, but are not limited to, cancer cell lines derived from any type of cancer such as, e.g., K562 cells, Raji B cells, U937 cells, Jurkat cells, RPMI cells, PC9 cells, HCC827 cells, H1650 cells, H3255 cells, 11-18 cells, HeLa cells, Lncap cells, MCF-7 cells, MDA-MB-438 cells, PC3 cells, T47D cells, THP-1 cells, U87 cells, SHSYSY cells, Saos-2 cells, 721 cells, A2780 cells, A172 cells, A253 cells, A431 cells, A-549 cells, BCP-1 cells, BR 293 cells, BxPC3 cells, Cal-27 cells, COV-434 cells, CML T1 cells, DU145 cells, DuCaP cells, EM2 cells, EM3 cells, FM3 cells, H1299 cells, HT-29 cells, JY cells, Ku812 cells, KCL22 cells, KG1 cells, KYO1 cells, MCF-10A cells, MDA-MB-231 cells, MDA-MB-468 cells, MDA-MB-435 cells, MG63 cells, MONO-MAC 6 cells, Peer cells, SiHa cells, SkBr3 cells, T2 cells, T84 cells, U373 cells, VCaP cells, WM39 cells, WT-49 cells, and combinations thereof.

In certain instances, the plurality of mammalian cells in step (a) is infected at the same time in the same vessel. In certain other instances, the plurality of mammalian cells in step (a) is infected at the same time or at different times in different vessels.

A pool of infected mammalian cells (e.g., a plurality of test-infected mammalian cells and/or plurality of control-infected mammalian cells) can be selected (e.g., physically separated) based upon the presence of a detectable phenotype. Examples of such detectable phenotypes include, but are not limited to, cell growth, cell survival, reporter gene expression or induction, physical characteristics of the cell (e.g., shape, size, mass, and/or density), cell mobility or cell migration behavior, cellular appearance or morphology, and combinations thereof. In certain embodiments, the pool of infected mammalian cells (e.g., a plurality of test-infected mammalian cells and/or plurality of control-infected mammalian cells) can be selected (e.g., physically separated) by selective growth pressure and/or cell sorting based upon reporter gene expression or induction, e.g., using fluorescence-activated cell sorting (FACS).

In particular embodiments, the one or a plurality of genetic elements identified by the methods of the present invention corresponds to one or a plurality of genes such as, e.g., oncogenes that promote tumor growth and/or resistance to one or more anticancer drugs.

Non-limiting examples of oncogenes include tumor suppressor genes such as ATM, BRCA1, BRCA2, CDH1, CDKN2B, CDKN3, E2F1, FHIT, FOXD3, HIC1, IGF2R, MEN1, MGMT, MLH1, NF1, NF2, RASSF1, RUNX3, S100A4, SERPINB5, SMAD4, STK11, TP73, TSC1, VHL, WT1, WWOX, and/or XRCC1; genes with both oncogenic and tumor suppressor properties such as BCR, EGF, ERBB2, ESR1, FOS, HRAS, JUN, KRAS, MDM2, MYC, MYCN, NFKB1, PIK3C2A, RB1, RET, SH3PXD2A, TGFB1, TNF, and/or TP53; transcription factors such as ABL1, BRCA1, BRCA2, CDKN2A, CTNNB1, E2F1, ELK1, ESR1, ETS1, FOS, FOXD3, HIC1, JUN, JUNB, JUND, MDM2, MEN1, MYB, MYC, MYCN, NF1, NFKB1, PML, RARA, RB1, REL, RUNX1, RUNX3, SMAD4, STAT3, TGFB1, TNF, TP53, TP73, TSC1, VHL, WT1, and/or ZHX2; epithelial-to-mesenchymal transition genes such as BRCA2, CDKN2B, CTNNB1, ERBB2, HGF, JAK2, KIT, MCL1, NF1, RUNX3, S100A4, SMAD4, TGFB1, and/or VHL; angiogenesis genes such as AKT1, CTNNB1, EGF, ERBB2, NF1, PML, RUNX1, and/or TGFB1; apoptosis genes such as BAX, BCL2, BCL2L1, BRCA1, CASP8, E2F1, MCL1, MGMT, TNF, and/or VHL; cell adhesion genes such as APC, CDH1, CDKN2A, CTNNB1, KITLG, NF1, NF2, and/or TGFB1; cell cycle genes such as ATM, BRCA1, BRCA2, CCND1, CDK4, CDKN1A, CDKN2A, CDKN2B, CDKN3, E2F1, HGF, MEN1, STK11, and/or TP53, and combinations thereof.

In some embodiments, the pool of the plurality of test-infected mammalian cells and plurality of control-infected mammalian cells is selected based upon survival in the presence of at least one or more (e.g., a combination of) anticancer drugs. Non-limiting examples of anticancer drugs include monoclonal antibodies, tyrosine kinase inhibitors, anti-proliferative agents, chemotherapeutic agents, hormonal therapeutic agents, radiotherapeutic agents, vaccines, toxins, and combinations thereof.

Examples of monoclonal antibodies include, without limitation, trastuzumab (Herceptin®), pertuzumab (2C4), alemtuzumab (Campath®), bevacizumab (Avastin®), cetuximab (Erbitux®), gemtuzumab (Mylotarg®), panitumumab (Vectibix™), rituximab (Rituxan®), and/or tositumomab (BEXXAR®). Examples of tyrosine kinase inhibitors include, without limitation, gefitinib (Iressa®), sunitinib (Sutent®), erlotinib (Tarceva), lapatinib (GW-572016; Tykerb®), canertinib (CI 1033), semaxinib (SU5416), vatalanib (PTK787/ZK222584), sorafenib (BAY 43-9006; Nexavar®), imatinib mesylate (Gleevec®), leflunomide (SU101), vandetanib (ZACTIMA™; ZD6474), pelitinib, CP-654577, CP-724714, HKI-272, PKI-166, AEE788, BMS-599626, HKI-357, BIBW 2992, ARRY-334543, JNJ-26483327, and/or JNJ-26483327.

Exemplary anti-proliferative agents include mTOR inhibitors such as sirolimus (rapamycin), temsirolimus (CCI-779), everolimus (RAD001), BEZ235, and XL765; AKT inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl) methyl)-4-piperidinyl)-2H-benzimidazol-2-one, 10-(4'-(N-diethylamino)butyl)-2-chlorophenoxazine, 3-formylchromone thiosemicarbazone (Cu(II)Cl$_2$ complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125: 1144-1145 (2003) and Kau et al., *Cancer Cell*, 4:463-476 (2003); PI3K inhibitors such as PX-866, wortmannin, LY 294002, quercetin, tetrodotoxin citrate, thioperamide maleate, GDC-0941 (957054-30-7), IC87114, PI-103, PIK93, BEZ235 (NVP-BEZ235), TGX-115, ZSTK474, (−)-deguelin, NU 7026, myricetin, tandutinib, GDC-0941 bismesylate, GSK690693, KU-55933, MK-2206, OSU-03012, perifosine, triciribine, XL-147, PIK75, TGX-221, NU 7441, PI 828, XL-765, and WHI-P 154; MEK inhibitors such as PD98059, ARRY-162, RDEA119, U0126, GDC-0973, PD184161, AZD6244, AZD8330, PD0325901, and ARRY-142886; and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines include ANYARA from Active Biotech, DCVax-LB from Northwest Biotherapeutics, EP-2101 from IDM Pharma, GV1001 from Pharmexa, 10-2055 from Idera Pharmaceuticals, INGN 225 from Introgen Therapeutics and Stimuvax from Biomira/Merck.

Examples of radiotherapeutic agents include, but are not limited to, radionuclides such as $^{74}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Non-limiting examples of toxins include cytotoxins such as ricin, immunotoxins such as anti-CD33 monoclonal antibody-calicheamicin conjugate, anti-CD22 monoclonal antibody-*pseudomonas* exotoxin conjugate, denileukin diftitox, and combinations thereof.

In certain embodiments, the pool of the plurality of test-infected mammalian cells and plurality of control-infected mammalian cells is selected based upon reporter gene expression or induction. In certain instances, the reporter comprises a fluorescent reporter. Non-limiting examples of reporters include fluorescent proteins such as, e.g., green fluorescent protein (GFP), yellow fluorescent protein (YFP), red fluorescent protein (RFP), blue fluorescent protein (BFP), cyan fluorescent protein (CFP), Y66H, Y66F, EBFP, EBFP2, Azurite, GFPuv, T-Sapphire, Cerulean, mCFP, ECFP, CyPet, Y66W, mKeima-Red, TagCFP, AmCyan1, mTFP1, S65A, Midoriishi Cyan, S65C, TurboGFP, TagGFP, S65L, Emerald, S65T, EGFP, Azami Green, ZsGreen1, TagYFP, EYFP, Topaz, Venus, mCitrine, YPet, TurboYFP, ZsYellowl, Kusabira Orange, mOrange, Allophycocyanin (APC), mKO, TurboRFP, tdTomato, TagRFP, DsRed monomer, DsRed2, mStrawberry, TurboFP602, AsRed2, mRFP1, J-Red, R-phycoerythrin (RPE), B-phycoerythrin (BPE), mCherry, HcRedl, Katusha, P3, Peridinin Chlorophyll (PerCP), mKate (TagFP635), TurboFP635, mPlum, mRaspberry, mutants thereof, derivates thereof, and combinations thereof. In some instances, the reporter is used for affinity purification.

In other embodiments, the pool of the plurality of test-infected mammalian cells and plurality of control-infected mammalian cells is selected based upon one or more physical characteristics of the cells, such as, e.g., shape, size, mass, and/or density. In still yet other embodiments, the pool of the plurality of test-infected mammalian cells and plurality of control-infected mammalian cells is selected based upon their mobility and/or migration behavior. In further embodiments, the pool of the plurality of test-infected mammalian cells and plurality of control-infected mammalian cells is selected based upon their appearance or morphology, e.g., using a microscope-coupled cell sorting device.

In certain embodiments, the statistically significant differences between the test and control enrichment values are detected using a non-parametric statistical analysis. Examples of non-parametric statistical analyses include, without limitation, the Mann-Whitney U test, the Kolmogorov-Smirnov test, and combinations thereof. In particular embodiments, the enrichment value comprises a ratio of the frequency of a modulating nucleic acid element or a non-modulating nucleic acid element in a selected pool compared to a non-selected pool. As a non-limiting example, the logarithm of the ratio of the frequency of a modulating or non-modulating nucleic acid element in a selected pool over the frequency in a non-selected pool can be calculated to generate test and control enrichment values. In some embodiments, the differences between the test and the control enrichment values are statistically significant when the P value (e.g., obtained using a non-parametric statistical analysis) is less than 0.05 (e.g., P<0.05, P<0.01, P<0.005, etc.). In particular embodiments, the detection of such statistically significant differences enables the identification of those genetic elements that are phenotypically responsive to one or a plurality of the modulating nucleic acid elements (e.g., hit genes). See, Section below titled "Statistical Analysis for RNA interference-Based Screens" for more details on the statistical analyses used or applied in the primary screening methods of the present invention to identify one or more hit genes.

In some embodiments, the modulating and non-modulating nucleic acid elements are cloned into different vectors each comprising a unique barcode. In other embodiments, step (c) comprises quantitating the frequencies of the modulating and non-modulating nucleic acid elements by a sequencing technique such as, e.g., deep sequencing.

In another aspect, the present invention provides a method for retesting modulating nucleic acid elements selected from the primary screen above to which genetic elements were phenotypically responsive. In one embodiment, individually barcoded vectors for expression of the modulating nucleic acid elements selected from the primary screen are constructed. In some instances, these vectors are pooled for batch retesting of the RNAi phenotypes. In other instances, these vectors can be used to compare the role of the targeted genes in different cell lines, or with different selective pressures. As such, this aspect of the invention identifies one or a plurality of active modulating nucleic acid elements for the same and/or different genetic elements (e.g., hit genes). In some embodiments, a "hit" interfering RNA library is produced comprising a focused library of active interfering RNAs and negative control (NC) interfering RNAs.

In yet another aspect, the present invention provides a composition comprising one or a plurality of modulating nucleic acid elements (e.g., identified from the primary screening method described above), wherein one or a plurality of genetic elements are phenotypically responsive to one or a plurality of the modulating nucleic acid elements. In certain instances, one or a plurality of modulating nucleic acid elements selected from the primary screen are identified as active modulating nucleic acid elements based upon retesting these modulating nucleic acid elements, e.g., using batch retesting of the RNAi phenotypes. In some instances, a modulating nucleic acid element is identified as active when it inhibits the expression of the genetic element by at least 50% (e.g., at least 55%, 60%, 65%, 70%, 75%, 80%, 85%, 90% or 95%).

In certain instances, a statistical analysis (e.g., an algorithm) is used or applied to select an active modulating nucleic acid element (e.g., an effective shRNA or siRNA) from the modulating nucleic acid elements identified by the primary screen. In some instances, the statistical analyses (e.g., algorithms) for selecting an active modulating nucleic acid element based on the results of the primary screen is described in the Section below titled "Statistical Analysis for RNA interference-Based Screens".

In still yet another aspect, the present invention provides a method for identifying a first and a second modulating nucleic acid element that each independently target a first and a second genetic element, respectively, the method comprising:
  (a) cloning a first modulating nucleic acid element with a second modulating nucleic acid element to form a double-modulating vector comprising the first modulating nucleic acid element linked to the second modulating nucleic acid element, wherein the first modulating nucleic acid element targets a first genetic element and the second modulating nucleic acid element targets a second genetic element;
  (b) repeating step (a) using a plurality of different first modulating nucleic acid elements and a plurality of different second modulating nucleic acid elements, thereby forming a plurality of different double-modulating vectors;
  (c) infecting a plurality of mammalian cells with the plurality of different double-modulating vectors, thereby forming a plurality of double-modulating vector-infected mammalian cells;
  (d) separating a selected pool of the plurality of double-modulating vector-infected mammalian cells expressing a detectable phenotype from a non-selected pool of the plurality of double-modulating vector-infected mammalian cells not expressing the detectable phenotype; and
  (d) quantitating the frequencies of the first modulating nucleic acid element linked to the second modulating nucleic acid element in the selected pool relative to the frequencies of the first modulating nucleic acid element linked to the second modulating nucleic acid element in the non-selected pool, thereby identifying a first and a second modulating nucleic acid element that target a first and a second genetic element.

Non-limiting examples of modulating nucleic acid elements, genetic elements, mammalian cells, and vectors that are suitable for use in the secondary screen of the present invention are described above.

In certain embodiments, the secondary screening method further comprises:
(1) cloning a first non-modulating nucleic acid element with a second non-modulating nucleic acid element to form a double-non-modulating vector; and/or
(2) cloning the first or second modulating nucleic acid element with a non-modulating nucleic acid element to form a mixed-modulating/non-modulating vector.

In one particular embodiment, the method further comprises:
(a) cloning a first non-modulating nucleic acid element with a second non-modulating nucleic acid element to form a double non-modulating vector comprising the first non-modulating nucleic acid element linked to the second non-modulating nucleic acid element, wherein the first non-modulating nucleic acid element and the second modulating nucleic acid element do not target a genetic element;
(b) repeating step (a) using a plurality of different first non-modulating nucleic acid elements and a plurality of different second non-modulating nucleic acid elements, thereby forming a plurality of different double non-modulating vectors;
(c) infecting a plurality of mammalian cells with the plurality of different double non-modulating vectors, thereby forming a plurality of double non-modulating vector-infected mammalian cells;
(d) separating a selected pool of the plurality of double non-modulating vector-infected mammalian cells expressing a detectable phenotype from a non-selected pool of the plurality of double non-modulating vector-infected mammalian cells not expressing the detectable phenotype; and
(e) quantitating the frequencies of the first non-modulating nucleic acid element linked to the second non-modulating nucleic acid element in the selected pool relative to the frequencies of the first non-modulating nucleic acid element linked to the second non-modulating nucleic acid element in the non-selected pool.

In certain instances, the frequencies of the first and second non-modulating nucleic acid elements in the selected pool and/or non-selected pool are compared to the frequencies of the first and second modulating nucleic acid elements.

In another particular embodiment, the method further comprises:
(a) cloning the first or second modulating nucleic acid element with a first non-modulating nucleic acid element to form a mixed-modulating/non-modulating vector comprising the first or second modulating nucleic acid element linked to the first non-modulating nucleic acid element, wherein the first non-modulating nucleic acid element does not target a genetic element;
(b) repeating step (a) using a plurality of different first or second modulating nucleic acid elements and a plurality of different first non-modulating nucleic acid elements, thereby forming a plurality of different mixed-modulating/non-modulating vectors;
(c) infecting a plurality of mammalian cells with the plurality of different mixed-modulating/non-modulating vectors, thereby forming a plurality of mixed-modulating/non-modulating vector-infected mammalian cells;
(d) separating a selected pool of the plurality of mixed-modulating/non-modulating vector-infected mammalian cells expressing a detectable phenotype from a non-selected pool of the mixed-modulating/non-modulating vector-infected mammalian cells not expressing the detectable phenotype; and
(e) quantitating the frequencies of the first or second modulating nucleic acid element linked to the first non-modulating nucleic acid element in the selected pool relative to the frequencies of the first or second modulating nucleic acid element linked to the first non-modulating nucleic acid element in the non-selected pool.

In certain instances, the frequencies of the first or second modulating nucleic acid element and the first non-modulating nucleic acid element in the selected pool and/or non-selected pool are compared to the frequencies of the first and second modulating nucleic acid elements. Such dual vectors containing one modulating nucleic acid element targeting a hit gene linke to one non-modulating (e.g., negative control) nucleic acid element can be tested to confirm or validate the individual phenotype of the modulating nucleic acid element.

In some embodiments, step (a) comprises cloning all of the pairwise combinations of (1) two or more modulating nucleic acid elements that each target a first genetic element, (2) two or more modulating nucleic acid elements that each target a second genetic element, and (3) one or a plurality of non-modulating nucleic acid elements, to form a plurality of vectors containing all pairwise combinations of the modulating and non-modulating nucleic acid elements.

In other embodiments, the modulating and/or non-modulating nucleic acid elements are cloned into a vector in any order to form one of the modulating vectors, non-modulating vector, or mixed-modulating/non-modulating vectors described herein. In certain instances, the first modulating nucleic acid element is upstream of and linked to the second modulating nucleic acid element, or vice versa. In other instances, the first or second modulating nucleic acid element is upstream of and linked to the first non-modulating nucleic acid element, or vice versa. In yet other instances, the first non-modulating nucleic acid element is upstream of and linked to the second non-modulating nucleic acid element, or vice versa.

Figure 10:
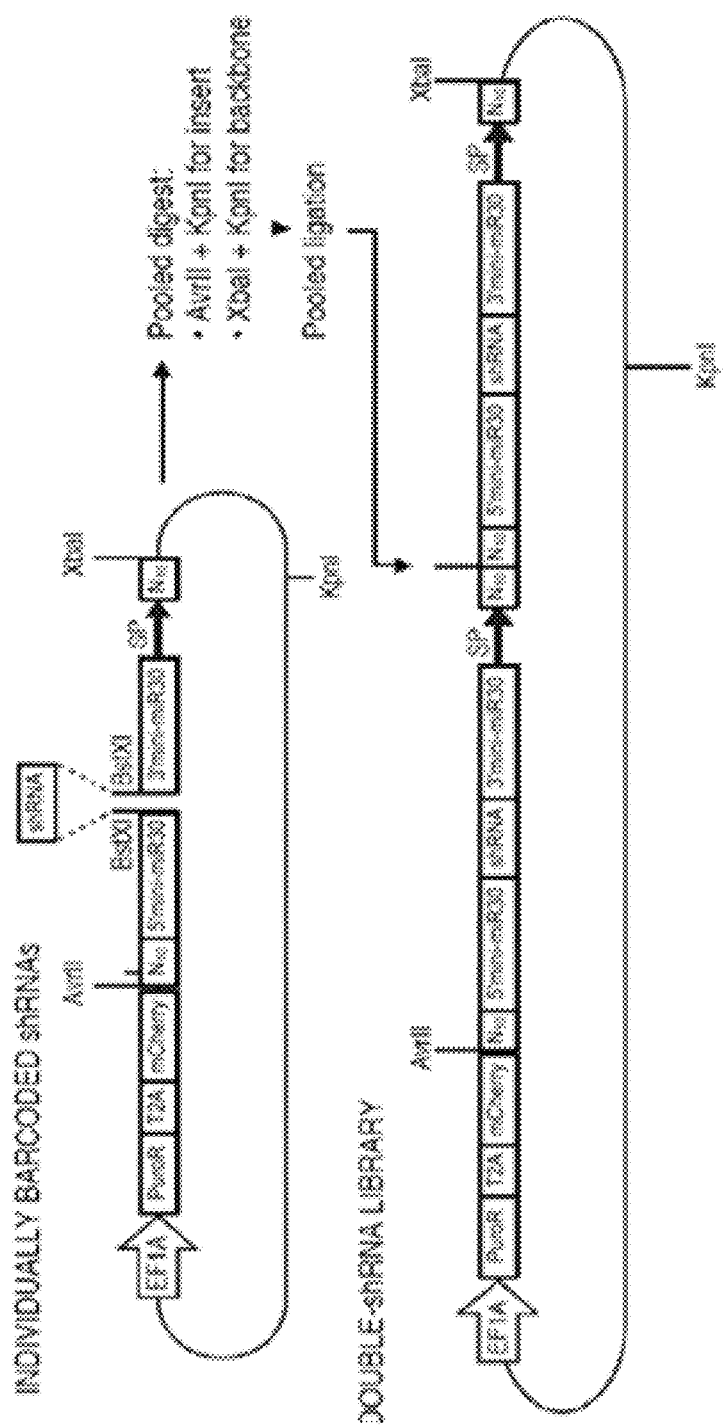
FIG. 10 illustrates an exemplary strategy for the creation and monitoring of barcoded double-shRNA constructs.

In some embodiments, the modulating and/or non-modulating nucleic acid elements are cloned into a vector such as the lentiviral expression vector described in Example 1 and depicted in FIG. 10 to form the vectors set forth herein (e.g., double-modulating vectors, double-non-modulating vectors, and/or mixed-modulating/non-modulating vectors).

In other embodiments, the method further comprises:
detecting differences between the frequencies of the first modulating nucleic acid element linked to the second modulating nucleic acid element in the selected pool relative to a calculated control frequency, thereby identifying a genetic interaction between the first and second genetic elements.

In some instances, the calculated control frequency comprises a control phenotype based at least in part on a demonstrated independent effect of the first modulating nucleic acid element on the detectable phenotype and/or a demonstrated independent effect of the second modulating nucleic acid element on the detectable phenotype. In certain instances, the control frequency is calculated from the individual frequencies or phenotypes for the first and second modulating nucleic acid elements.

In some embodiments, the genetic interaction corresponds to a buffering genetic interaction or a synergistic genetic interaction. In certain embodiments, the presence of a synergistic genetic interaction indicates that the first and second genetic elements act in parallel pathways. In some instances, the first genetic element and second genetic element act synergistically, e.g., to promote tumor growth and/or resistance to one or more anticancer drugs. In other embodiments, the presence of a buffering genetic interaction indicates that the first and second genetic elements act in a linear pathway.

In certain embodiments, the present invention provides a method for conducting a secondary screen for identifying a genetic interaction between at least 3, 4, 5, 6, 7, 8, 9, 10, or more of the genetic elements identified by the primary screen, wherein step (a) comprises cloning a plurality of (e.g., a first, second, third, fourth, fifth, etc.) modulating nucleic acid elements to form a vector that comprises the plurality of modulating nucleic acid elements linked to each other within the vector.

In some embodiments, a statistical analysis (e.g., an algorithm) is used or applied in the secondary screening methods of the invention to identify a genetic interaction between two hit genes. In some instances, the statistical analyses (e.g., algorithms) for identifying a genetic interaction between two hit genes based on the results of the secondary screen is described in the Section below titled "Statistical Analysis for RNA interference-Based Screens".

In yet other embodiments, the method further comprises screening the vectors set forth herein (e.g., double-modulating vectors, double-non-modulating vectors, and/or mixed-modulating/non-modulating vectors) for different phenotypes and/or in different cell lines.

In still yet other embodiments, the vectors set forth herein (e.g., double-modulating vectors, double-non-modulating vectors, and/or mixed-modulating/non-modulating vectors) comprise (1) a unique barcode for each of the modulating and non-modulating nucleic acid elements or (2) a combinatorial barcode that detects both nucleic acid elements cloned into the vectors. In further embodiments, step (e) comprises quantitating the frequencies of the nucleic acid elements cloned into the vectors set forth herein by a sequencing technique such as deep sequencing.

In yet another particular embodiment, the method (e.g., step (a)) further comprises:
(1) cloning a first modulating nucleic acid element with a second modulating nucleic acid element and a third modulating nucleic acid element to form a triple-modulating vector comprising the first modulating nucleic acid element linked to the second and third modulating nucleic acid elements, wherein the first modulating nucleic acid element targets a first genetic element, the second modulating nucleic acid element targets a second genetic element, and the third modulating nucleic acid element targets a third genetic element; and/or
(2)(i) cloning the first, second, or third modulating nucleic acid element with two different non-modulating nucleic acid elements to form a first type of a triple-mixed-modulating/non-modulating vector comprising the first, second, or third modulating nucleic acid element linked to the two different non-modulating nucleic acid elements, and/or (ii) cloning two of the first, second, or third modulating nucleic acid elements with a non-modulating nucleic acid element to form a second type of a triple-mixed-modulating/non-modulating vector comprising two of the first, second, or third modulating nucleic acid elements linked to the non-modulating nucleic acid element; and/or
(3) cloning three different non-modulating nucleic acid elements to form a triple-non-modulating vector comprising a first, second, and third non-modulating nucleic acid element.

In certain embodiments, the method (e.g., step (a)) further comprises cloning four, five, six, seven, eight, nine, ten, or more different combinations of modulating nucleic acid elements and/or non-modulating nucleic acid elements into the same vector to form a vector that comprises all of the nucleic acid elements linked to each other within the vector.

In certain aspects, the present invention provides a set of tools and/or services to take hit genes identified from a primary RNAi screen and explore their genetic interactions using epistasis maps. In certain instances, the functions of uncharacterized genes can be described by examining their genetic interactions using the methods of the invention. In other instances, targets of drugs can be identified by evaluating the pattern of interactions with other genes in the epistasis map using the methods of the invention. In certain other instances, on-target versus off-target effects of nucleic acid elements such as shRNAs can be determined by examining the genetic interaction patterns when knocking down a gene. As a non-limiting example, shRNAs targeting a single intended gene should have correlated patterns of genetic interaction, but may exhibit a distinct pattern if they target additional genes with functional consequences.

In some embodiments, the data analysis strategy and statistical analyses (e.g., algorithms) described herein can be the basis of software that enables users to interpret primary screen data to identify hit genes and to select nucleic acid elements such as shRNAs for subsequent secondary screens (e.g., double-shRNA screens). In certain instances, the software enables users to analyze data from the secondary screen to quantify genetic interactions and to assemble and understand an epistasis map. In certain other instances, the genetic interaction maps obtained and generated using the methods of the present invention are used to predict functional associations between genes and/or to identify drug targets for therapy such as combination cancer therapy. As non-limiting examples, such genetic interaction maps will enable the identification of novel target genes for therapeutic intervention, enable the elucidation of the mechanism of action of small molecule therapeutics, and/or enable rational design of combination therapies based on the inhibition of two or more target genes.

In particular embodiments, the methods of the present invention provide a pattern of interactions serving as a phenotypic signature for each drug which could be used to identify its target, as well as functionally related pathways in the cell. In some instances, the methods described herein enable a systematic interrogation of cooperating factors as they impact a disease process. As such, in certain embodiments, the present invention provides primary screening tools for identifying hit genes and active interfering RNAs that target those hit genes, as well as secondary screening tools for generating RNAi-based genetic interaction maps that enable a functional understanding of associations between the hit genes.

IV. Statistical Analysis for RNA Interference-Based Screens

In certain aspects, one or more of the statistical analyses (e.g., algorithms) described herein can be used in the methods of the present invention for accurately identifying genetic elements (e.g., hit genes) from an RNAi-based primary screen, for selecting active and/or effective modulating nucleic acid elements (e.g., interfering RNAs such as shRNAs) based on the primary screen, and for enabling quantitative genetic interaction mapping based on the secondary screen using constructs comprising multiple modulating nucleic acid elements. This section describes the use of shRNAs for purposes of example only, as other interfering RNAs can also be used in the methods of the present invention.

A. Strategy for the Accurate Detection of Hit Genes from the Primary Screen

Accurate detection of hit genes from RNA-interference-based screens is a formidable challenge, as evidenced by the fact that three screens for HIV host factors carried out by different laboratories reported lists of hit genes that had little overlap (Bushman et al., *PLoS Pathog.*, 5:e1000437 (2009)). The challenge in identifying hit genes from genome-wide RNA interference screens is the fact that many shRNAs do not sufficiently knock down their target transcript, and that shRNAs can knock down transcripts other than the transcript they were designed to target. To overcome the common issues of false-positive and false-negative results, the exemplary statistical analyses (e.g., algorithms) of the invention for the detection of hit genes from the primary screen take advantage of two design features of the genome-wide shRNA libraries described herein:

1. Each human gene is targeted by a large number (on average ~25) of independent shRNAs.
2. Each sublibrary contains a large number (on average ~1,000) of negative control shRNAs.

Negative control shRNAs can be designed as follows: candidate shRNA sequences can be created by choosing a nucleotide for each position randomly from a probability distribution that matched the distribution of nucleotide frequencies at that position in the shRNAs designed to target genes within the same sublibrary. shRNA sequences can be accepted as negative controls if neither the guide strand nor the passenger strand matched any sequence in the human transcriptome with less than 3 mismatches.

Based on the primary screen, an enrichment value (ratio) comprising a quantitative phenotype can be calculated for each shRNA. In the simplest case, the logarithm of the ratio of the shRNA frequency in the treated cell pool over shRNA frequency in the untreated cell pool can be calculated. A quantitative framework has also been developed that takes into account the differential growth of the treated and untreated cell pool to allow the derivation of a quantitative phenotype metric that is independent of experimental parameters such as the duration of the screen.

The median of the distribution of phenotypes for the negative controls is taken to reflect the behavior of wild-type (WT) cells. The deviation of negative control shRNAs from this WT phenotype reflects both random noise in any stage of the screening, sample preparation and sequencing procedure, as well as unpredicted effects of negative control shRNAs on actual hit genes. Since both noise and off-target effects also affect the phenotypes of shRNAs designed to target specific transcripts, the distribution of negative control shRNA phenotypes provides the null distribution from which a set of shRNAs targeting a hit gene needs to deviate in a statistically significant way. The p-value for each gene is the probability for the set of phenotypes of shRNAs targeting this gene to have been randomly drawn from the set of phenotypes of the negative control shRNAs. Suitable statistical tests to calculate this p-value include the two-sample Kilmogorov-Smirnov test and the Mann-Whitney U test. To correct for multiple-hypothesis testing in the genome-wide data set, the positive false discovery rate can be controlled Storey et al., *Proc. Natl. Acad. Sci. USA*, 100:9440-9445 (2003)) and a q-value cutoff chosen to determine the genome-wide set of statistically significant hit genes.

In certain embodiments, to enhance the signal-to-noise ratio of the phenotype measurements, the primary screen can be conducted as two independent replicates and the two phenotype values obtained for each shRNA can be averaged before performing the statistical analysis. Furthermore, the screening protocol can be designed to prevent population bottlenecks at any point in the screen, since such bottlenecks increase sampling (Poisson) noise. Good results can be obtained when maintaining a population size that was at least 1,000-fold larger than then number of unique shRNAs in the sublibrary.

The approach described herein has several advantages compared with alternative approaches:

1. If a library lacking negative control shRNAs was used, statistical tests could be applied by comparing the set of shRNA phenotypes for each gene to the set of shRNA phenotypes from the entire sublibrary. The drawback of this approach is that the set of all shRNAs does not represent a true null distribution, since it contains active shRNAs against hit genes. The presence of a large number of strong hit genes would therefore reduce the statistical significance assigned to a weaker hit gene, potentially classifying it as non-hit. The same weaker hit gene may have been classified as a hit gene if it had been tested in the context of a sublibrary containing few other hits. Since sublibraries are organized by biological function, it is likely that for a given screen, some sublibraries will contain many more hit genes than others. In the absence of negative control shRNAs, this would result in false-negative calls. By contrast, the present method compares each gene to a large set of negative control shRNAs, and will thus calculate a p-value for each gene that is independent of the presence of other hit genes in the same sublibrary.
2. A common practice in the literature is the use of "hard cut-offs", either for the phenotype (e.g., only shRNAs with at least two-fold enrichment are taken into account) or for the fraction of shRNAs with a given phenotype (e.g., a gene counts as a hit if at least 75% of the shRNAs targeting the gene are enriched). The problem with these approaches is that the first type of cutoff penalizes genes that are true biological hits but that have a weak phenotype, and that the second type of cutoff penalizes genes that are true biological hits, but for which not many active shRNAs are present in the sublibrary—either by chance, or because the transcript has intrinsic sequence or secondary structure properties that make it difficult to target by RNA interference. The present approach minimizes false-negatives by avoiding hard-cutoffs, and sensitively detects weak hits based on the overall pattern of shRNA phenotypes, even if the deviation from the negative control phenotype distribution is subtle.

Figure 4:
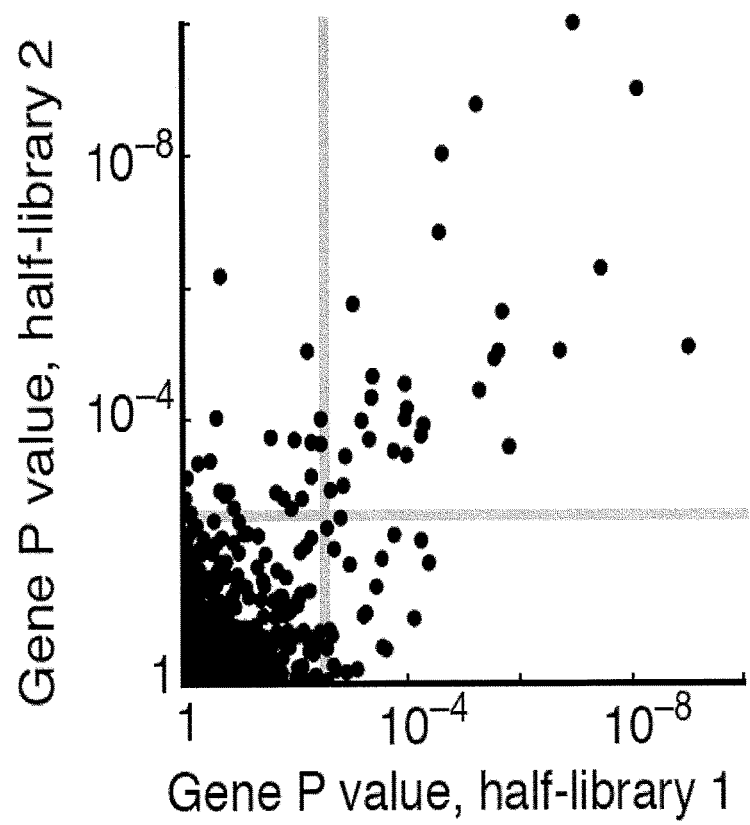
FIG. 4 illustrates that similar p-values were found for 1,000 genes that were targeted by two independent libraries.

The present approach was validated by creating two shRNA libraries that were designed to target the same set of 1,000 human genes. Each gene was targeted with 50 shRNAs in each library, and the two libraries used completely independent shRNAs. Screens were carried out in parallel, and the two p-values calculated for each gene based on the two libraries correlated well, indicating that the present approach detected hits based on their underlying biology, rather than based on technical artifacts inherent to a specific library design (see, FIG. 4).

B. Strategy for the Selection of Individual Effective shRNAs Based on the Primary Screen As described above, the present analysis of the primary screen data reveals the hit genes that are involved in the biological process of interest. To further characterize the effect of knocking down these hit genes, and to map genetic interactions between hits, individual constructs for the expression of individual shRNAs targeting these genes can be generated. For this purpose, a subset (generally 3) of shRNAs can be chosen from the set (about 25 on average) of shRNAs targeting the hit gene in the genome-wide library.

For strong hit genes, there are typically a large number of shRNAs with observed phenotypes very different from the negative control shRNA phenotypes in the primary screen. The phenotype of such strongly active shRNAs is generally very reproducible once the shRNA construct is individually tested in cells.

The statistical analyses (e.g., algorithms) of the present invention for the analysis of primary screens also detects weaker hit genes, for which the overall distribution of shRNA phenotypes is significantly shifted from the negative control phenotype distribution, but for which few (if any) individual shRNAs have a phenotype that deviates dramatically from the WT phenotype. In such cases, the challenge is to pick shRNAs for individual use based on the primary screen data. As a result, the statistical analyses (e.g., algorithms) of the present invention were developed to minimize the false-positive rate during the selection of shRNAs based on the primary screen results. Based on a large set (>1,000) of shRNAs for which the phenotype was determined using a highly reproducible batch retest protocol, the parameters that are predictive of active shRNAs were identified empirically. Using logistic regression, a quantitative score was determined as a predictor of shRNA activity. This score incorporates information on shRNA sequence, the phenotype measured in the primary screen, the number of counts observed in the untreated sample of the primary screen, and the p-value of the corresponding hit gene. The predictor performs very well with an ROC of 0.91 (see, FIG. 8).

C. Strategy for Quantitative Genetic Interaction Mapping Based on Double-shRNA Screens Secondary screens can be carried out using a double-shRNA library consisting of combinations of active shRNAs against hit genes from the primary screen. Phenotypes can be quantified for each pairwise combination of shRNAs. Several (typically 12) negative control shRNAs can be included, such that the phenotype of double-shRNAs containing a negative control shRNA in combination with an active shRNA reflects the individual phenotype of the active shRNA (see, FIG. 12). Thus, the experimental design allows quantification of the phenotype of single shRNAs and double shRNAs in the same pooled experiment.

In certain embodiments, genetic interactions can be defined as the deviation of the observed double-mutant phenotype from the phenotype expected for the combination of two given single-mutant phenotypes. As predicted on theoretical grounds and on the basis of previous studies, the majority of gene pairs do not show large interactions, and the typical double-mutant phenotypes for a given first shRNA depend linearly on the phenotype of the second shRNA. Thus, the expected double-shRNA phenotype for each pair of shRNAs can be defined empirically by a linear fit of double-shRNA phenotypes including the shRNAs of interest, and the genetic interaction can be defined as a distance of the observed phenotype from the expected phenotype.

In some embodiments, to reduce experimental noise, double shRNA screens can be carried out in duplicate, and double-shRNA phenotypes can be calculated as the averages of the two screens and the two permutations in which the two shRNAs occur in double-shRNA constructs.

In other embodiments, to obtain a measure of interaction between genes that is robust with respect to partial off-target effects of shRNAs, 3 independent shRNAs against each hit gene can be included in double-shRNA screens. If these shRNAs have partial off-target effects, it is extremely unlikely that the off-target effects would all affect the same off-target transcript. In yet other embodiments, to reduce the impact of off-target driven genetic interaction values for double-shRNAs on resulting genetic interaction maps, a genetic interaction score can be calculated by incorporating both the median genetic interaction value of the 9 double-shRNA phenotypes and the standard deviation of the 9 values. The resulting score reflects both the magnitude and the confidence of the genetic interaction, adapting a strategy previously developed for genetic interaction maps in yeast (Collins et al., *Genome Biol.*, 7:R63 (2006)). shRNAs with a genetic interaction pattern that does not correlate with the genetic interaction patterns of other shRNAs targeting the same gene to a sufficient degree can be excluded from the analysis, on the basis that their effect is likely to be mediated to a large degree through off-target genes (see, FIG. 23).

V. Examples

The following examples are offered to illustrate, but not to limit, the claimed invention.

Example 1. RNA Interference-Based Genetic Interaction Maps

This example illustrates embodiments of the present invention for conducting an RNAi-based primary screen to identify hit genes and for conducting secondary screens using double RNAi constructs to knock down all pairwise combinations of the hit genes identified from the primary screen, thereby identifying genetic interactions between these hit genes to predict functional associations between genes and identify drug targets for therapy.

1. Design of Ultra-Complex shRNA Libraries for Primary Genome-Wide Screens

An ultra-complex shRNA library targeting each protein-coding gene in the human genome with ~25 independent shRNAs on average was designed (FIG. 1). The library was divided into 9 sublibraries containing 55,000 shRNAs each. The shRNA sequences were designed using several algorithms and also incorporated shRNA sequences known to be efficacious.

Each sublibrary contains a set of ~1,000 negative control shRNAs, which were designed to match to the base composition pattern of the transcript-targeting shRNAs in the sublibrary, but which do not match the sequence of any human transcript. The negative control shRNAs are an important feature for the statistical analysis of primary screens, as detailed in Section 3 below.

Oligonucleotides encoding the shRNAs for each sublibrary were synthesized by Agilent Technologies as oligonucleotide microarrays, amplified and cloned into a lentiviral vector following a strategy described in Bassik et al., *Nat. Methods* 6(6): 443-5 (2009). The vector used for genome-wide screens incorporates features that were optimized for the specific applications described herein. The vector encodes in a single transcript puromycin resistance to allow selection of infected cells, mCherry to allow monitoring of expression of the transcript by flow cytometry, and the shRNA in a mir30 context. Expression of this transcript is driven by the EF1A-promoter, allowing robust constitutive expression in all (or most) human cell types.

2. Design of Pooled Genome-Wide Primary Screens

Figure 2:
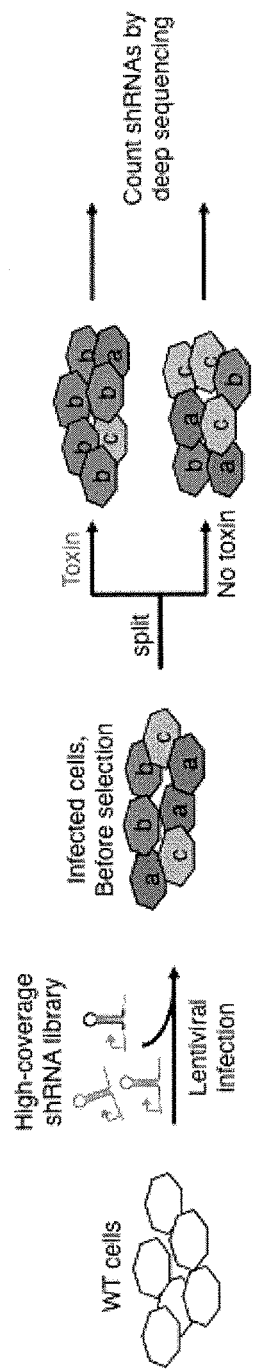
FIG. 2 illustrates an example of a workflow for a pooled primary screen of the invention.

The purpose of the primary screen is to identify genes that play a role in a biological process of interest. One approach (FIG. 2) is to introduce ultra-complex shRNA libraries into human cells via lentiviral infection. Infection is carried out at a low multiplicity of infection in order to minimize the integration of multiple shRNAs into the genome of an individual cell. Infected cells are then enriched by mild puromycin selection followed by recovery from puromycin treatment. The pool of infected cells is split and one sub-pool is subjected to a relevant selective pressure, whereas the other sub-pool is grown under standard conditions. The selective pressure can be implemented as a treatment that kills a fraction of cells or slows cell growth, or as a fluorescence activated cell sorting protocol in which a population of cells is selected based on the level of a fluorescent reporter. The extent of selective pressure is carefully chosen to avoid creating population bottlenecks, which would increase sampling noise in the distribution of shRNAs in the cell pool. Preferably, continuous mild selection or repeated rounds of mild selection and recovery are used to maintain a large population size throughout the experiment (corresponding to 1,000 cells per shRNA in the library). At the conclusion of the selection protocol, genomic DNA is isolated from the treated and untreated cell populations, the shRNA-encoding genomic DNA segment is amplified and the frequency of shRNAs in the two populations is determined using deep sequencing as described in, e.g., Bassik et al., Nat. Methods 6(6): 443-5 (2009).

3. Detection of Significant Hits from the Primary Screen

Figure 3:
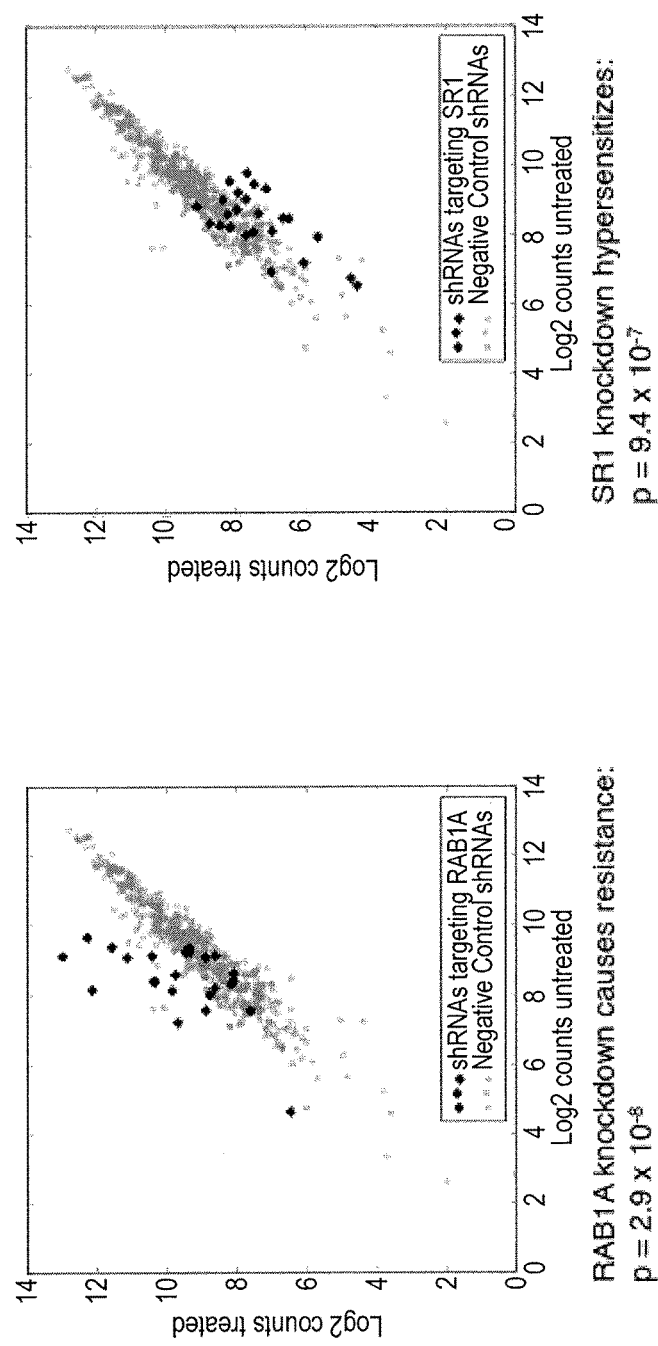
FIG. 3 illustrates an example of statistically significant hit genes that are based on the enrichment or disenrichment of shRNAs targeting one gene compared to the distribution of enrichment or disenrichment of negative control shRNAs.

The challenge in identifying hit genes from genome-wide RNA interference screens is the fact that many shRNAs do not sufficiently knock down their target transcript, and that shRNAs can knock down transcripts other than the transcript they were designed to target. The ultra-complex shRNA libraries described herein aim to minimize the resulting issues of false-negative and false-positive results by targeting each gene with a large number of independent shRNAs. A separate issue is caused by noise in the shRNA count data caused by Poisson sampling. The algorithm of the invention for the detection of hit genes compares the enrichment or disenrichment of the shRNAs designed to target a gene of interest with the distribution of enrichment and disenrichment that is observed for the 1,000 negative control shRNAs to detect statistically significant differences (FIG. 3).

The approach described herein was validated by creating two shRNA libraries that were designed to target the same set of 1,000 human genes; each gene was targeted with 50 shRNAs in each library, and the two libraries used completely independent shRNAs. Screens were carried out in parallel, and the two p-values calculated for each gene based on the two libraries correlated well (FIG. 4), indicating that this approach detected hits based on their underlying biology, rather than based on technical artifacts inherent to a specific library design.

Figure 5:
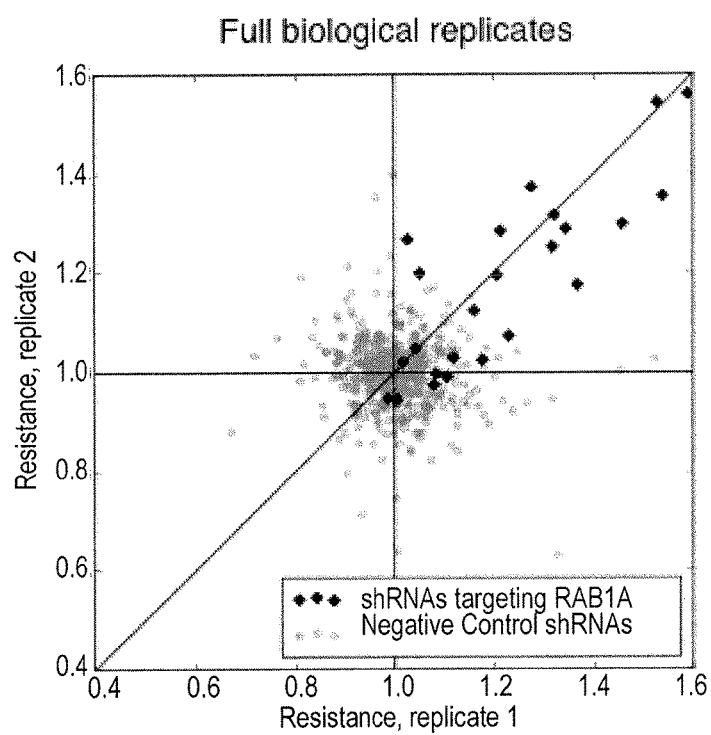
FIG. 5 illustrates the reproducibility of primary screen phenotypes.
Figure 6:
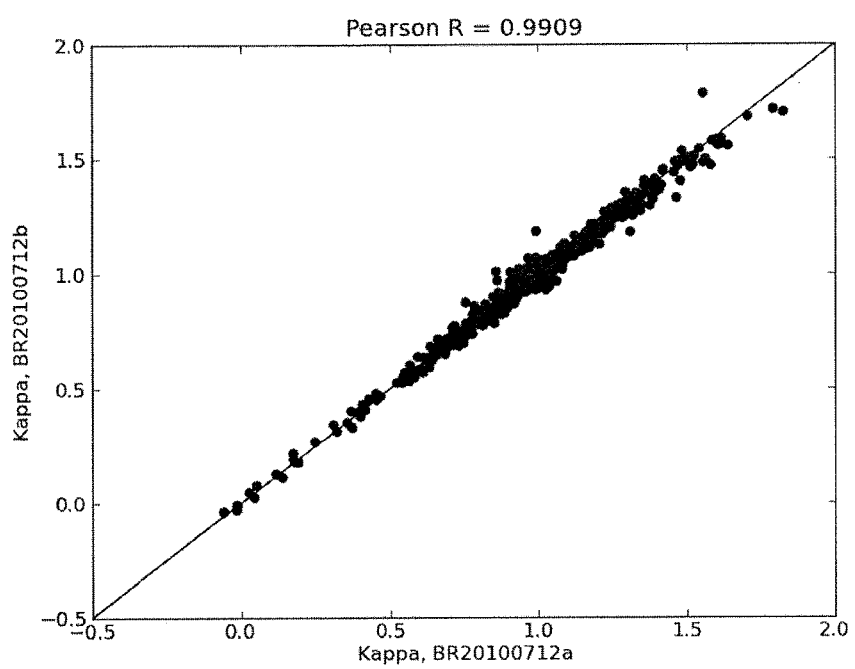
FIG. 6 illustrates the highly reproducible quantification of phenotypes by pooled retesting of shRNAs.
Figure 7:
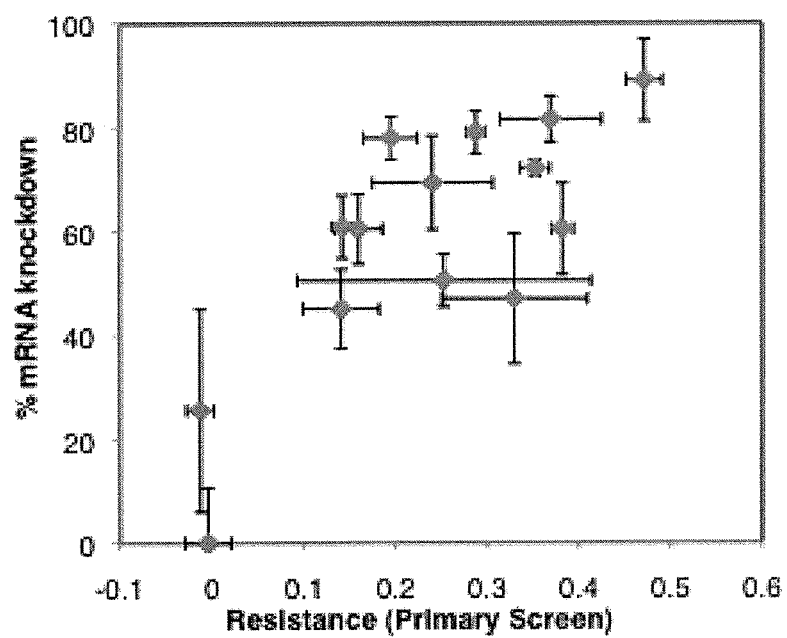
FIG. 7 illustrates the % knockdown of the RAB1A transcript as quantified by quantitative PCR compared to the phenotype from the primary screen for shRNAs targeting RAB1A.

4. Selection and Validation of Active shRNAs Targeting Significant Hit Genes from the Primary Screen In order to quantify genetic interactions between hit genes from the primary screen, 3 active shRNAs against each hit gene are chosen. For strong hit genes, reproducibility of the quantitative phenotype from the primary screen is usually sufficient to pick active shRNAs (FIG. 5). Lentiviral vectors expressing individual shRNAs are cloned, and a pool of several hundred such shRNAs is tested in human cells, using the same selection protocol as in the primary screen. Such pooled retest experiments yield highly reproducible phenotypes (FIG. 6), thus providing a gold standard for shRNA activity. It has been confirmed for selected target transcripts that shRNA phenotypes in the screen correlate broadly with the extent of target transcript knockdown by the shRNA (FIG. 7).

Figure 8:
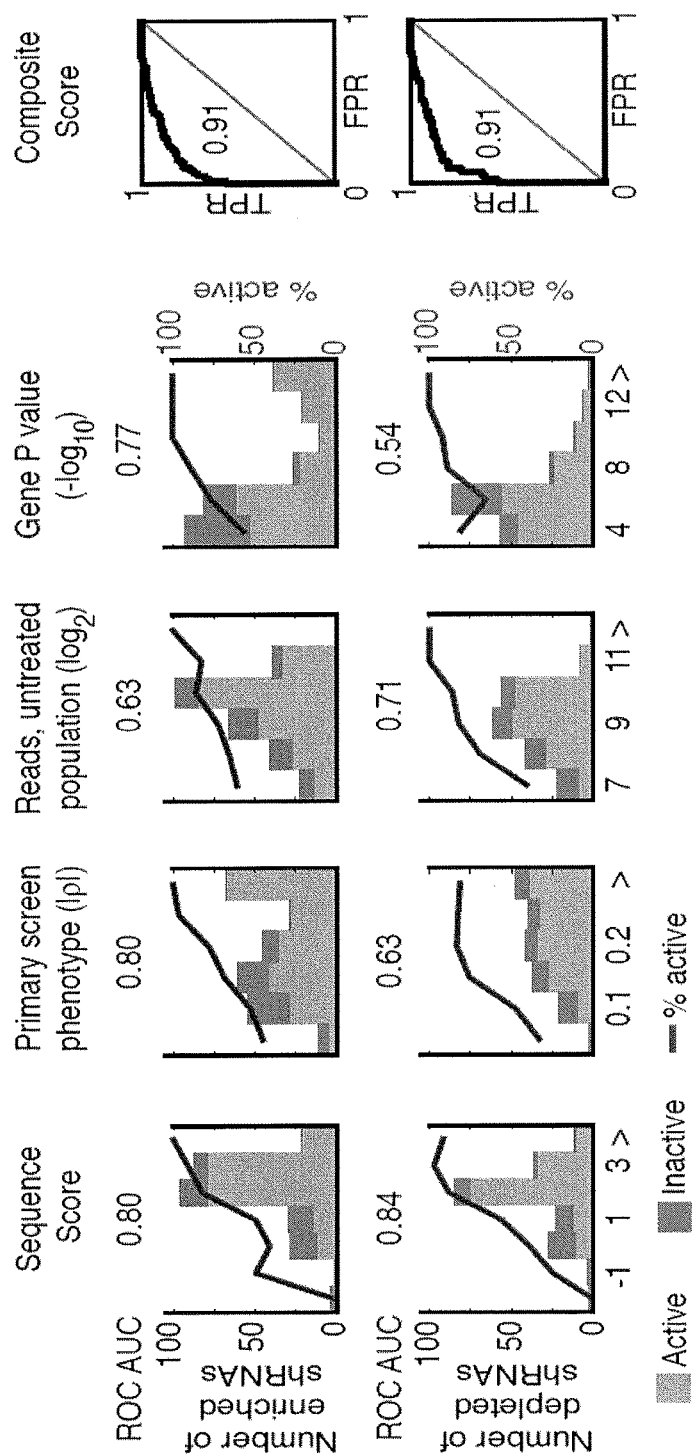
FIG. 8 illustrates an example of the ROC curves for a quantitative predictor of shRNA activity that were developed based on data from the primary screen and sequence properties.

In order to guide selection of active shRNAs for weaker hits, a quantitative predictor of shRNA activity was empirically developed based on shRNA performance in the primary screen, shRNA sequence, and shRNA count numbers in the raw deep sequencing data. This predictor was developed based on the pooled retest validation of hundreds of shRNAs chosen from a primary screen. The predictor performs very well (FIG. 8).

5. Production and Screening of a Barcoded Double-shRNA Library

Figure 9:
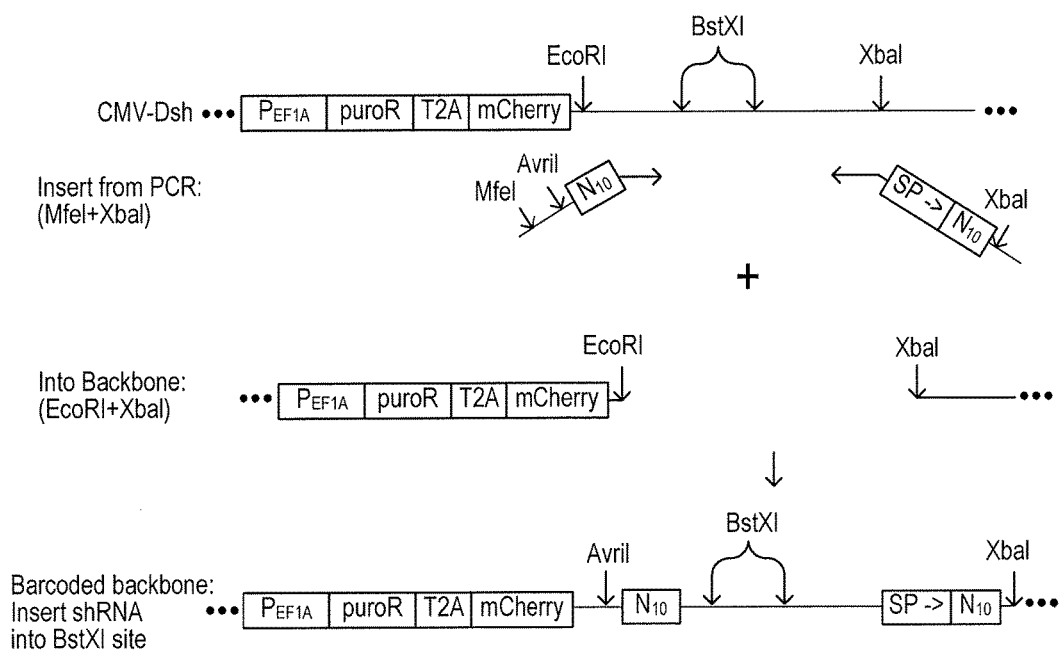
FIG. 9 illustrates the creation of a vector containing random 10-basepair barcodes upstream of a BstXI site, into which individual shRNAs are inserted.

When plasmids containing individual shRNAs targeting hit genes are created, 10-basepair barcode sequences are introduced upstream and downstream of the shRNA of interest. Barcodes are created using randomized oligonucleotides (FIG. 9), and barcodes are accepted if they are more than one substitution away from any other previously accepted barcode.

The vector into which individual shRNAs are inserted is designed to enable rapid creation of all pairwise combinations of shRNAs in a lentiviral double-shRNA expression vector (FIG. 10). Plasmids encoding all shRNAs of interest, as well as negative control shRNAs, are pooled. The amount of each plasmid is calculated based on the previously observed shRNA phenotype to optimize representation of the shRNA in both selected and unselected samples upon completion of a screen of the double-shRNA library. The plasmid pool is then split and digested with different combinations of restriction enzymes. Specific fragments are isolated from each pool and ligated to obtain a double-shRNA plasmid pool containing all pairwise combinations of shRNAs of interest. Human cells are infected with the double-shRNA library, and a selection protocol is carried out as for the primary screen. In order to quantify the frequency of each double-shRNA in the selected and unselected cell populations, genomic DNA is isolated from the cells and a region containing the downstream barcode from the first shRNA and the upstream barcode of the second shRNA of the second shRNA is amplified and subjected to deep sequencing. This experimental design circumvents the amplification and sequencing of shRNA-encoding DNA, which avoids the introduction of sequencing bias, and obviates the need to sequence a long segment of DNA to identify both shRNAs in a double-shRNA construct.

6. Systematic Mapping of Genetic Interactions Based on the Double-shRNA Screen

Figure 11:
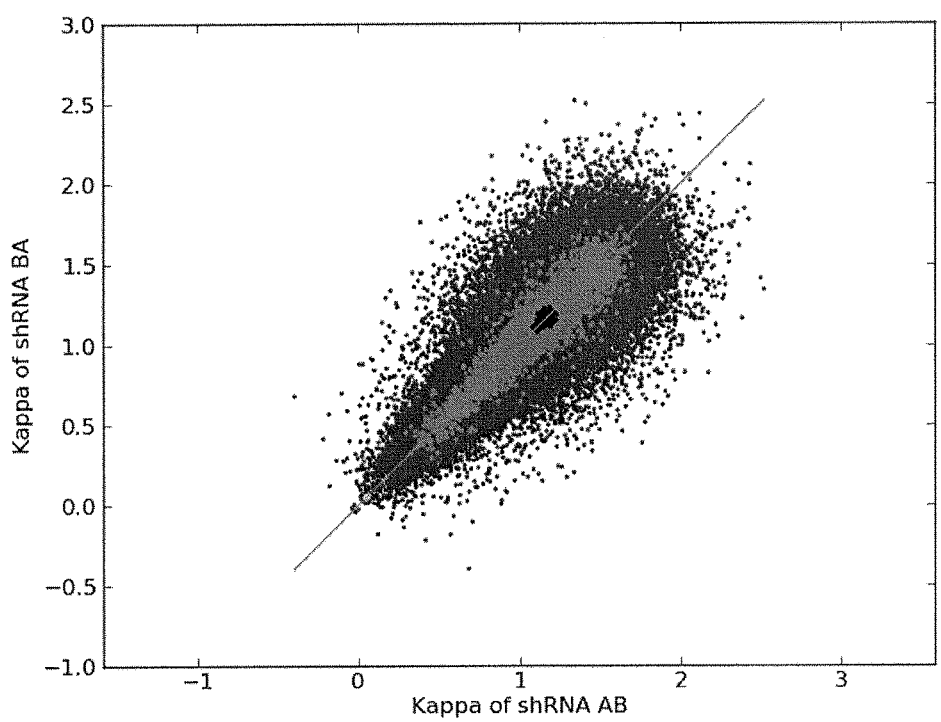
FIG. 11 illustrates a comparison of double shRNA phenotypes for pairs of shRNAs A, B in the orientation AB and BA. Black: two negative controls; light grey: negative control+shRNA against hit; dark grey: two shRNAs against hits.
Figure 12:
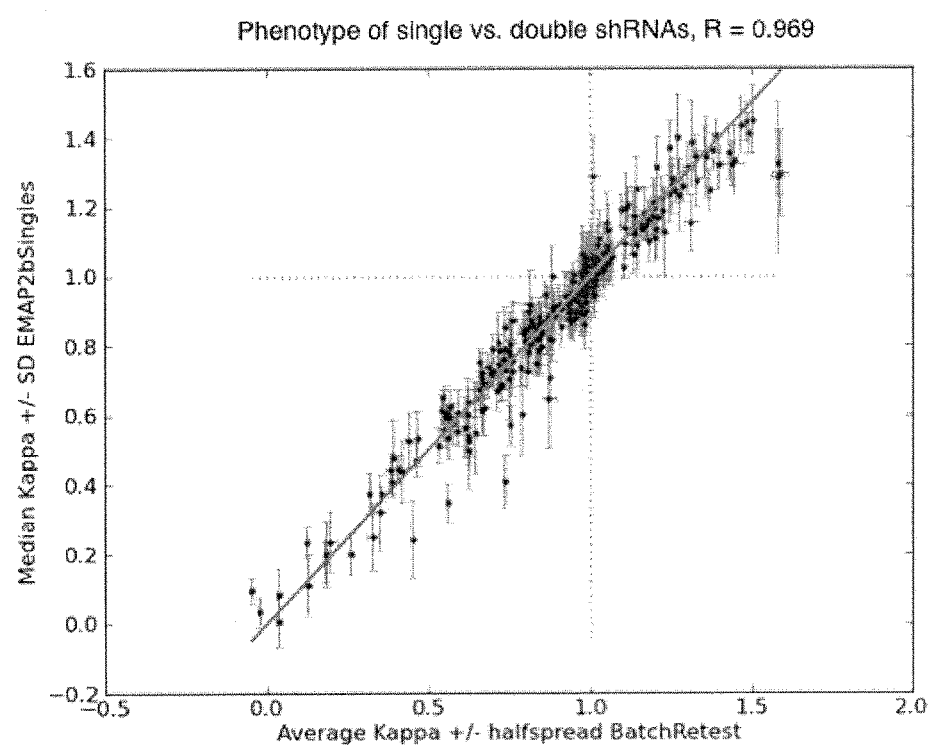
FIG. 12 illustrates shRNA phenotypes from pooled retesting versus from shRNA+negative control double-shRNA constructs from a double-shRNA screen of the invention.

Double-shRNA screens give reproducible results. An internal measure of noise is the comparison of the phenotype of a double-shRNA composed of shRNAs A and B in the order AB with the activity of the double shRNA BA. The good correlation between AB and BA double-shRNA phenotypes validates this approach (FIG. 11). Double shRNAs containing one shRNA targeting a hit gene and one negative control shRNA provide a measure of the phenotype of the hit shRNA. This design allows quantification of the phenotype of single shRNAs and double shRNAs in the same pooled experiment. It has been established that the phenotype of individual shRNAs is maintained in the double-shRNA construct (FIG. 12).

Genetic interactions between each pair of shRNAs are calculated as deviations from the typical double-shRNA phenotype for shRNAs with the given individual phenotypes. Genetic interactions between each pair of genes are calculated from the nine pairwise shRNA interactions between the 3 shRNAs targeting one gene and the 3 shRNAs targeting the other gene. For the final genetic interaction score, the variability of shRNA-based values is taken into account, such that the score reflects both the magnitude and the confidence of the genetic interaction, adapting a strategy previously developed for genetic interaction maps in yeast (see, Collins et al., *Genome Biol.* 7(7): R63 (2006)).

Example 2. RNAi Screening Platform for the Rational Development of Polytherapies Against Cancer This example illustrates application of the RNAi-based screening methods of the present invention for the rational development and design of polytherapies for the treatment of cancer.

Currently, enormous volumes of data are being generated by the comprehensive molecular characterization of a number of human tumors. The ability to effectively and efficiently use RNAi to assess the biologic consequences of gene target inhibition is of critical importance to understanding gene function and to uncover tumor-specific vulnerabilities. The identification of tumor-specific vulnerabilities provides rationale for the development of biologically-based targeted therapies. RNAi screening is a powerful technology for high-throughput gene function discovery that has been used to identify tumor-specific vulnerabilities.

However, there are significant limitations to the RNAi screening resources that are currently available. The RNAi screening tools used to date do not efficiently target the full compendium of cancer relevant genes due to technological limitations in genome coverage and RNAi gene knockdown efficacy. These technological limitations also lead to false-positive and false-negative screen hits. Thus, currently available RNAi screening platforms are not cost-effective for performing high-throughput screens for most labs. This example presents technologies and resources that overcome these limitations, dramatically improving RNAi screening capabilities. The screening methodologies described herein take advantage of statistically-based analyses and the power of new deep sequencing technologies that are being rapidly democratized. These new approaches will greatly facilitate the development of cancer polytherapies, opening a new paradigm for rationally-based cancer therapeutics that fully capitalize on genomic profiling of human tumors.

In order to design effective combination cancer therapies (e.g., polytherapies), the signaling pathways that act synergistically to promote tumor growth or therapeutic resistance must first be identified. This knowledge then enables the design of therapies that target these key cancer "driver" pathways. A major obstacle to the development of therapies that preclude or overcome resistance to targeted cancer therapy is that there is no systematic means by which to identify pathways that functionally cooperate and synergize to drive tumor growth or therapeutic resistance. Therefore, the search for effective cancer polytherapies has been done largely in an ad hoc manner exploring only a very limited number of potential combinations. The key to rationally designing an optimal combination of therapies lies in the systematic identification of pathways that, when targeted, lead to specific and synergistic destruction of cancer cells. The approaches described herein can determine simultaneously and rapidly (within 1-3 weeks) high precision measures of functional genetic interactions between large numbers (typically 100,000) pairs of shRNAs that target genes of interest in the context of any cancer. This represents a transformative technology in terms of the ability to systematically uncover cancer-relevant gene interaction networks that drive tumor growth, and that potentially can be exploited as rational, tumor-specific polytherapies.

Specific genetic alterations promote the initiation and maintenance of many human cancers. Moreover, synergistic interactions among genetic alterations found in human tumors can drive not only tumor growth but also therapeutic resistance in patients. A comprehensive understanding of the functional relationships underlying synergistic gene interactions in human cancers is lacking. This example describes a novel strategy that greatly increases the ability to identify genetic interactions (relationships) that functionally cooperate to promote tumor growth and therapeutic resistance. This strategy utilizes the next-generation shRNA screening platform of the invention to identify and validate cancer drivers, and quantitative genetic interaction maps to delineate the functional relationships between these drivers that will allow for rational and more effective combination therapies.

Greatly Improved RNAi Screening Platform.

RNAi technology has the tremendous potential of extending forward genetics and quantitative genetics approaches to mammalian cells. In practice, however, biological and experimental issues have hampered this potential. In particular, the low efficacy of many shRNAs can lead to false-negative results, and off-target effects can lead to false-positive results. Thus, RNAi screens have fallen into one of two categories: either genome-wide, but qualitative; or quantitative, but focused on a subset of genes.

Two key technologies have been leveraged to develop an approach for highly quantitative RNAi-based genome-wide screens: (1) highly parallel microarray-based oligosynthesis, enabling production of massive shRNA libraries; and (2) deep sequencing technology that makes it possible to monitor simultaneously the phenotypic consequences of each shRNA in such highly complex libraries. shRNA libraries were introduced into mammalian cells by pooled lentiviral infection and subjected to selection. Changes in the frequencies of each shRNA are then quantified by deep sequencing (see, Bassik et al., *Nat. Methods* 6(6): 443-5 (2009)).

This example describes a dramatic improvement to this approach, establishing an integrated platform for RNAi-based screens that combines a unique genome-wide library design, optimized protocols for minimization of experimental noise and a complete software suite for statistical data analysis that allows detection of significant hit genes and active shRNAs. Construction of an ultra-complex shRNA library that targets each human gene with about 25 independent shRNAs has been completed. Such ultra-complex libraries overcome both the common problems of high false-negative rates and high false-positive rates. The high-coverage libraries described herein maximize the chances of effectively targeting each gene with multiple independent shRNAs, and allows rigorous evaluation of the probability that shRNAs act through the intended target gene. The library includes a large number of matched negative-control shRNAs that allow testing the statistical significance of hit genes against a background of noise and off-target effects.

Importantly, one can confidently identify not only genes that confer resistance to a selective pressure, but also genes that further sensitize cells.

In a pilot genome-wide experiment, the RNAi screening methods of the present invention were applied to identify genes that would render human cells either resistant or hypersensitive to the toxin ricin when targeted by active shRNAs. The 179 hit genes identified in this genome-wide primary screen show remarkable specificity: ~80% of hits were in pathways implicated in ricin trafficking and action. The top ~50% most statistically significant hits were all involved in trafficking. 20 previously uncharacterized genes were discovered.

Figures 13A, 13B:
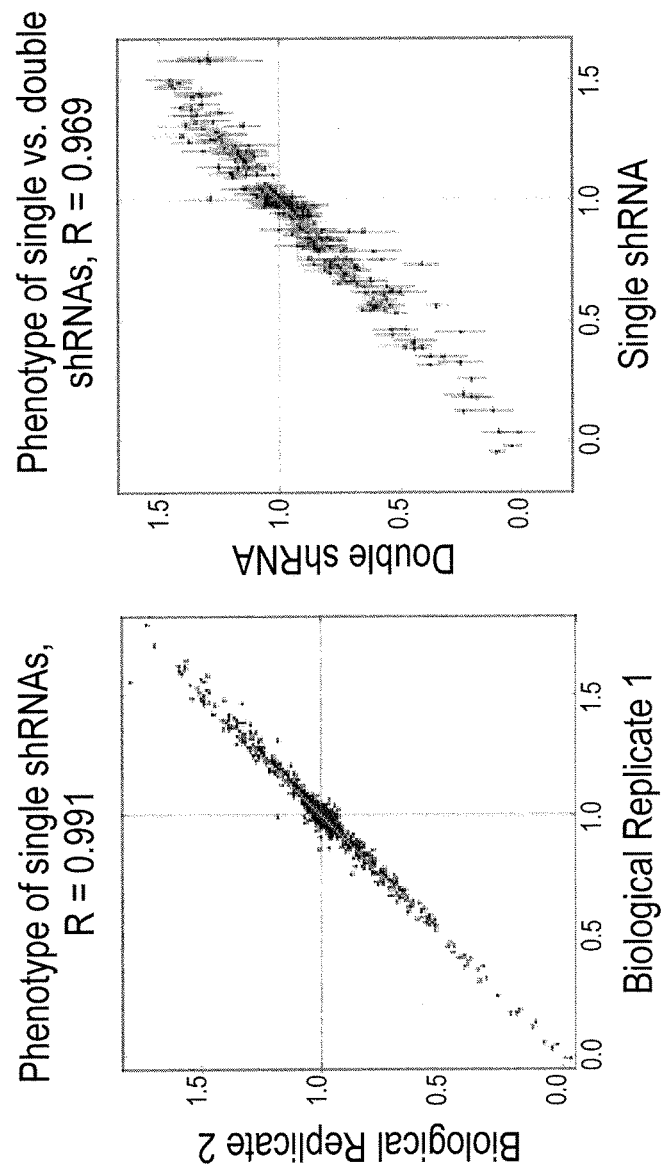
FIGS. 13A-B illustrate the reproducibility of shRNA phenotypes as single- and double-shRNA constructs. (A) Single-shRNA phenotypes obtained from two independent experiments. (B) For double shRNAs, phenotypes of the same single shRNAs in combination with different negative control shRNAs were quantified; average phenotypes and error bars denoting the standard deviation for combinations with 10 different negative control shRNAs are shown.

The methods described herein not only allow the identification of relevant genes, but also of effective shRNAs against those hit genes. Quantitative phenotypes of individual shRNAs are highly reproducible using the optimized screening protocols described herein (FIG. 13A). Validated shRNAs are valuable tools for further research, in particular, for genetic interaction mapping strategies outlined below. This platform can be used to identify shRNAs targeting various cancer drivers, as well as the genes they depend upon for transformation and continued growth.

Quantitative Genetic Interaction Maps Define Functional Relationships Between Cancer Drivers.

The improvements in quantitative precision described above are a prerequisite for the reliable measurements of genetic interactions. A major obstacle in large-scale genetic interaction studies is the fact that the number of interactions increases as the square of the number of genes. The present inventors have pioneered a strategy that allows the rapid determination of genetic interaction by creating double-shRNA libraries through pooled ligation of validated shRNAs for the use in pooled screens. Importantly, it has been discovered that the activity of the individual shRNAs is maintained in the double-shRNA constructs (FIG. 13B). By coupling this to a deep sequencing readout, it is possible to rapidly and with high precision measure the phenotypic impact of at least 100,000 different pairs in a single small-scale experiment. This represents a transformative advance, both in terms of the precision and the depth of coverage, over previously described shRNA platforms.

Notably, the RNAi screening technology described herein enables the systematic and quantitative exploration of the functional relationships between genes relevant both to cancer biology and sensitivity to targeted therapy. As discussed below, applications may include the construction of unique libraries and systematic genetic interaction maps, the identification of modifiers of driver mutations and/or mutations identified in The Cancer Genome Atlas (TCGA), and the systematic characterization of function and functional relationships between components identified either through primary screens or the TCGA efforts. More broadly, the ability to characterize a huge number of combinations of lesions will provide fundamental insight into cancer biology and dramatically improve the ability to identify potential synergistic targets for rational polytherapy.

Production of Genetic Interaction Maps to Uncover Pathway Relationships Between Cancer Drivers.

The Weissman laboratory has pioneered the development of integrated sets of experimental and computational strategies that make it possible to measure and analyze high-density genetic interaction maps (e.g., pairwise descriptions of the extent to which the loss of one gene will aggravate or buffer the effect of the loss of a second one). This work, which initially focused on microorganisms including the budding yeast Saccharomyces cerevisiae and the fission yeast Schizosaccharomyces pombe, has led to a string of fundamental biological insights. As described below, a pooled lentiviral shRNA approach has been optimized that now makes it possible to conduct similar systematic, high precision, quantitative genetic interaction maps in mammalian cells. This approach makes it possible to determine simultaneously and rapidly (on the ~2 week timescale) high precision measures of functional/genetic interactions between large numbers (typically about 100,000 pairs) of shRNAs. This represents a transformative technology in terms of the ability to systematically define gene functions in an objective and automated manner and, thus, to search for genetic interactions that enable the rational design of effective polytherapy strategies.

This example illustrates the use of the screening methodology of the invention to systematically identify pathways that when compromised magnify the effects of targeted therapies. In certain embodiments, the unbiased whole-genome searches described herein may provide a critical complement to more focused candidate-based strategies.

Non-limiting examples of model systems include hematologic cancers such as CML caused by the BCR-ABL translocation and non small cell lung cancers (NSCLC) resulting from mutations in EGFR. In addition to providing critical insights into these two important cancer drivers, this study is readily generalizable and as such will provide a roadmap for the rational design of a wide range of targeted combination therapies.

Background Quantitative Genetic Interaction Maps as a Tool for Interrogating Biological Systems.

Classically, genetic interactions describe relationships between two single mutants affecting a single phenotype such as growth (FIG. 14A). Quantitative measurements can classify distinct types of these interactions as either: (1) aggravating (synthetic sick/lethal), as is seen when two genes act in parallel pathways to support a critical process; or (2) buffering, where the phenotype of the double mutant is no worse than either of the single mutants, often indicating a linear pathway or protein complex (FIG. 14B).

When performed systematically, these modifier screens yield a phenotypic signature for each gene, which is a rich set of information consisting of the pattern of interactions with all other genes (FIG. 14C). Genes can then be clustered based upon the similarity of their phenotypic signatures. This unbiased and automated approach can reveal remarkably specific functional information. For example, functions of novel genes or drugs can be defined by the similarity of their phenotypic signature to that of known genes. In addition to these functional insights, such maps reveal the functional dependencies and pathway relationships of genes.

Applied to cancer models, the strategy described herein will yield a number of transformative findings. Quantitative measurements of knockdown phenotypes in a primary screen combined with robust statistical analysis will identify new players in these pathways, as well as effective shRNAs that can be used to target them. Genetic interaction maps will yield a comprehensive set of modifiers (positive and negative) for factors involved in cancer development/progression. Most importantly, these maps will show the spectrum of functional partners for a given oncogene/tumor suppressor, providing a roadmap for combination therapies.

Description of Mammalian Double-shRNA Platform.

While the potential value of genetic interaction maps in mammalian systems is clear, the effective construction of such maps face two compounding technical challenges: the numbers of pairs are huge and the individual measurements have to be precise/quantitative in order to determine interactions. In principle, RNAi-based approaches allow the systematic targeting of any gene. However, off target effects and the low efficacy of many targeting interference RNAs has substantially limited their utility for systematic quantitative genetic approaches. Thus far it has been possible either to do a focused screen on subsets of candidates or qualitative screens with extensive validation. These approaches can find some of the major players but are not suited for the quantitative comprehensive requirements for genetic interaction (GI) maps.

Two technological advances enabled the present inventors to overcome these challenges and now allow the construction of mammalian GI maps rapidly and with high precision. High-density, high-fidelity oligonucleotide synthesis has enabled the creation of ultra high-coverage shRNA libraries (~25 shRNAs/gene) (see, Bassik et al. (2009)). These libraries solve many of the false positive and false negative problems that plague current RNAi libraries, which often do not have sufficient numbers of shRNAs to either effectively target genes or rule out off-target effects. At the same time, the ability to quantitatively measure the abundance of hundreds of millions of shRNAs simultaneously is made possible by deep sequencing. This extraordinary capacity enables the huge increase in measurement required as the phenotypes of pairs of shRNAs are systematically interrogated (described below).

The experimental strategy of the present invention for genetic interaction mapping comprises two stages. In the first stage, a genome-wide primary screen is conducted. High-coverage shRNA libraries targeting each human gene with ~25 independent shRNAs are introduced into human cells via pooled lentiviral infection. The cell population is subjected to a relevant selective pressure, such as a chemotherapeutic, toxin or expression/knockdown of a cancer-relevant gene, whereas a control population of cells remains untreated. shRNA frequencies in treated and untreated populations are quantified by deep sequencing to identify shRNAs that make cells either resistant or hypersensitive to the selective agent. Using this experimental approach, shRNA phenotypes quantified in this way are highly reproducible. The precision is at least as high as that obtained for microorganisms, which is a crucial prerequisite for quantitative genetic studies.

The library design as described herein, in combination with novel algorithms of the invention, allow the rigorous identification of statistically significant hit genes. In particular, the fact that every gene is targeted by many (25 or more) distinct shRNAs makes it possible to rigorously eliminate spurious signals from off target effects. In the second stage (outlined in FIG. 15), active shRNAs against hit genes from the primary screens are identified and ligated as a pool to create a double-shRNA library with all pairwise combinations of shRNAs. This approach allows for the rapid creation of large double-mutant libraries for pooled screens and thus facilitates combinatorial genetics on a massive scale. Importantly, it has been found that the activity of the individual shRNAs is maintained in the double-shRNA constructs. Phenotypes are quantified for all combinations of shRNAs, and genetic interactions are calculated. Genes can then be clustered based on their patterns of genetic interaction to identify pathways and functional units. In a pilot screen, consistent phenotypic signatures were observed for independent shRNAs targeting the same gene, and it was possible to dissect functional differences between protein isoforms, as well as striking examples of synergy (FIG. 16). It is precisely these types of rare synergistic pairs that provide promising candidates for polytherapy approaches.

Application to BCR-ABL-Driven Tumors.

The clinical success of Abl TKIs (e.g., imatinib, dasitinib, etc.) is a remarkable triumph for the principle of targeting specific cancer drivers. Yet, resistance to Abl TKI treatment remains a problem in a number of settings, such as in patients with the Abl T315I secondary resistance mutation and in patients with Ph+ALL. Thus, there is a strong need to identify genes acting synergistically with BCR-ABL to promote leukemia cell growth to identify companion targets whose inhibition might enhance response to Abl TKI treatment or preclude the development of secondary treatment resistance. For a number of practical reasons, the BCR-ABL driven, imatinib-sensitive cell line K562 can be used to apply the comprehensive genetic interaction map to cancer biology. There have been a number of published screens to identify single modifier shRNAs that confer resistance of K562 cells to imatinib, providing a benchmark for the primary screens. Results from test primary screens for single shRNA that modify K562 imatinib sensitivity have been very encouraging. For example, consistent with previous results, it was found in an unbiased screen that PTPN1 knockdown causes imatinib resistance with a very strong statistical significance ($P=6\times10^{-6}$). Importantly, a number of other, strong unpublished hits in these screens was found including genes that when knocked down specifically sensitize K562 cells to imatinib. The identification of sensitizing hits is technically more challenging than finding resistance genes and is directly relevant to efforts to find targets for combination therapies. As such, a genome-wide modifier screen can be performed and a pairwise genetic interaction screen with the hits from the initial screen can be conducted in accordance with the screening methods described herein.

The results from this genetic interaction map and the double shRNA libraries generated will also provide a foundation for efforts to expand the understanding of modifiers of Abl inhibitors to other relevant systems. For example, Ph+ ALL cell lines such as Su-Ph2 and SU/SR are particularly attractive because of the relatively rapid development of imatinib resistance in this disease. Another attractive area would be the exploration of resistance and sensitization mechanism in cells directly derived from patients. Druker and coworkers recently described an elegant "proof of principle" experiment for such efforts in which they explored primary leukemia cell lines for sensitivity to knock down of tyrosine kinase inhibitors. It is likely that such primary cell screens would not allow for the very large numbers needed for the de novo construction of genetic interactions maps. However, once the much smaller set of pairs of shRNAs has been identified that act synergistically with each other, these pairs could then be tested in primary cells. Similarly, it will be possible to conduct screens on limited shRNA libraries of high value hits and pairs of hits in an in vivo setting. More broadly, the screening approach described herein can be combined with a bootstrapping strategy in which the most comprehensive and precise screens are performed in the most amenable relevant systems. These insights and reagents can then be used to study increasingly sophisticated systems.

Genome-Wide Identification of Genetic Modifiers of EGFR Kinase Inhibitor Response in Lung Cancer.

Figure 17:
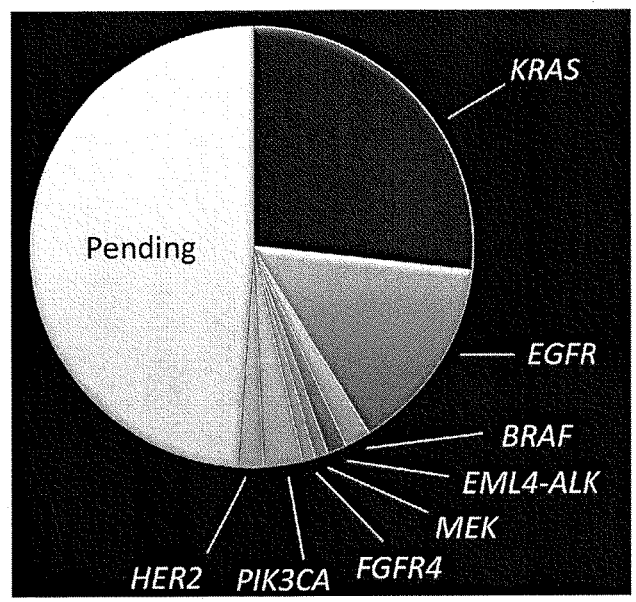
FIG. 17 illustrates the spectrum of recurrent somatic oncogenic mutations in human non-small cell lung cancers. Recurrent somatic mutations have not yet been identified in approximately 50% of lung cancer specimens ("pending").

The successful use of targeted cancer therapy is based on the identification and therapeutic exploitation of specific genetic alterations that drive the growth of human tumors. These genetic alterations consist of activating mutations or gene rearrangements in oncogenes, including many kinases, which "drive" tumor growth by promoting tumor cell survival and subverting tumor cell death. Examples of "oncogenic drivers" include BCR-ABL in chronic myeloid leukemia, mutant BRAF in melanoma, and mutant epidermal growth factor receptor (EGFR), the EML4-ALK (anaplastic lymphoma kinase) gene rearrangement, mutant BRAF and others in lung cancer, the leading cause of cancer mortality in the US (FIG. 17). In some genetically defined subsets of cancer patients whose tumors harbor an oncogenic driver (e.g., BCR-ABL, mutant EGFR), pharmacologic oncogene inhibition has become the standard of care. The personalized cancer medicine paradigm is exemplified by the efficacy of EGFR tyrosine kinase inhibitor (TKI) treatment in patients with lung cancers that harbor activating mutations in the kinase domain of EGFR (e.g., L858R, Exon 19 deletion). Treatment with the EGFR TKI erlotinib causes tumor regression in many EGFR-mutant lung cancer patients without significant systemic toxicity. Similarly, treatment with the ALK TKI crizotinib results in tumor regression in lung cancer patients whose tumors harbor the EML4-ALK gene fusion without major systemic toxicity. The ability of oncogene inhibition to selectively kill tumor cells indicates that an oncogenic driver such as mutant EGFR or ALK confers upon tumor cells a state of oncogene dependence (addiction) that does not exist in non-transformed cells.

Despite the impressive clinical success of EGFR TKI or ALK TKI treatment, responses in lung cancer patients are heterogeneous and resistance invariably develops. Similarly, responses are incomplete in patients with BRAF-mutant tumors treated with the BRAF kinase inhibitor PLX4032. A significant obstacle to the optimal use of these and other targeted cancer therapies is the lack of a coherent strategy to develop appropriate combinations that will enhance response rates and prevent resistance. The large number of drugs and targets available today preclude a purely empiric, mix-and-match approach.

To overcome this obstacle, the systematic quantitative genetic approach described herein will be applied to highly relevant cell line models of lung cancer to define rational combination therapeutic strategies that may enhance responses to targeted cancer therapy in lung cancer patients. As proof-of-principle of this approach, a focused RNA interference screen in human lung cancer cell lines was performed to test the hypothesis that EGFR TKI treatment responses in EGFR-mutant lung cancer patients are heterogeneous as a result of genetic modifiers that determine the degree to which tumor cells are dependent on mutant EGFR and thus their sensitivity to EGFR kinase inhibitor treatment. NF-κB was identified as a novel genetic modifier of EGFR oncogene dependence that promotes EGFR TKI resistance in EGFR-mutant lung cancer cell lines and patients. These findings identified NF-κB and EGFR as rational companion drug targets and provide rationale for testing combined pharmacologic inhibition of NF-κB and EGFR in selected EGFR-mutant lung cancer patients.

Building on the success of using focused RNAi screening to study mutant EGFR oncogene dependence, a next-generation functional genomics-based strategy can be used to comprehensively identify genetic determinants of mutant EGFR oncogene dependence in lung cancer. The hypothesis that unknown genetic modifiers determine the degree to which lung cancers are dependent on mutant EGFR and thus the extent to which they are sensitive to EGFR TKI treatment can be tested. The strategy described herein capitalizes on highly evolved high throughput RNAi screening technologies that enable genome-wide individual or double RNAi knockdown of genes of interest. A key aspect of the screening methods of the invention is the ability of double RNAi screening to identify genetic interaction networks that are based upon complex and non-intuitive functional relationships among components of cancer-relevant signaling pathways.

Specifically, it is an aim to identify genes that when silenced increase or decrease the sensitivity (i.e., $IC_{50}$) of EGFR-mutant human lung cancer cell lines to treatment with the EGFR TKI erlotinib. Importantly, it has been shown that several established EGFR-mutant human lung cancer lines grow well in culture, accurately model the response of EGFR mutant lung cancer patients to erlotinib treatment, and are genetically tractable using RNAi approaches. Genome-wide screens can be performed in an established human lung cancer cell line, PC9, that harbors one of the two most frequent somatic activating mutations in the EGFR kinase domain, an in-frame exon 19 deletion. Those gene combinations that when knocked down synergistically alter sensitivity to erlotinib can be identified. Following the initial screen in PC9 cells, the effects of knocking down each of the initial screen hits on erlotinib sensitivity can then be studied in other highly relevant EGFR-mutant human lung cell lines including: HCC827 and H1650 cells that, like PC9, express the EGFR exon 19 deletion mutant, and in H3255 and 11-18 cells that harbor the EGFR L858R mutation, the other major clinically-relevant EGFR activating kinase domain mutation found in lung cancer patients. Screen hits can be prioritized for further validation and mechanistic studies using relevant EGFR-mutant lung cancer tumor models and can also be clinically cross-validated using appropriate human lung cancer clinical specimens. Together, these studies will provide comprehensive insight into the genetic determinants of mutant EGFR oncogene dependence and identify potential rational combination therapeutic strategies that may enhance responses to EGFR TKI treatment in EGFR-mutant lung cancer patients. Additionally, both the shRNA libraries generated and the insight into biological pathways are applicable to other cancers involving mutations in EGFR family members, such as lung, breast, head and neck, glioma, and colon. These studies also serve as a model for developing novel rational companion therapeutic targets in patients with other oncogene-driven cancers for which responses to oncogene inhibition are sub-optimal.

Although these studies focus on gain of function cancer driver mutations, the tools described herein can be used to identify genes that are synthetically lethal in the context of loss of function tumor suppressor mutations. Since tumor suppressor mutations have traditionally been less "druggable", tumor suppressor synthetic lethal screens could identify novel therapeutic strategies for cancers that harbor these mutations in the absence of a "druggable" canonical driver mutation (e.g., ovarian carcinomas, doi:10.1038/nature10166).

Double-shRNA Genetic Interaction Libraries.

In order to study functional interactions between identified genes, a number of double-shRNA genetic interaction libraries (est. 15-20) is created. In general, libraries will focus on the top ~100 hits from a given screen. Since 3 shRNAs per gene is included, there will be ~300×300 shRNAs, or roughly 90K double-shRNA species per library. Inclusion of negative controls raises this number to approximately 100K double shRNA pairs per library.

A ligation-based approach has been technically validated to construct the double shRNA libraries of the invention, and it has been demonstrated that these libraries can be readily made, and that each pair of shRNAs can knock down 2 genes simultaneously while preserving the individual phenotype of the single shRNA. In some embodiments, the double shRNA vectors can be directly synthesized.

Example 3. Exemplary RNAi-Based Mammalian Genetic Interaction Maps

An ultra-complex shRNA library targeting each protein-coding gene in the human genome with ~25 independent shRNAs on average was designed (FIG. 1). The library was divided into 9 sublibraries containing ~55,000 shRNAs each. The shRNA libraries of the invention have at least the following advantages: (1) many shRNAs per gene address false negative and false positive problems; (2) rapid screening using shRNA pool vs. multiwell plates; (3) high fidelity oligonucleotides enable direct cloning and use of library (~1 week); and (4) highly adaptable means that one can easily change design to incorporate different promoters, improved shRNA algorithms, double shRNAs, etc.

A primary shRNA screen for ricin resistance/sensitization using the methods of the present invention was performed to identify genetic interactions between genes involved in ricin resistance and/or sensitization. In particular, a pooled shRNA screen in K562 cells was performed with ~25 shRNAs per gene. All annotated human protein-coding genes were screened in duplicate. Notably, shRNA counting +/− ricin revealed statistically significant hits: for 73 genes, knockdown caused ricin resistance (false-discovery rate was <5%); and for 83 genes, knockdown caused ricin hypersensitivity (false-discovery rate was <2%). See, FIG. 2 for a schematic of the pooled high-coverage shRNA screen described herein. FIG. 18 illustrates the hits from the ricin primary screen that were identified using the methods of the present invention. FIG. 19A illustrates that 60S depletion sensitizes to ricin, but RPS25 knockdown protects. FIG. 19B illustrates that COPI depletion sensitizes to ricin. FIG. 19C illustrates that cholesterol metabolism modulates ricin sensitivity.

Figure 15:
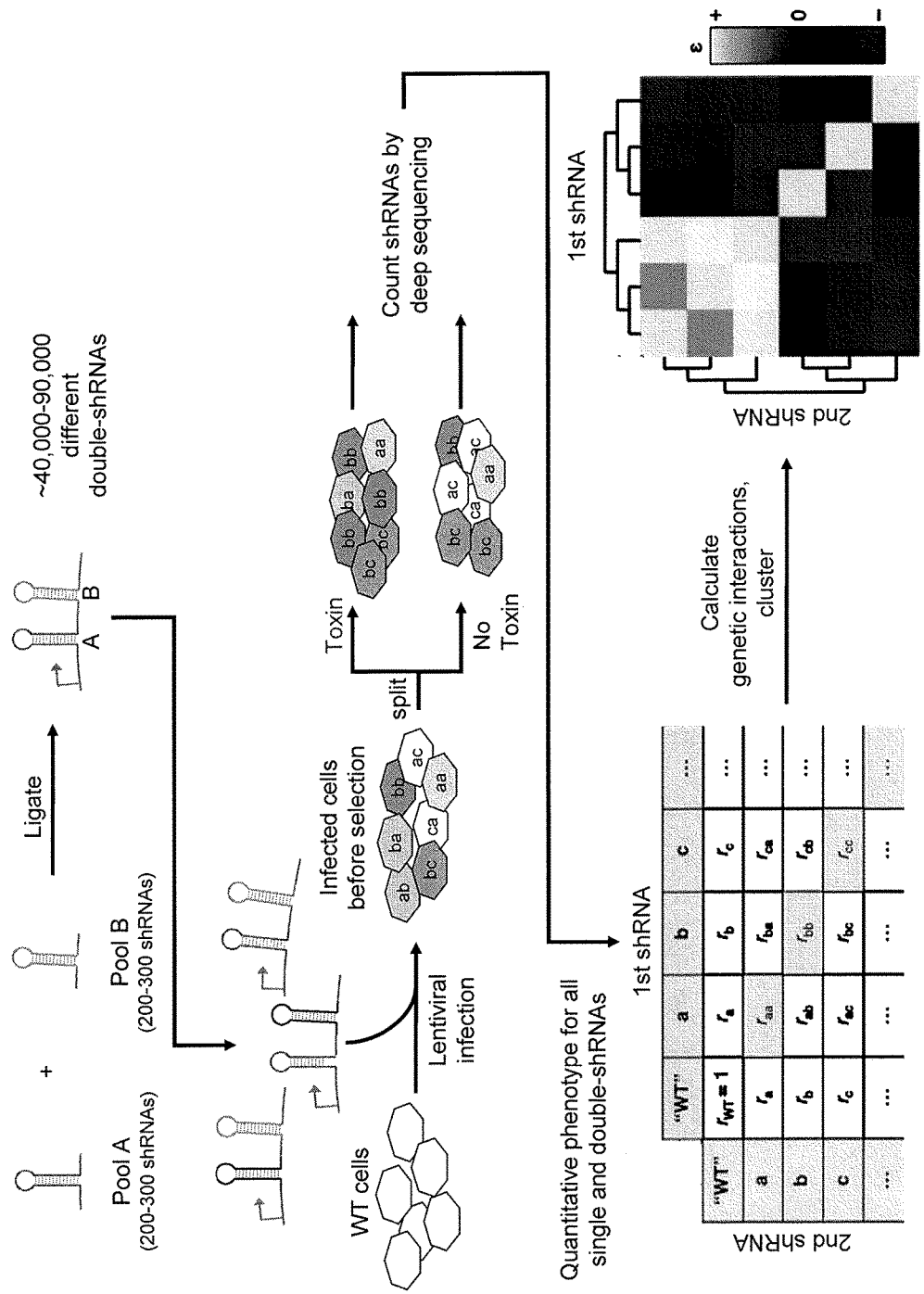
FIG. 15 illustrates a strategy for generating quantitative genetic interaction maps of the invention.
Figure 16:
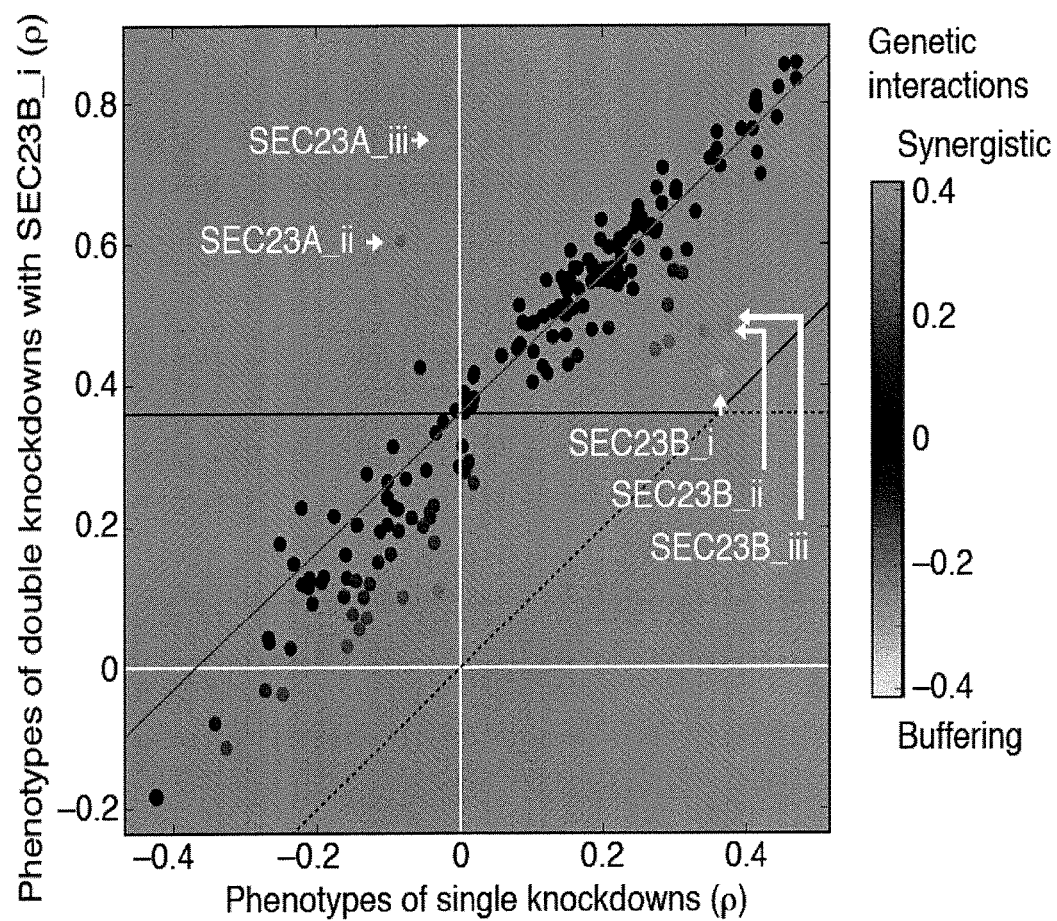
FIG. 16 illustrates an example of genetic interactions from a ricin screen. Phenotypes of single shRNAs versus single shRNAs paired with an shRNA targeting SEC23B. Kappa is a quantitative measure of phenotype; kappa >1: sensitization; kappa <1: resistance. Intriguingly, isoforms SEC23A and SEC23B show opposite phenotypes on their own. In combination with SEC23B, however, the SEC23A shRNAs result in a dramatic magnification of the resistance effect of the Sec23B shRNA.

FIG. 15 illustrates one embodiment of the present invention providing a strategy for identifying genetic interactions between pairwise combinations of shRNAs identified from the primary screen. In the second stage, active shRNAs against hit genes from the primary screens are identified and ligated as a pool to create a double-shRNA library with all pairwise combinations of shRNAs. This approach allows for the rapid creation of large double-mutant libraries for pooled screens and thus facilitates combinatorial genetics on a massive scale. Importantly, it has been found that the activity of the individual shRNAs is maintained in the double-shRNA constructs. Phenotypes are quantified for all combinations of shRNAs, and genetic interactions are calculated. Genes can then be clustered based on their patterns of genetic interaction to identify pathways and functional units. As a non-limiting example, FIG. 20 shows that double mutant analysis revealed strong synergy between Sec23A and Sec23B. FIG. 21 illustrates an exemplary mammalian genetic interaction map (i.e., epistasis map or EMAP) generated using the methods of the present invention.

Example 4. Considerations for Choosing the Number of shRNAs Targeting Each Gene In particular embodiments, the present invention provides a rigorous, data-driven approach for determining the optimal number of shRNAs per gene in shRNA libraries. As discussed below, given the state of the art of shRNA prediction algorithms, it was clear that reducing this number to less than 25 shRNAs would have significantly impacted the ability to confidently identify hit genes. The analysis described herein demonstrates that it is possible with the present invention to reduce the complexity of shRNA libraries to about 15 shRNAs per gene without strongly compromising the sensitivity of the screens.

Rationale for Using Ultra Complex Libraries:

Genome wide shRNA screening strategies have traditionally suffered from problems with high false positive and false negative rates that have compromised their utility. These problems arise from two fundamental problems of RNA interference-based knock downs. First, most siRNAs and shRNAs designed to target a transcript of interest have limited efficacy. Second, siRNAs/shRNAs typically deplete unintended (off-target) transcripts. It has been concluded that existing algorithms have substantial limitations in their ability to accurately predict shRNA effectiveness or off-target effects. For example, a recent study (Fellmann et al., *Mol. Cell,* 41:733-746 (2011)) revealed that only a small fraction of all possible shRNAs designed against a given target effectively deplete the transcript, and that most effective shRNAs could not have been predicted using 3 different algorithms. Even less is known about how to predict and minimize off-target effects.

The use of ultra-complex libraries of the invention overcomes both the common problems of high false-negative rates and high false-positive rates. The high-coverage library described herein maximizes the chances of effectively targeting each gene with multiple independent shRNAs, and thus allows rigorous evaluation of the probability that shRNAs act through the intended target gene. Critically, the libraries of the invention include a large number of matched negative-control shRNAs that allow testing of the statistical significance of hit genes against a background of noise and off-target effects.

Figure 22:
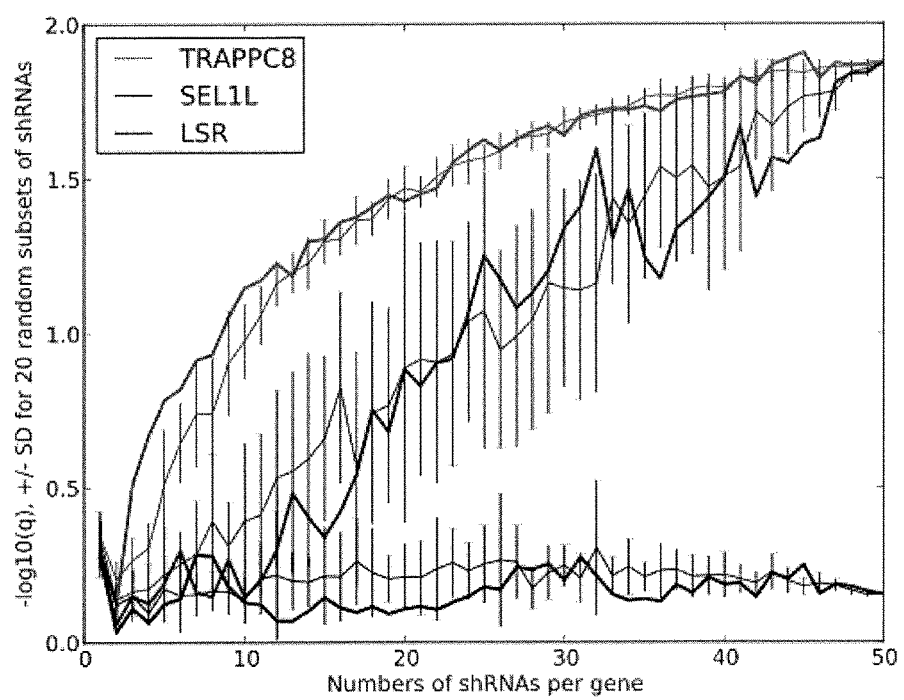
FIG. 22 illustrates the statistical significance of hit genes as a function of number of shRNAs against each gene. Experimental data was generated with an shRNA library targeting 1,079 human genes with 50 independent shRNAs each. shRNA sequences were generated using the publicly available algorithm (codex.cshl.org/RNAi_central/). A pooled screen in K562 cells was carried out to identify genes affecting sensitivity to treatment with the toxin ricin. TRAPPC8 and SEL1L were identified as a strong and intermediate strength hit genes, respectively, whereas LSR was not a hit gene. To simulate the results that would have been obtained using a library with fewer shRNAs/gene, random subsets of shRNAs were chosen and the q-value (which represents statistical significance after correction for multiple hypothesis testing) was calculated. Random subsets were generated 20 times, and average +/– standard deviation for the obtained q values (plotted as –log 10 q) are shown. When significantly fewer than 25 shRNAs per gene were used, the intermediate strength hit gene (SEL1L) is not robustly distinguishable from the non-hit gene (LSR). For higher numbers of shRNAs per gene, the distinction is improved. Similar results are obtained when the top-scoring shRNAs according to the design algorithm are chosen for each subset (bold line), rather than a random subset.

The ricin screen data described in Example 3 also provides an objective test for evaluating how the number of shRNAs/gene impacts that sensitivity and specificity of the screening approach of the invention. Specifically, for a range of validated hits in the ricin screen, a library containing 50 shRNAs/gene was synthesized and screened. The effect on the ability to robustly identify hit genes if libraries were computationally restricted to include fewer shRNAs/gene was evaluated. It was found that decreasing the number of shRNAs to less than 25 shRNAs/gene significantly compromised the ability to confidently identify hit genes of intermediate strength (e.g., SEL1L) from non-hit genes like LSR (FIG. 22). This may increase the amount of downstream work that would be needed to validate hit genes and may compromise downstream efforts to construct high quality double shRNA genetic interaction maps. The conclusion is generally the same if the best shRNAs are selected using existing shRNA prediction tools like the algorithm used for the pGipZ based shRNA libraries (codex.cshl.org/RNAi_central/) or even if target sequences that have been validated in other shRNA or siRNA contexts are favored.

Figure 24:
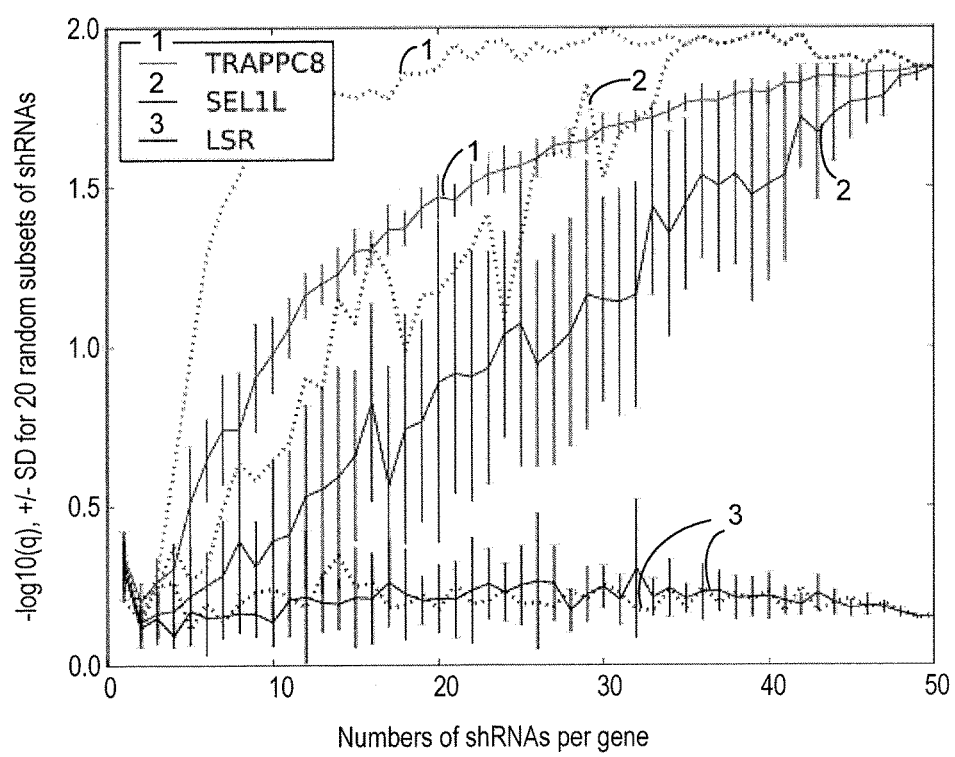
FIG. 24 illustrates that on the basis of data from a genome-wide screen, a score was developed to predict the most effective shRNAs. When choosing the subsets of shRNAs based on our score (dotted line), results are significantly improved and fewer shRNAs per gene are necessary to robustly identify intermediate strength hit gene SEL1L and distinguish them from non hit genes like LSR.

However, the present invention provides an shRNA prediction algorithm (e.g., as described herein) that is tailored to specifically identify the shRNA sequences that are most likely to be effective. Using this novel algorithm to select the top shRNAs from the 50 shRNAs screened reveals that even for intermediate strength hit genes like SEL1L, a high degree of specificity using 15 shRNAs can be obtained (FIG. 24).

In conclusion, using 25 shRNAs/gene, the initial high-coverage shRNA libraries enabled the robust identification of active shRNAs for a range of strong and intermediate hit genes. This makes it possible to identify hit genes and to find a set of (typically 3) shRNAs that effectively target each of these hit genes. These validated shRNAs then serve as critical reagents for downstream studies, including the construction of high precision quantitative genetic interaction maps. As such, the development and validation of an improved shRNA selection algorithm described herein advantageously enables the use of 15 shRNAs per gene.

Example 5. Integrated Platform for Genome-Wide Screening and Construction of High-Density Genetic Interaction Maps in Mammalian Cells Abstract A major challenge of the postgenomic era is to understand how human genes function together in normal and disease states. In microorganisms, high-density genetic interaction (GI) maps are a powerful tool to elucidate gene functions and pathways. This example describes the development of an integrated methodology based on pooled shRNA screening in mammalian cells for genome-wide identification of genes with relevant phenotypes and systematic mapping of all genetic interactions (GIs) between them. This example presents the complete quantitative framework underlying the strategy, including experimental design, derivation of quantitative phenotypes from pooled screens, robust identification of hit genes using ultra-complex shRNA libraries, prediction of active shRNAs and detection of off-target effects, calculation of GIs from double-shRNA screens and construction of GI maps. The same double-shRNA library can rapidly be screened in a multitude of conditions and cell types. This example demonstrates how such a comparative GI mapping strategy enables functional dissection of physical complexes and context-dependent pathways.

Introduction

The first human genome sequence was determined more than ten years ago (Lander et al. 2001; Venter et al. 2001), and the revolution in sequencing technology has facilitated the deciphering of hundreds more human and cancer genomes since then (Abecasis et al. 2012; Mardis 2012). The next frontier is the development of strategies for the systematic elucidation of gene function in health and disease contexts.

RNA interference (RNAi) technology has facilitated forward-genetic approaches in mammalian cells, but the analysis of genome-wide RNAi screens remains challenging (Kaelin 2012). Major confounding factors are false-negative results caused by insufficiently active shRNAs, and false-positive results caused by off-target effects. Indeed, the challenges of off-target effects have recently been highlighted by papers from the Elledge and Sanders lab which shows that these effects can be pervasive in genome-wide screens and are not robustly detected by the some of the standard precautions typically used (Schultz et al. 2011; Adamson et al. 2012).

Furthermore, even when hit genes are correctly identified, effective follow up to uncover their function often requires intense effort. In yeast and other microorganisms, high-density genetic interaction (GI) maps have been highly successful at defining gene function, revealing functional relationships between previously uncharacterized genes and elucidating cellular pathways (Tong et al. 2001; Pan et al. 2004; Tong et al. 2004; Schuldiner et al. 2005; Collins et al. 2007; Roguev et al. 2008; Jonikas et al. 2009; Bandyopadhyay et al. 2010; Frost et al. 2012). GIs quantify the effect that loss of function of one gene has on the phenotype caused by the loss of function of another gene. In GI maps, GIs are determined for a large number of pairwise combination of genes, and genes are clustered based on the similarity of their GI patterns. The clustering typically reveals groups of genes that encode physically interacting proteins or act in a common pathway (Collins et al. 2006).

In human cells, such a systematic elucidation of the functional interactions between human genes will be key to understanding how combinations of genes cause common polygenetic diseases and to developing precision therapies based on a patient's genetic background. Additionally, GI maps can detect rare synthetic lethal gene pairs, which would be ideal drug targets for combination therapies that prevent the development of drug resistance of rapidly evolving diseases like cancer.

This example presents a comprehensive, robust approach that addresses the above challenges to the effective application of RNAi-based approaches to study gene function in mammalian systems. Specifically, an integrated technology platform has been developed for genome-wide screening and construction of high-density GI maps in mammalian cells based on pooled shRNA screens. Pooled shRNA screens have many advantages over well-based arrayed siRNA screens, particularly for the investigation of GIs (see Discussion for details). This example describes a principled framework for collecting and analyzing data, and illustrates the broad potential of this approach. Quantitative, shRNA-intrinsic phenotypes, such as growth or drug sensitivity, are extracted from pooled screens.

This approach is based on the development of ultra-complex shRNA library (~25 shRNAs targeting each human protein-coding gene) that includes a large number (>1,000) of negative-control shRNAs. The rapid creation and monitoring of such complex libraries is enabled by two key technologies, microarray-based oligonucleotide synthesis and next generation sequencing (Bassik et al. 2009). This approach has been successfully applied in a pilot study of susceptibility of human cells to the toxin ricin, (see, Example 6). In the present study, a strategy for robust identification of hit genes was established using this library, which can in principle overcome both false-positive and false-negative issues. This example presents a machine-learning approach for the prediction of active shRNAs, which can be used to select shRNAs against hit genes for the construction of a double-shRNA library. This example describes a strategy for constructing a high-density GI map based on pooled screening of the double-shRNA library. This example shows how shRNAs with partial off-target effects can be identified and removed from GI maps. The ease with which the same double-shRNA library can be screened for different phenotypes to compare context-specific GI maps is a distinguishing feature of this approach. Finally, this example presents a growth-based GI map and demonstrates how comparison with the ricin resistance-based GI map facilitates the dissection of functional pathways in different conditions and cellular states.

RESULTS

An Integrated Platform for Genome-Wide Screening and Mapping of Genetic Interactions The present inventors have developed an integrated suite of experimental and computational approaches to robustly identify genes of interest using pooled shRNA-based screens in mammalian cells and to systematically map genetic interactions between these genes to uncover functional relationships. This section and FIG. 25 give an overview of the multi-step strategy; the subsequent sections provide the rationale, describe the details and demonstrate the performance of the individual steps.

To conduct the initial primary genome-wide screen (FIG. 25), a pooled ultracomplex shRNA library is introduced into mammalian cells via lentiviral infection at a low multiplicity of infection. A fraction of this infected cell population is subjected to selection for a phenotype of interest. Depending on the biological question, this selection can consist simply of a period of growth under standard conditions, or growth in the presence of a drug, toxin, or other selective pressure. Any method that physically isolates or enriches cells based on a phenotype of interest can also be used, such as selection for cell migration, cell size or expression of a reporter gene by fluorescence-activated cell sorting and other technologies. The frequencies of shRNA-encoding cassettes in the selected population and an unselected control population are determined by deep sequencing, hit genes, and shRNAs that effectively target these hit genes, are identified.

Next, individually barcoded lentiviral vectors for expression of the shRNAs selected from the primary screen are constructed (FIG. 25). These vectors are pooled for batch retesting of the shRNA phenotypes, and can also be used to compare the role of the targeted genes in different cell lines, or with different selective pressures.

Finally, the barcoded shRNA vectors are digested and ligated in a pooled format to generate a library expressing all pairwise combinations of double-shRNAs (FIG. 25). The phenotypes of these double-shRNAs are measured in a pooled screen, and from these, genetic interactions (GIs) are calculated. GI patterns of shRNAs targeting the same gene are then averaged and genes are clustered based on their GI pattern to obtain a high-density GI map. The same double-shRNA library can be screened for different phenotypes or in different cell lines to generate a set of GI maps. Comparison of these GI maps reveals condition- and background-specific GIs and pathways.

Quantitative shRNA Phenotypes from Pooled shRNA Screens

Detection of hits in primary screens and construction of GI maps requires a method for inferring underlying quantitative phenotypes based on behavior in pooled growth experiments. A principled framework was developed to derive distinct phenotypes that reflect shRNA-intrinsic effects from pooled shRNA screens. The simplest experimental design for a pooled screen is a growth-based screen in which the frequencies of knockdown cells are compared between the starting time point ($t_0$), and a later time point in the screen (t). If cells are maintained in exponential growth phase throughout the screen, and g is the growth rate of wild-type (WT) cells, the effect of an shRNA X is defined such that cells expressing this shRNA have a growth rate of $(1+\gamma_X)g$ (FIG. 26A). Thus, positive $\gamma_X$ represent an increase in fitness, whereas negative $\gamma_X$ represent a decrease in fitness (FIG. 26B). $\gamma_X$ can be calculated from the shRNA frequencies determined by deep sequencing and the observed growth parameters of the bulk cell population (Methods). $\gamma$ values calculated in this way are highly reproducible between independent screens (FIG. 26B), which facilitates direct comparison and averaging of data from screens that were carried out separately. It is also possible to compare samples taken at different time points $t_1$, $t_2$ etc., to ensure that enrichment of certain shRNAs was due to consistently higher growth rates, rather than rare jackpot effects.

Many genetic screens address the growth of cells in the presence of a specific selective pressure that inhibits the net growth of WT cells, resulting in a diminished growth rate g-k (FIG. 26A). The resistance phenotype ρ of an shRNA is defined such that the growth rate of cells expressing shRNA X in the presence of selective pressure is $(1+\gamma_X)g-(1-\rho_X)k$ (FIG. 26A). Full resistance corresponds to $\rho_C=1$, partial resistance to $0<\rho X<1$, and sensitization to $\rho_X<0$ (FIG. 26B). To determine $\rho_X$, frequencies of cells expressing shRNAs are compared in unselected and selected populations (Methods).

When designing the selection experiment, the selective pressure should be titrated in preliminary experiments to obtain a desired value of k. Larger selective pressures k will enhance the differential changes in cell frequencies; however, if the selective pressure is so large that the population size decreases dramatically, this population bottleneck will increase Poisson noise for the frequency measurements, and increase the likelihood of losing some species completely. Good results are obtained with k/g around 0.5 over a time corresponding to 8-12 doublings of WT cells in standard conditions.

Very divergent levels of selective pressure, such as very different concentrations of a drug or toxin, may interact with different cellular pathways, and thus ρ values from experiments are not necessarily comparable across a wide range of selective pressures. However, experiments with modest differences in levels of selective pressure show good reproducibility of ρ values (FIG. 26D), again allowing averaging of data from independent screens.

Some biological problems require k≈0, such as the drug treatment of a cancer cell line that is resistant to this drug, with the goal to recover shRNAs that resensitize the cells to the drug. Definitions of quantitative phenotypes for this case and for sorting-based screens are given in the Methods.

Identification of Hit Genes from the Primary Screen

To address the problems of false-positive and false-negative results in genome-wide RNAi screens, an ultra-complex library was created that targets each human protein-coding gene with ~25 independent shRNAs and contains a large set (>1,000) of negative-control shRNAs. Qualitatively, the reasoning behind the use of such libraries is that the large number of shRNAs targeting each gene increases the likelihood of including several effective shRNAs, which should reduce the false-negative rate. Requiring several independent shRNAs targeting a gene to cause the phenotype of interest in order to call the target gene a hit gene should reduce the false-positive rate caused by off-target effects.

It was reasoned that analysis of screening data based on hard cut-offs for shRNA phenotypes and numbers of active shRNAs per gene would discard much of the information contained in the rich data set. Instead, statistical evaluation of the phenotype distribution of all shRNAs targeting a given gene utilizes all available information to evaluate whether the gene is a hit. This concept also underlies the RIGER approach (Luo et al. 2008); but whereas RIGER compares shRNAs targeting a gene of interest to the entire set of shRNAs targeting all genes, an important innovation in the present strategy is the comparison of the shRNAs targeting each gene to the negative-control shRNAs (FIG. 26E). The large set of negative control shRNAs provides the appropriate "null distribution" by controlling for both the measurement noise and unintended off-target effects.

Two statistical tests that derive a P value for each gene were compared: The Mann-Whitney U test (MW test) and the two-sample Kolmogorov-Smirnov test (KS test) yielded generally very similar answers, with few exceptions. The MW test performed more robustly with noisy datasets, and therefore the MW test was generally used.

The use of negative controls for statistical testing increased the sensitivity of hit detection: Based on a ricin resistance screen, the P value for a given gene was calculated by comparing shRNAs targeting the gene either with negative control shRNAs, or with the distribution of all shRNAs in the library. When negative controls were used, more hits were significant at a false discovery rate (FDR) of 5%.

To test the robustness of the present approach for hit identification, a ricin resistance screen was conducted using an shRNA library targeting 1,079 genes each with 50 independent shRNAs and randomly divided shRNAs targeting each gene into two "half-libraries". P values for each gene were calculated separately based on the results of each "half-library" (FIG. 26F). Genes were called hits for a false-discovery rate (FDR)<5%. The overlap in called hits (at a false-discovery rate below 5%) was highly significant ($P=5.6 \cdot 10^{-28}$, Fisher's exact test for the example shown in FIG. 26F; similar values were obtained in other random divisions of the test library into half-libraries). The RIGER approach (Luo et al. 2008) was also naively applied, which does not use a negative control set of shRNAs, to the same randomly generated half-libraries shown in FIG. 26F. It was found that applied to these data, there was a better overlap in hits detected by the MW test using negative controls than with RIGER, likely reflecting the increase in robustness obtained by the use of negative-control shRNAs. In a pilot genome-wide screen for genes affecting ricin susceptibility, the present approach allowed the identification of a wide range of protective and sensitizing hit genes with remarkable specificity and sensitivity.

A Sequence Score Predictive of shRNA Activity

Figures 27A, 27B:
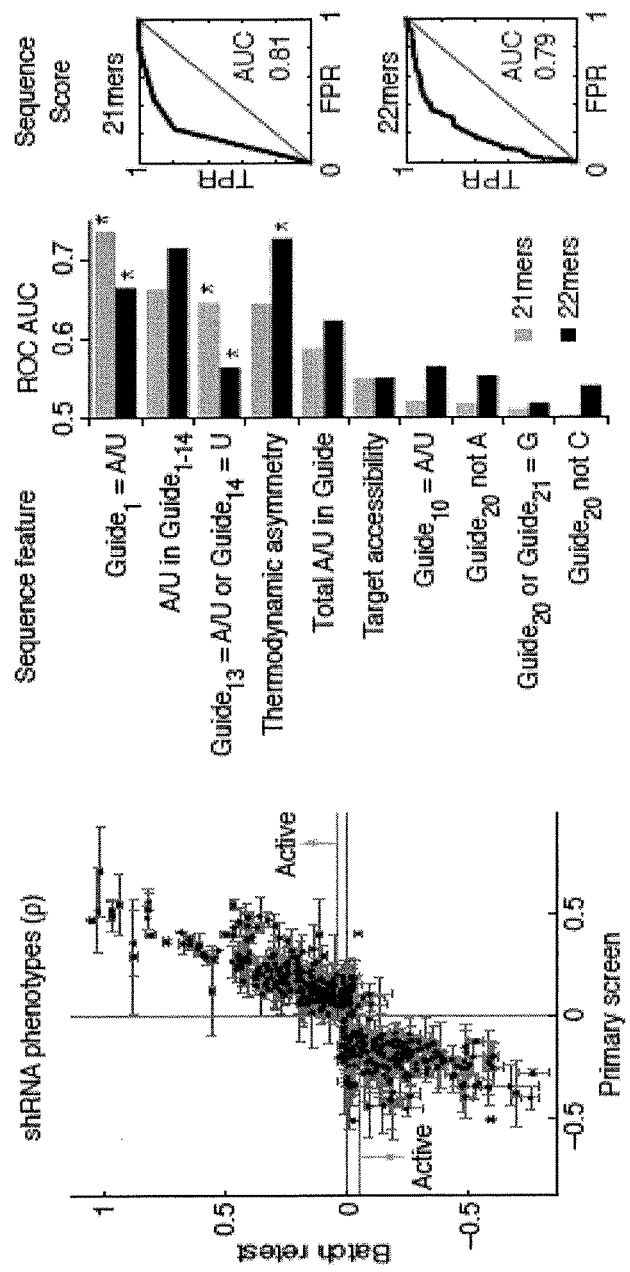
FIGS. 27A-E illustrate a prediction of active shRNAs based on sequence properties. (A) Comparison of ricin resistance phenotypes (p) for shRNAs targeting hit genes in a primary screen and in a high-coverage batch retest of individually cloned shRNAs. Error bars indicate the spread between two experimental replicates. Lines indicate the thresholds used to define "active" shRNAs for machine learning purposes: $\rho>0.05$ for protective (enriched) shRNAs, $\rho<-0.05$ for sensitizing (depleted) shRNAs. (B) Sequence features as predictors of shRNA activity. Features were target accessibility as predicted from the secondary structure stability of the mRNA context of the shRNA target, and modified versions of the sensor rules (Fellmann et al. 2011). Left: Areas under the receiver operating characteristic curve (ROC AUC) for sensor rules used as quantitative metrics. Rules were tested separately for 21mer guide strands (grey bars) and 22mer guide strands (black bars). Stepwise logistic regression was used to create an integrated Sequence score predicting shRNA activity for 21mer guide strands and 22mer guide strands. Features included in the Sequence scores are marked by asterisks. Right: ROC curves for the Sequence Scores are shown with the AUC displayed in blue; TPR=true positive rate; FPR=false positive rate. (C-E) Based on shRNA phenotypes in a ricin resistance screen targeting genes with 50 shRNAs each, P values for each gene were calculated on the basis of subsets of the data; the number of shRNAs included per gene was varied. shRNA subsets were either chosen randomly 100 times, and means of –log 10 of P values are shown, with errorbars indicating SD, or shRNA subsets were chosen based on the highest Sequence scores. (C) Results are shown for three representative genes: a strong hit (RAB1A), a moderate hit (STX16), and a non-hit (CRYAB). For the purpose of this analysis, sequence scores were created based on a dataset from which shRNAs targeting RAB1A, STX16 and CRYAB were excluded. (D) P values calculated based on 45 shRNAs per gene are compared with P values calculated based on 10 shRNAs per gene for all 1,079 genes target by Library 2. Sequence scores for individual shRNAs were calculated based on data subsets excluding these specific shRNAs. (E) As in (D), P values calculated based on shRNA subsets were compared to P values calculated based on 45 shRNAs per gene. On the left, the slope of the linear regression for this comparison is shown, on the right the Pearson correlation coefficient, both as a function of shRNA subset size. Subsets were either chosen randomly (grey) or based on their Sequence Score (black).

A long-standing quest in the development of RNAi technology has been the optimization of siRNA/shRNA sequences for effective knock-down of the intended target (Fellmann et al. 2011), and, more recently, for the minimization of off-target effects (Gu et al. 2012). A more thorough understanding of siRNA/shRNA design rules would facilitate the design of more compact and potent shRNA libraries in the future. To investigate which sequence properties increased the likelihood of shRNA activity specifically in the present expression system, machine-learning approaches were applied to a training data set of 461 individually cloned shRNAs targeting hit genes in the ricin resistance pilot screen (FIG. 27A and Methods).

The first factor examined for its predictive value for shRNA activity was the length of the shRNA guide strand. The current genome-wide library contains shRNAs with 21mer guide strands (designed using the si-shRNA Selector program, Matveeva et al. 2010) and shRNAs with 22mer guide strands (designed using the Hannon lab shRNA retriever program, Paddison et al. 2004). The 22mer guide strands were more likely to be active than the 21mer guide strands ($P=0.8 \cdot 10^{-3}$, Fisher's exact test).

Next, the base frequencies of active and inactive guide strands at each position of the guide strand were compared, and an A or U at the first position of the guide strand was found to be highly predictive of shRNA activity ($P<10^{-5}$ for 21mer guide strand, $P<10^{-7}$ for 22mer guide strand, $\chi 2$ test). This study also investigated sequence properties of the 50 mRNA bases flanking the shRNA target site on either side, but did not find significant predictors of shRNA activity (no positions with Bonferroni-corrected $P<0.05$, $\chi 2$ test, data not shown).

Features of active shRNAs have previously been deduced from experimental data obtained with the "sensor" approach (Fellmann et al. 2011), and were termed "sensor rules". While the design algorithms used herein to create shRNAs in the primary screen library already preselected shRNAs that tended to conform to some of the sensor rules, such as thermodynamic asymmetry, several of the sensor rules still had predictive power for shRNA activity within the library (FIG. 27B). Presence of A or U in the first position of the guide strand, which was independently found to be an important predictor of shRNA activity is also one of the sensor rules. The sensor rules were originally postulated as binary criteria for 22mer guide strands (Fellmann et al. 2011), but this study found that they also were effective classifiers when used as quantitative metrics for both 21mer and 22mer guide strands in the library (FIG. 27B).

An additional factor that has been reported to affect shRNA activity is the accessibility of the target site within the mRNA (Ameres et al. 2007). In viral genomes, the experimentally determined secondary structure of the target site is strongly anti-correlated with shRNA activity (Tan et al. 2012). Since there is currently no comprehensive set of experimental data for in vivo accessibility of human mRNAs, this study used the unafold algorithm (Markham and Zuker 2005) to predict the thermodynamic stability of the mRNA segment containing the target site and the flanking 50 bases upstream and downstream. A weak correlation was found a between predicted target site accessibility and shRNA activity in the data set. These results were qualitatively similar when the length of the flanking region used for RNA structure prediction was varied. It is possible that experimentally derived information for secondary structures of target regions in human mRNAs in vivo will be strongly predictive of shRNA activity, as it is for viral targets (Tan et al. 2012). However, it is also possible that human mRNAs are generally less structured than viral RNAs, and that the average target accessibility is therefore less predictive of shRNA activity.

To integrate weighted information about sequence properties in a predictive score, referred to herein as "Sequence Score", stepwise logistic regression (Gelman and Hill 2007) was used. The resulting Sequence Scores for 21mer and 22mer guide strands were excellent metrics of shRNA activity for both enriched and depleted shRNAs and only incorporated two or three sequence features, respectively (FIG. 27B). Taking into account additional features did not improve the predictive power of the Sequence Score, since many of the sequence features are correlated for shRNAs in the present library.

Evaluation of Library Formats Based on Performance in Primary Screens

The ultimate criterion for evaluating shRNA library design is not the strength of on-target knockdown, but the ability of the library to robustly detect hit genes in a primary screen, which reflects the ratio of signal (on-target effects on hit genes) to noise (off-target effects of the negative control shRNAs and shRNAs targeting non-hits). While the Sequence Score, introduced above, was derived based on the activity of a limited set of shRNAs targeting hit genes, this study investigated whether it would also be a useful tool to increase shRNA library performance, and specifically allow the design of more compact libraries in which shRNAs are chosen based on the Sequence Score.

Figures 27C, 27D:
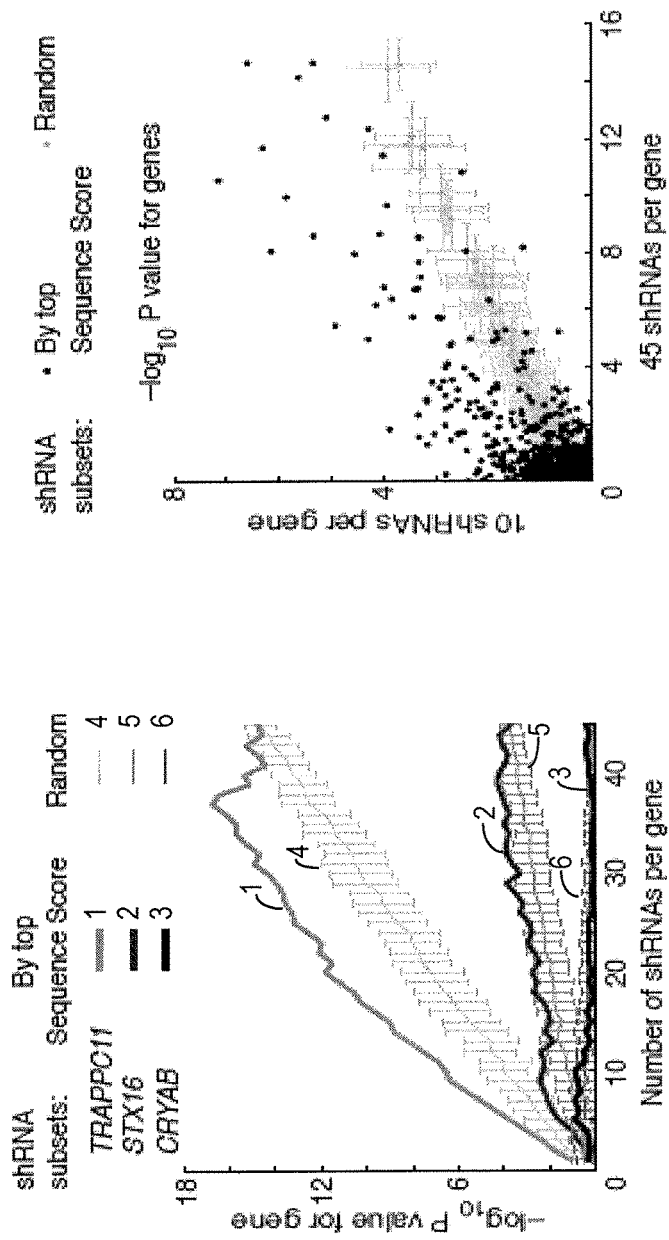

To address this question, data from the ricin resistance screen with an shRNA library targeting 1,079 genes with 50 shRNAs each were analyzed. shRNA subsets were computationally created and P values for genes calculated based on shRNA subsets of varying sizes were compared. In FIG. 27C, results are shown for three representative genes with distinct ricin resistance phenotypes: TRAPPC11, a strong hit gene, STX16, a weak hit gene, and CRYAB, which was not a hit. When these shRNA subsets targeting these genes were created randomly, discrimination between the weak hit STX16 and the non-hit CRYAB required ~15 or more shRNAs. However, when subsets of shRNAs were created based on the shRNAs with the highest Sequence Scores (calculated here for a training set of shRNAs that did not include shRNAs targeting STX16, TRAPPC11 and CRYAB), even ~7 shRNAs were enough to clearly distinguish STX16 from CRYAB.

Figure 27E:
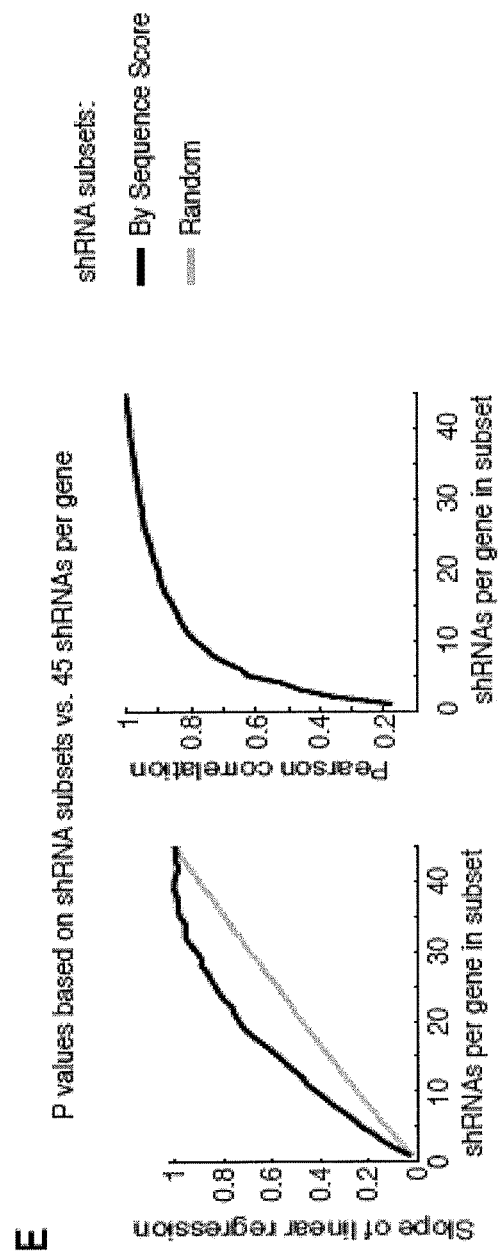

The trend observed for the three example genes was generally valid for all genes targeted by the library. P values calculated based on the top-scoring 10 shRNAs per gene were highly correlated with P values calculated based on 45 shRNAs per gene, and P values were consistently higher than those calculated from random subsets of 10 shRNAs per gene (FIG. 27D). This pattern was also observed for different shRNA subset sizes (FIG. 27E). Thus, the numbers of shRNAs per gene required to detect even weak hit genes may be substantially reduced by choosing shRNAs based on their sequence score for future shRNA libraries.

The performance of an shRNA library format should ideally be tested in a direct experiment. To illustrate the power of such an approach for evaluating the performance of 22mer guide strands versus 21mer guide strands, a pair of libraries was created that both targeted the same set of 1,079 genes and included a large number of negative controls. One library contained only 21mer guide strands and the other only 22mer guide strands, which were selected by independent algorithms (Paddison et al. 2004; Matveeva et al. 2010). Both libraries were screened for ricin resistance. While there was a broad agreement in called hits, the 22mer library detected hits more sensitively than the 21mer library.

Selection of Active shRNAs and Construction of the Double-shRNA Library

After the genome-wide primary screen, the next step in the present strategy is the selection of shRNAs targeting hit genes for further characterization and inclusion in a double-shRNA library. These shRNAs were individually cloned into the barcoded vector pMK1098 (FIG. 28B) and pooled, and their phenotypes were determined in a batch retest experiment. Phenotypes determined by batch retest were highly reproducible between experimental replicates, whereas phenotypes determined in the primary genome-wide screen were more variable (errorbars in FIG. 27A). This difference is likely due to the higher coverage of cells per shRNA in the batch retest (~50,000 cells/shRNA) than in the primary screen (1,000 cells/shRNA). Population bottlenecks in pooled screens are known to be a source of Poisson sampling noise, especially when the same population is diluted several times over the course of the screen (Pierce et al. 2007).

Despite the noise, phenotypes observed in the primary screen correlated broadly with batch retest phenotypes (FIG. 27A). However, some shRNAs for which resistance phenotypes were measured in the primary screen had phenotypes close to WT upon batch retest, suggesting that the shRNA was inactive, and its deviating phenotype in the primary screen had been due to measurement noise.

Figure 28A:
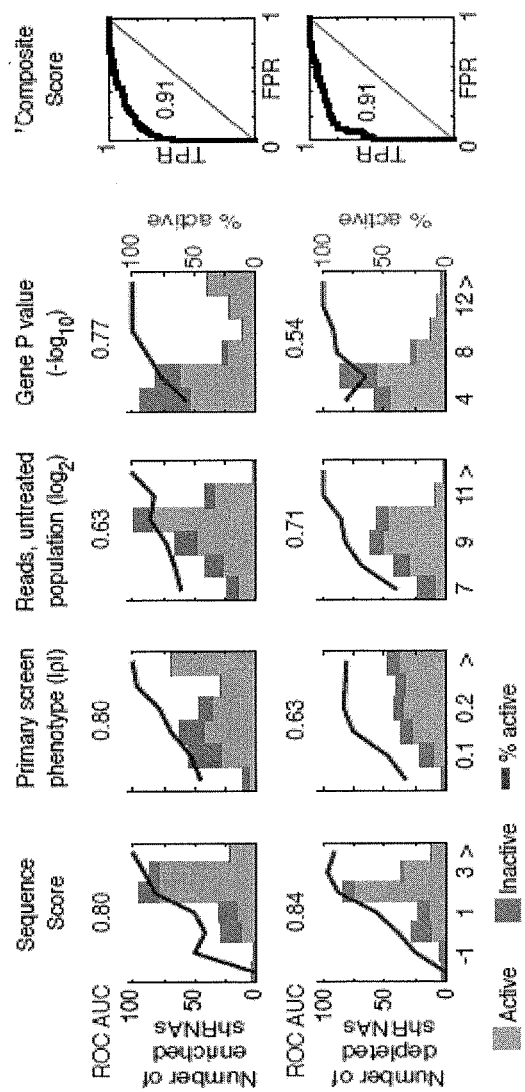
FIGS. 28A-C illustrate genetic interactions from double-shRNA screen phenotypes. (A) A Composite Score integrates the Sequence Score with information from the primary screen to guide selection of shRNAs for inclusion in the double-shRNA library. Left: Dependence of shRNA activity on Sequence Score, phenotypic strength, log 2 number of deep sequencing reads in the untreated population and –log 10 P value of the gene they are targeting. These variables are binned; numbers refer to the upper bounds of the bins, and the last bin contains all cases exceeding the previous bound, where indicated by the > symbol. Numbers of active and inactive shRNAs per bin are shown as stacked light grey and dark grey bars, respectively. The percentage of active shRNAs per bin is indicated by the line. ROC AUC are shown. Results are displayed separately for enriched shRNAs (top row) and depleted shRNAs (bottom row). Right: Stepwise logistic regression was used to create a Composite Score predicting shRNA activity for enriched and depleted shRNAs. ROC curves for the Composite Scores are shown with the AUC. (B) shRNAs selected from the primary screen are individually cloned into a minimal miR30 context flanked by N10 barcodes on either side. A double-shRNA library is created by a pooled restriction digest and ligation strategy. In the resulting plasmids, two shRNAs are expressed each from a miR30 context in the 3'UTR of the same mRNA. A combinatorial barcode created at the junction uniquely identifies each double shRNA. (C) Genetic interactions are calculated as deviations from the expected double-mutant phenotype, which can be defined as product (dark grey) or sum (light grey) of the single mutant phenotypes, or can be derived empirically by linearly fitting the relationship between single shRNA phenotypes and double-shRNA phenotypes in combination with an shRNA of interest (in this example SEC23B_ii). Heatmap display of GIs from negative to positive, based on the linear fit for expected double-shRNA phenotypes. (D) Comparison of biologically meaningful information obtained using the different definitions of expected double-shRNA phenotypes, based on data for growth and ricin resistance. Average correlation z-scores of genetic interactions (GIs) between shRNAs targeting the same gene, compared to shRNAs targeting different genes, and shRNAs targeting genes encoding subunits of the same protein complex compared to others.

To optimize the selection of shRNAs for an increased rate at which individually cloned shRNAs reproduced the desired phenotype, this study examined how experimental variables from the primary screen, in addition to the Sequence Score, affected shRNA activity. As expected, primary screen phenotypes were predictive of shRNA activity (FIG. 28A). This relationship was stronger for enriched shRNAs than for depleted shRNAs, most likely reflecting the fact that depleted shRNAs are present at lower count numbers in the deep sequencing data, and thus subject to higher levels of Poisson noise. In support of this hypothesis, this study found that shRNAs that were more abundant in the untreated population had a higher probability of being active (FIG. 28A), presumably because their frequency was measured more accurately in the primary screen. Interestingly, shRNAs targeting hit genes with a higher P value were also more likely to be active (FIG. 28A), supporting the idea that individual shRNA phenotypes in the primary screen are noisy, but more likely to reflect real activity if the overall pattern of shRNA phenotypes for a gene indicates that the gene is a stronger hit.

Stepwise logistic regression was used to derive a Composite Score predicting shRNA activity, which reflected both sequence properties and experiment-specific parameters (FIG. 28A). Given the differences for enriched and depleted shRNAs (FIG. 28A), separate scores for these two classes of shRNAs were created. The resulting scores were powerful predictors of shRNA activity (FIG. 28A).

Figure 28B:
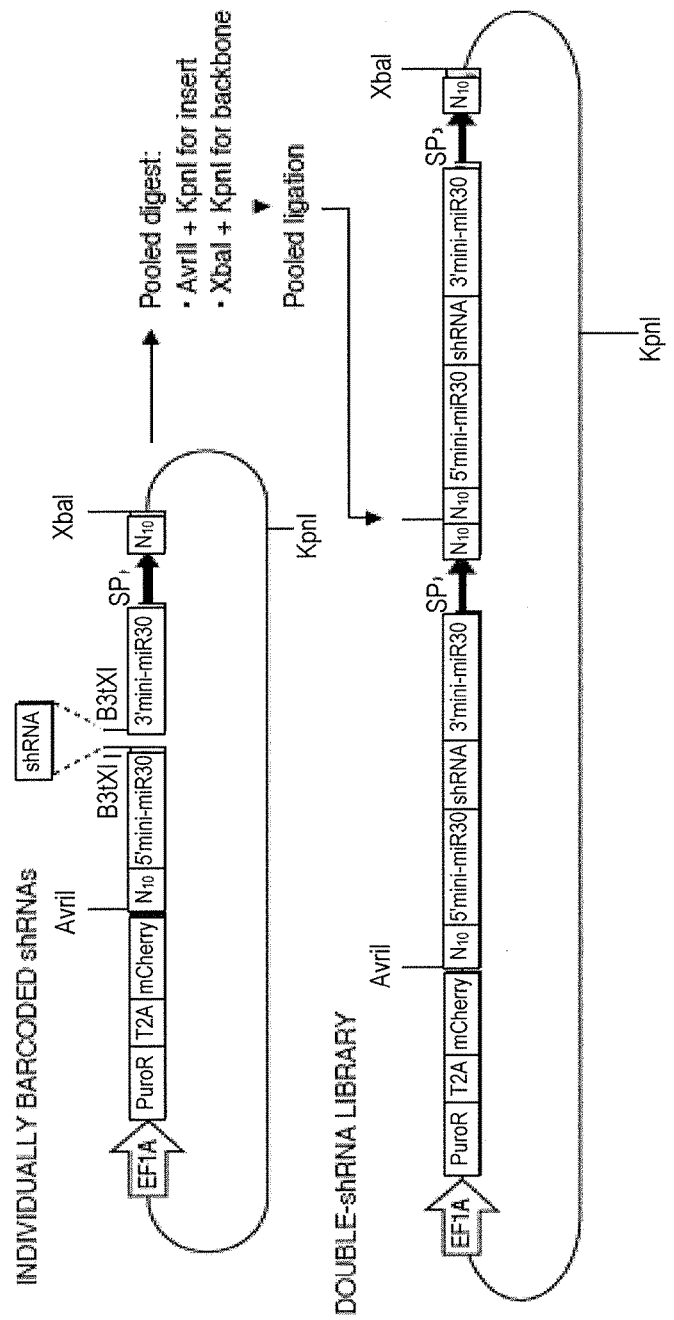

To construct a double-shRNA library from individually barcoded shRNAs, active shRNAs (usually 3 targeting each hit gene) and negative-control shRNAs were pooled and all pairwise combinations of shRNAs were created by a pooled ligation strategy. In the resulting double-shRNA plasmids, both shRNAs are processed from minimal miR30a-contexts embedded in the 3'UTR of the same RNA-polymerase II-transcribed mRNA (FIG. 28B). The combinatorial barcode created by ligation uniquely identifies each double-shRNA and is read out by deep sequencing. While square GI maps were created from double-shRNA libraries in which the same set of shRNAs was present in the first and second position, the strategy can easily be modified by using different pools of shRNA plasmids to create the backbone and insert for ligation. Thus, rectangular GI maps can be constructed, in which one dimension comprises "bait genes" representative of different cellular pathways, whereas the other dimension comprises a larger number of "query genes", which include genes of unknown function.

Pairwise combination of active shRNAs and negative control shRNAs result in three classes of double-shRNAs: pairs of negative-control shRNAs, which are used to derive the wildtype (WT) phenotype, pairs of one active shRNA and one negative-control shRNA, which represent the individual phenotypes of the single active shRNA, and pairs of two active shRNAs (FIG. 25C). Importantly, shRNAs maintain their activity in either position within the double-shRNA construct.

Calculation of GIs from Double-shRNA Phenotypes

GIs are generally defined as the deviation of observed double-mutant phenotypes from the phenotype expected based on the two individual mutant phenotypes. If the phenotype is directly related to fitness or growth rate, the expected double-mutant phenotype is commonly defined as the product of the two single mutant phenotypes, although other definitions exist, such as the sum definition (Mani et al. 2008). For more complex phenotypes, such as the activation of a reporter gene, the expected double-mutant phenotype has successfully been defined empirically for each gene (Jonikas et al. 2009): Based on the assumption that strong GIs are rare, a fit of the observed double-mutant phenotypes to a rationally chosen function is used to define the expected phenotype, and GIs are quantified as deviations from this fitted function.

Figures 28C, 28D:
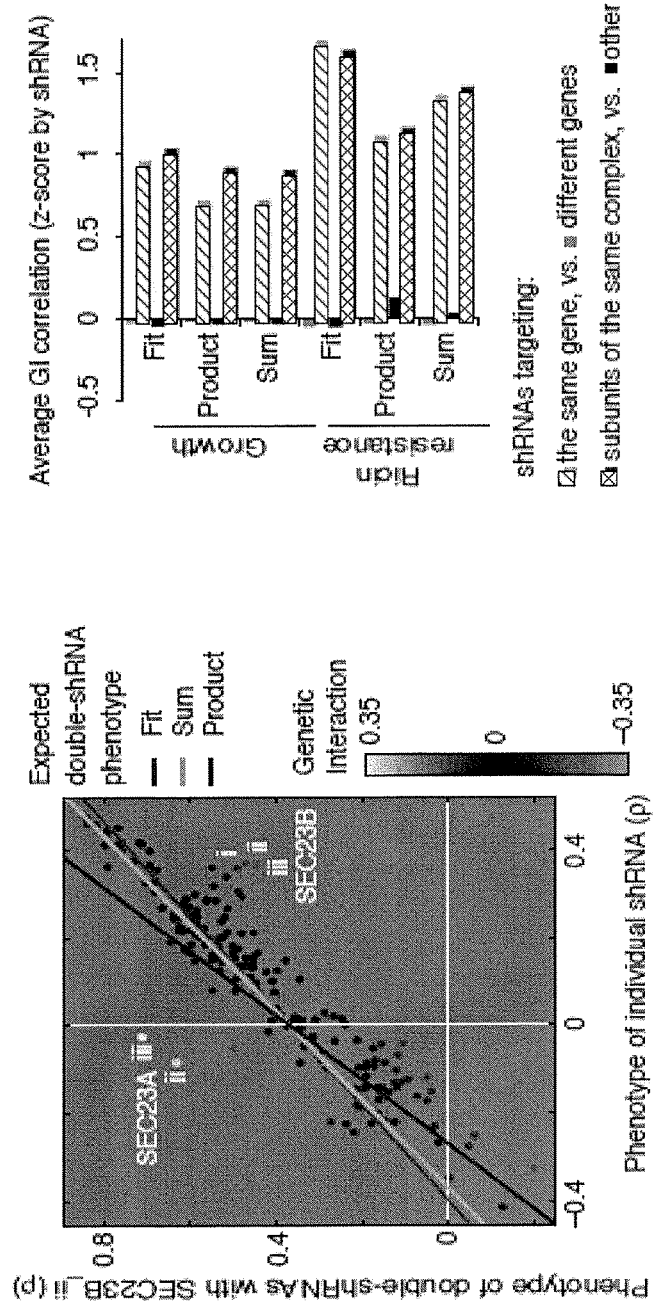

In the case of the ricin resistance screen, the relationship between single shRNA phenotypes and double-shRNA phenotypes in combination with a given "bait" shRNA could adequately be described by a linear function (FIG. 28C and Methods). We fit linear functions for each bait shRNA and compared their slopes with the slopes obtained with the product and sum definitions for expected double-shRNA phenotypes (FIG. 28C). The fit for some baits agreed reasonably well with either the sum or the product model, but it deviated significantly for many others. Intriguingly, fit functions for shRNAs targeting the same gene seemed to have more similar slopes than those for other shRNAs with similar single-shRNA phenotypes, indicating a possible biological relevance of the slopes.

To investigate which of the definitions would yield GIs capturing useful biological information, the average Pearson correlation of GI patterns were compared between pairs of shRNAs targeting either the same genes or genes encoding members of the same known protein complex, and other pairs of shRNAs. It was reasoned that an appropriate definition of GIs should lead to higher GI correlation for intra-gene or intra-complex shRNA pairs than for others, since related functions of genes are typically reflected in similar GI patterns.

For GIs based both on growth and ricin resistance, the fit-based definition resulted in better differentiation of intra-gene and intra-complex shRNA pairs from other shRNA pairs than the product or sum definitions (FIG. 28D). This definition was therefore used for further analysis. It is likely that the best definition for GIs needs to be determined individually for other types of screens; the criterion presented herein is a useful tool to evaluate and compare different possible definitions.

Detection of shRNAs with Partial Off-Target Effects

Figure 29A:
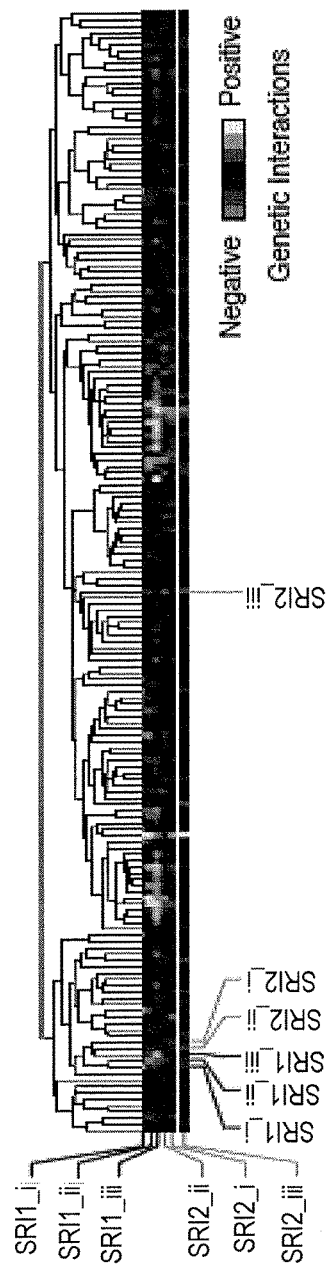
FIGS. 29A-D illustrate that GI correlation detects shRNAs with partial off-target effects. (A-C) Genetic interactions (GIs) were derived from a double-shRNA screen for ricin resistance, and GI patterns are compared for shRNAs targeting the physically interacting proteins SRI1 and SRI2 to detect off-target effects. (A) Hierarchical clustering of GI patterns (excerpt of dataset), heatmap display of GIs from negative to positive. (B) Distribution of correlation coefficients of GI patterns between SRI2_i and all other shRNAs; GI correlations for shRNAs targeting SRI1 and SRI2 are indicated by arrows. (C) GI correlations for all pairwise combinations of shRNAs targeting SRI1 and SRI2, shown as heatmap of z values based on normalization of all GI correlation coefficients for the shRNA denoting the column. Phenotypes of individual shRNAs are listed. (D) Phenotypic strength, as well as shRNA sequence properties summarized in the On-Target Sequence Score are predictive of shRNA off-target propensity. These variables are binned; numbers refer to the upper bounds of the bins, and the last bin contains all cases exceeding the previous bound, where indicated by the > sign. Numbers of shRNAs passing or failing the intra-gene GI correlation cutoff of z=0.8 are shown as orange and grey bars, respectively. The percentage of active shRNAs per bin is indicated by the line. ROC AUC are shown as blue numbers.
Figure 29C:
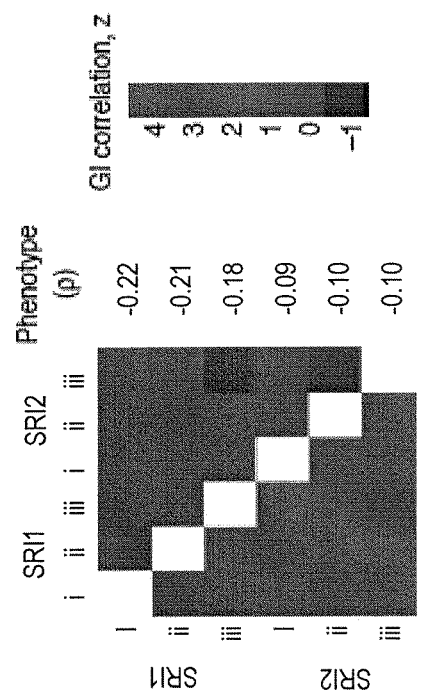
Figure 29B:
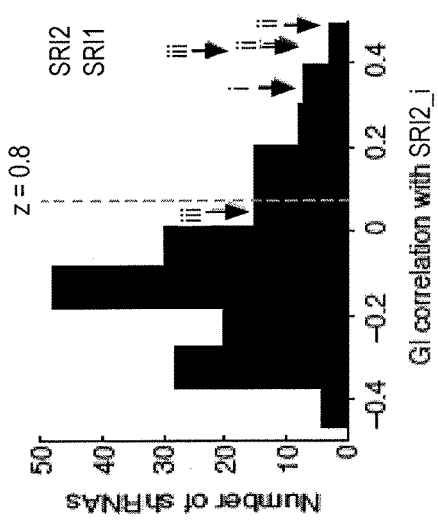

The high Pearson correlation between GI patterns of independent shRNAs targeting the same gene (FIG. 28D) is to be expected if the shRNA phenotypes are predominantly due to depletion of the intended target gene. However, exceptions to this rule were observed for some genes, such as SRI2. Among the three shRNAs targeting SRI2, only the GI patterns for SRI2_i and SRI2_ii were highly correlated; SRI2_iii showed only a partial similarity in the spectrum of GIs, and had a low correlation with both SRI2_i and SRI2_ii (FIG. 29A-C). In cases like these, it was assumed that the highly correlated shRNAs were acting through the intended target, whereas the shRNA with the divergent GI pattern had partial off-target effects. In the case of SRI2, this assumption is supported by the observation that SRI2_i and SRI2_ii also show a more correlated GI pattern than SRI2 iii with shRNAs targeting SRI1 (FIG. 29C); SRI1 and SRI2 encode physically interacting proteins.

To minimize the impact of off-target effects on the GI map, shRNAs that lacked sufficient correlation with the other shRNAs targeting the same gene were excluded from further analysis. To define sufficient correlation, an empirically determined threshold of z=0.8 was chosen on the basis of the normalized distribution of GI correlation coefficients for the shRNA.

Figure 29D:
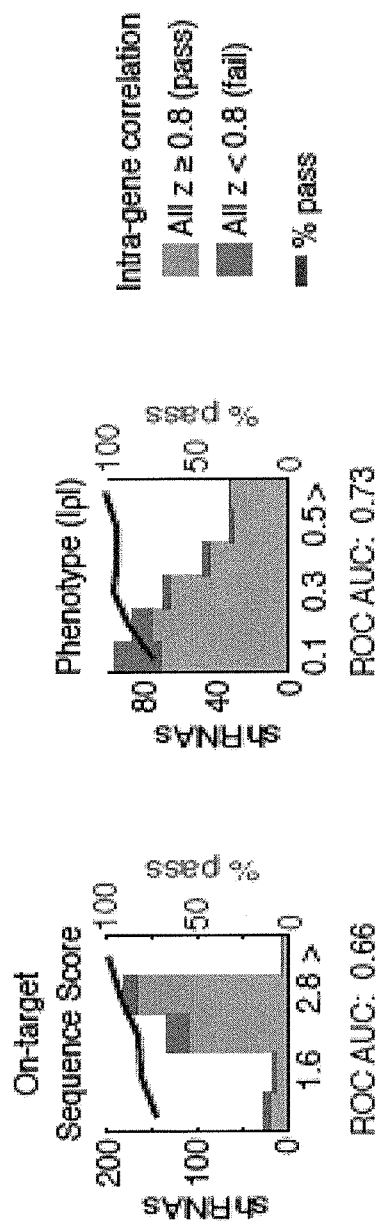

This study investigated whether sequence features of shRNAs would be predictive of the propensity to have partial off-target effects, as detected by a lack of sufficient intra-gene GI correlation. Several sequence features were indeed predictive; most notably, higher A/U content in the 21mer guide strands was correlated with a higher rate of detected off-target effects. Stepwise logistic progression was used to generate an On-Target Sequence Score predicting shRNAs with a lower propensity for off-targets (FIG. 29D).

Insufficient intra-gene correlation was more common for shRNAs with weak phenotypes ($|\rho|<0.2$, FIG. 29D), indicating that low signal-to-noise ratios may be a contributing factor. However, weak phenotypes are not the only cause of insufficient GI correlation, since the predictive On-Target Sequence Score is not strongly correlated with phenotypic strength. In theory, phenotypes for some genes may be dosage-dependent, and different degrees of knockdown of the same may therefore result in different GIs. To investigate whether such effects are widespread, three hit genes were chosen from the ricin resistance screen (VPS53, RAB1A and TRAPPC8) and included ~15 shRNAs targeting each of these genes in our double-shRNA library. For these three genes, all shRNAs showed highly correlated GI patterns irrespective of phenotypic and knockdown strength. Future screens may detect genes with a dosage-dependent switch in GIs.

Definition of Buffering and Synergistic GIs

High-density GI maps not only reveal functional groups of genes based on the correlation of their GI patterns, but they also comprehensively quantify GIs, which can be interpreted directly to gain insight into the nature of the relationship between genes, and ideally reconstruct entire pathways (Phillips 2008; Battle et al. 2010). One classical example of an interpretable GI is the case of two genes that act in parallel pathways and partially compensate for each other's loss. Depletion of either gene product will have a moderate effect; depletion of both will have a much stronger effect, which is typically referred to as synergistic or synthetic sick/synthetic lethal GI. The opposite type of GI is characteristic of genes acting in a linear pathway: depletion of either gene product interferes with the pathway and causes a given phenotype. In combination, depletion of both gene products together has no additive effect on the phenotype, which is referred to as a buffering GI. Genes encoding subunits of a physical complex are often connected by one type of GIs, either buffering or synergistic—a phenomenon referred to as monochromaticity (Segre et al. 2005).

In the case of GIs between genes that have deleterious effects ("negative" phenotypes), positive GIs are buffering and negative GIs are synergistic. Conversely, in the case of GIs between genes that have beneficial effects ("positive" phenotypes), negative GIs are buffering and positive GIs are buffering (Phillips et al. 2000). GIs between genes of mixed phenotypes or with paradoxical double-mutant phenotypes (sometimes referred to as "sign epistasis", Weinreich et al. 2005) are more difficult to interpret. A qualitative classification of different cases of GIs has been proposed (Drees et al. 2005), but to our knowledge, a method for mapping quantitative GIs between mixed-phenotype genes onto a continuum of synergistic to buffering GIs has not previously been developed.

Figure 30A:
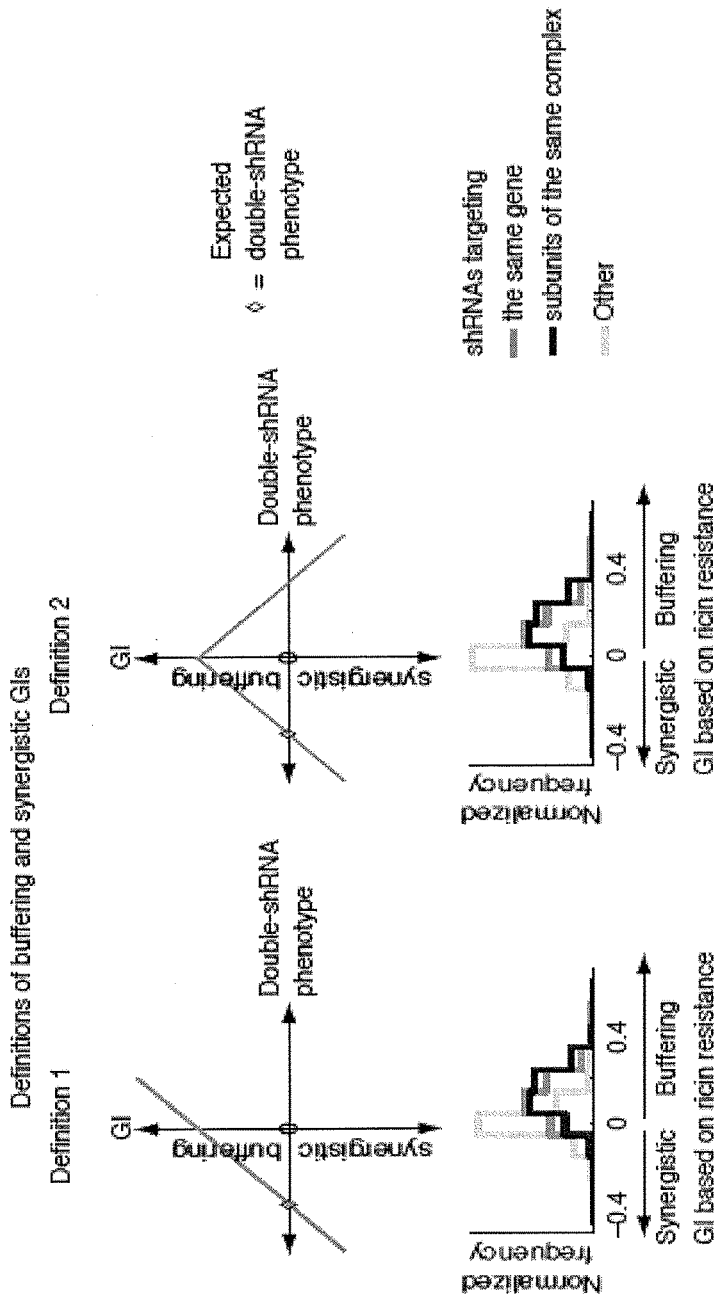
FIGS. 30A-E illustrate that growth-based and differential GI maps reveal protein complexes and pathways. (A) Defining buffering and synergistic genetic interactions (GIs). Top: Two possible definitions (lines) as a function of double-shRNA phenotypes and expected double-shRNA phenotype (diamond). Bottom: Distribution of GIs according to these two definitions between shRNAs targeting the same gene, subunits of the same complex, or other pairs of shRNAs. (B, C) GI maps based on growth and ricin resistance, respectively. Heatmap display of synergistic and buffering GIs. Groups of genes encoding known functionally or physically interacting proteins are labeled on the right. (D, E) Differences in GI correlation patterns between the growth-based GI map and the ricin-resistance-based GI map. (D) GI pattern correlation between ILF2 and the other genes in the GI map (black). Two genes are highlighted: ILF3, which together with ILF2 encodes the two subunits of the NFAT complex, and RPS25, which shows a highly correlated GI pattern with ILF2 only based on ricin resistance. (E) GI pattern correlation between TRAPPC11 and the other genes in the GI map (black). Three genes are highlighted: TRAPPC8, which is proposed to be a member of a specialized TRAPP complex with TRAPPC11, TRAPPC9, which is proposed to be a member of a different specialized TRAPP complex, and TRAPPC1, presumably a constitutive member of all TRAPP complexes. Dissection of the two specialized TRAPP complexes is only possible based on ricin resistance, not simply growth.

This study explored two possible definitions for synergistic and buffering GIs that differ in their interpretation of sign epistasis (FIG. 30A, defined mathematically in the Methods). To evaluate whether these definitions were biologically meaningful, the distribution of buffering and synergistic GIs was determined between shRNAs targeting the same gene, genes encoding subunits of the same complex, and other shRNAs (FIG. 30A). For both definitions, shRNAs targeting the same gene or subunits of complexes were generally connected by buffering GIs, whereas the distribution of GIs for other shRNAs was centered around 0 (FIG. 30A).

Functional Dissection of Pathways and Complexes by Comparative GI Mapping

An important advantage of the pooled screening approach described herein is the ease with which the same double-shRNA library, once constructed, can be screened for different phenotypes, or in different cell lines. GI maps were constructed for the same set of genes based on growth (FIG. 30B) and on ricin resistance (FIG. 30C) by clustering genes based on the Pearson correlation between their GI patterns. Both GI maps recapitulated many known functional groups of genes. These included pathways (such as the small GTPase ARF1 and its nucleotide exchange factor GBF1, or a cluster including ribosomal proteins and a translation initiation factor), as well as physical complexes (such as NFAT, GARP, and the SRI complex).

Figures 30B, 30C:
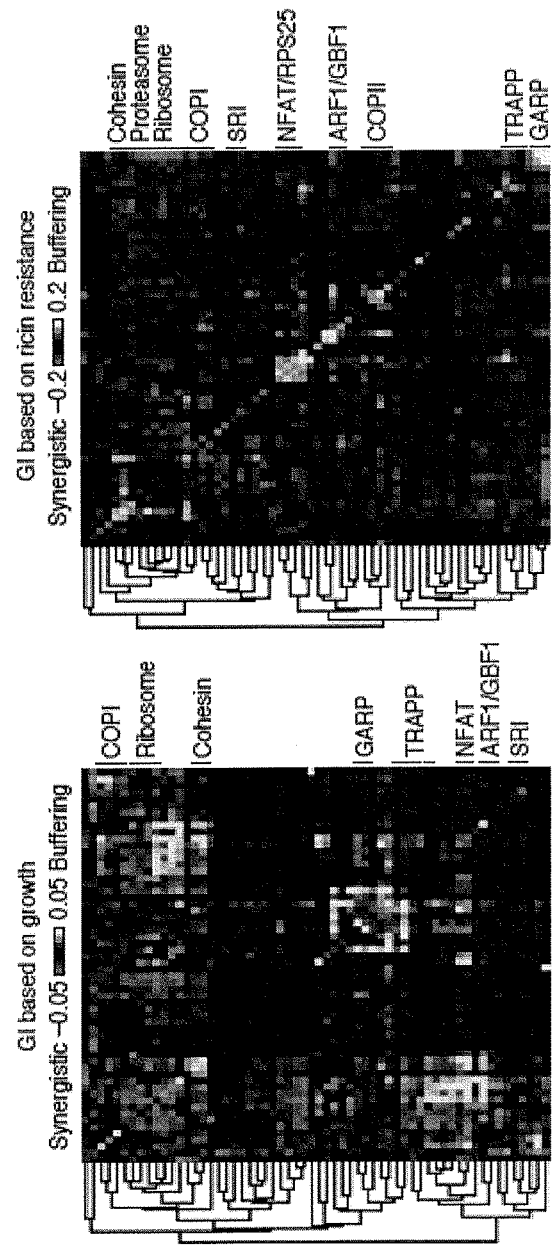

Notably, shRNAs for the double-shRNA library were chosen based on their ricin resistance phenotype (ρ) and some had only very minor effects on growth (γ). Consequently, the amplitude of GIs was much lower for the growth-based GI map than for the ricin resistance based GI map (FIG. 30B,C). Despite the lower signal for individual GIs, correlation between GI patterns was highly reproducible and clustering of related genes in the growth-based GI map was robust (FIG. 30B).

Figures 30D, 30E:
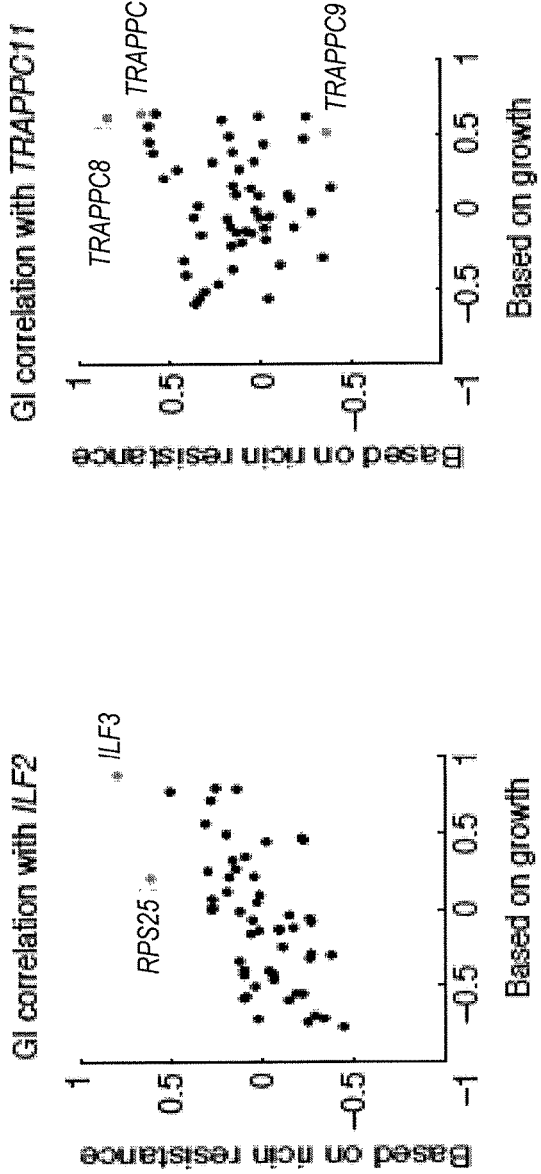

While most GI correlations and clusters were very similar in the growth-based and ricin resistance-based GI maps, there were intriguing exceptions. Surprisingly, knockdown of the small ribosomal subunit RPS25 caused ricin resistance, whereas knockdown of large ribosomal subunits sensitized cells to ricin. In the ricin-based GI map, the GI pattern of RPS25 was highly correlated with ILF2 and ILF3, the genes encoding the two subunits of NFAT, whereas it was mostly uncorrelated in the growth-based GI map (FIG. 30D). Furthermore, RPS25 shows a strongly buffering GI with ILF2 and ILF3 in the ricin-based GI map, but not in the growth-based GI map. Conversely, ILF2 and ILF3 showed highly correlated GI patterns and buffering GIs in both GI maps (FIG. 30D). Together, these results suggest that RPS25 and NFAT function together in ricin-intoxicated cells, but that this functional cooperation either does not take place in the absence of ricin, or that it is not relevant for cell growth.

A second example is the discovery of two functionally distinct TRAPP complexes, containing shared core subunits in addition to either TRAPPC11/TRAPPC8 or TRAPPC9. The clue for the existence of these complexes came from the observation that TRAPPC9 was anti-correlated with other TRAPP components in the ricin-based GI map (FIG. 30E). The functional specialization would not have been detected in the growth-based GI map, where TRAPPC9 correlates with the other TRAPP components (FIG. 30E). While this study could demonstrate biochemically that the distinct TRAPP complexes exist in the absence of ricin, growth as a phenotypic readout was too unspecific to detect their functional differentiation.

These findings illustrate the value of interrogating the same set of GIs under different conditions—a concept previously proposed on the basis of differential GI maps (or "dEMAPs") obtained in yeast by determining growth-based GIs under different conditions and subtracting them from each other (Bandyopadhyay et al. 2010). This study proposes instead to define a differential phenotype (such as ricin resistance, which is quantified by comparing growth in the presence and absence of ricin) and determine GIs based on this differential phenotype. While the resulting map should theoretically be identical to a differential GI map, determination of differential phenotypes for each experimental replicate before calculation of GI maps clearly improves the reproducibility of the resulting GI maps. GI maps based on differential phenotypes also reveal context-dependent pathways more clearly than growth-based GI maps derived from different conditions. In the future, systematic comparison of GI maps obtained for a wide range of specific phenotypes (FIG. 25C) enables important insights into dynamic nature of cellular networks.

Perspective

This example describes the development of an integrated technology platform for functional genomics in mammalian cells based on quantitative pooled shRNA screens. First, genes of interest were identified in a pooled genome-wide screen. Some of the key innovations for the primary screen are the ultra-high coverage (~25 shRNAs/gene) and the extensive set of negative-control shRNAs, which allow the detection of hit genes with great sensitivity and robustness. This study also determined design features of potent shRNAs that together with ongoing efforts by several groups to identify effective shRNAs (Fellmann et al. 2011; Tan et al. 2012) will allow the design of more compact libraries in the future. Second, high-density GI maps were constructed based on pooled screening of a double-shRNA library targeting all combinations of hit genes from the primary screen.

The pooled double-shRNA strategy has several key advantages over approaches in which each gene pair is knocked down in a separate well by a combination of long double stranded RNAs (Horn et al. 2011) or siRNAs. First, pooled screens subject all cells to an identical environment and selective pressure, thus removing major sources of experimental variability. Second, pooled screens can be carried out in standard cell culture vessels, obviating the need for specialized high-throughput equipment for screen setup and phenotype readout. Third, shRNA libraries are a renewable resource and eliminate the requirement to purchase expensive siRNA reagents for each screen. Fourth, the knockdown mediated by siRNAs is transient, whereas cells stably expressing shRNAs can be subjected to longer continuous screens, which are relevant to investigate biological processes such as senescence or proliferation of cancer cells. Fifth, shRNAs can be expressed at levels that do not saturate the cellular RNAi machinery (An et al. 2006), which is an important prerequisite for maintenance of knockdown efficiency in the double-shRNA format, whereas siRNAs can cause side effects by saturating the cellular machinery (Khan et al. 2009). Sixth, pooled screens using suspension cell lines or adherent cell lines growing on microcarriers can be scaled up seamlessly in simple stirrer flasks or more sophisticated bioreactors without increasing the time required for the screen, whereas the time required for the sequential setup and phenotype readout of well-based screens scales linearly with the number of GIs. Since the number of GIs increases as the square of the number of genes under investigation, scalability is a criterium of paramount importance for the construction of larger GI maps. Finally, once a double-shRNA library is constructed, it can rapidly be screened in a variety of cell types (including primary patient cells), or under a variety of different selective pressures (such as different drugs).

This example demonstrates biological findings obtained by comparing GI maps based on different phenotypes (effects on growth versus ricin susceptibility). In the future, comparative GI mapping can provide a three-dimensional data set of genetic interaction across multiple different cell types or primary cells from different individuals, or phenotypic readouts. This could be combined with richer phenotypic read-outs than simple growth (e.g. induction of a transcriptional response, turning on a signaling pathway, switch from latent to lytic phases of a viral infections or cell migration). Together, these should yield fundamental insights both into the rewiring of cellular pathways in different contexts and, conversely, into the functional consequences of complex differences in genetic and epigenetic background.

Methods

Ricin Resistance and Growth Screens

The ricin resistance screens for the genome-wide library, batch retest, and double-shRNA libraries were carried out as described in Example 6. For growth phenotypes, a cell population harvested at $t_0$ was compared to the untreated cells at the end of the screen, which typically lasted ~12 days.

Determination of shRNA Phenotypes from Pooled Screens

During exponential growth, the number of wild-type cells, $N_{WT}$, will increase over time as:

$$N_{WT}(t)=N_{WT}(t_0) \cdot 2^{gt}$$

where g is the growth rate of WT cells (FIG. 26A). The effect of shRNA X on $N_X(t)$, the growth of cells expressing X, was defined as $\gamma_X$, such that $$N_X(t)=N_X(t_0) \cdot 2^{(1+\gamma_X)gt}$$

$\gamma_X$ can be calculated from the change in frequency of cells expressing X compared with WT cells as quantified by deep sequencing:

$$\gamma_X = \frac{1}{gt}\log_2 \frac{N_X(t)/N_{WT}(t)}{N_X(t_0)/N_{WT}(t_0)}$$

Note that the observed growth rates represent the net result of cell proliferation and cell death, and may not always be constant over the time course of the experiment, dependent on the dynamics of the selection procedure. The growth rate of WT cells, g, is determined by exploiting the fact that the cell population contains some fraction of cells (typically 10-20%) that have not been infected with the shRNA-mCherry expressing construct. g is calculated by measuring the growth of the bulk population (using standard cell counting and viability assays) and correcting for growth differences between the WT cells and the bulk population by tracking the fraction of mCherry-negative subpopulation using flow cytometry.

For screens carried out in the presence of selective pressure, a selective pressure k was defined such that:

$$N_{WT}^S(t)=N_{WT}^S(t_0) \cdot 2^{(g-k)t}$$

For k<g, cells grow with a reduced net rate (due to growth inhibition or cell death); for k>g, the population decreases due to net cell death. The resistance that an shRNA X confers to the selective pressure was defined as $\rho_X$, such that $$N_X^S(t)=N_X^S(t_0) \cdot 2^{[(1+\gamma_X)g-(1-\rho_X)k]t}$$

To determine $\rho_X$, frequencies of cells expressing shRNAs are compared in unselected (U) and selected (S) populations:

$$\rho_X = \frac{1}{kt}\log_2 \frac{N_X^S(t)/N_{WT}^S(t)}{N_X^U(t)/N_{WT}^U(t)}$$

Frequencies at $t_0$ need not be measured to calculate $\rho_X$, as long as the unselected and selected populations are separated from a common parent population at $t_0$. However, k needs to be calculated as the reduction in growth rate that WT cells experience under selective conditions compared with standard conditions. Similarly to g (see above), we calculate k by measuring bulk population growth and monitoring the fraction of mCherry-negative cells for both the unselected and selected populations.

In experiments with k≈0, $\rho_X$ is not a useful measure, and instead the differential growth metric $\delta_X$ was used, defined as:

$$\delta_X = \frac{1}{gt}\log_2 \frac{N_X^S(t)/N_{WT}^S(t)}{N_X^U(t)/N_{WT}^U(t)}$$

Selection does not have to be growth-based; it can also rely on physical separation methods such as fluorescence-activated cell sorting or cell migration assays. If the separation is always carried out according to the same protocol, differential enrichment $\varepsilon_X$ represents a directly comparable metric of phenotype:

$$\varepsilon_X = \log_2 \frac{N_X^S(t)/N_{WT}^S(t)}{N_X^U(t)/N_{WT}^U(t)}$$

Machine Learning

A set of bona fide hit genes was defined for ricin susceptibility, which encompassed protective genes up to an FDR of 5%, sensitizing genes up to an FDR of 2%, and genes with at least 2 shRNAs passing the minimal correlation cutoff of z=0.8 in the GI map. shRNAs targeting these hit genes were defined as "active" if their phenotype determined in the batch retest was >0.05 (for protective shRNAs) or <−0.05 (for sensitizing shRNAs), and as "inactive" otherwise. Example 6 shows for selected hit genes that phenotypic activity and on-targed knock-down are generally highly correlated. The Sequence Score and Composite Score predictive of shRNA activity were derived based on this learning set using stepwise logistic regression (Gelman and Hill 2007). For the analyses in FIG. 28C-D, Sequence Scores were derived from subsets of the training sets that did not include the genes to which the Sequence Score was then applied. To derive an On-Target Sequence Score, genes were chosen for which 2 or more shRNAs showed a sufficiently correlated GI pattern (z>=0.8), and these correlated shRNAs formed the set of "on-target" shRNAs, whereas shRNAs against the same genes that failed the correlation threshold formed the set of "off-target" shRNAs. The On-Target Sequence Score was derived for this training set as for the Sequence Score.

Definitions for Expected Double-shRNA Phenotypes

For shRNAs X and Y with individual phenotypes φX and Y (where φ can be γ, ρ or δ as defined above), the expected phenotype for the double-shRNA XY is $\varphi_X+\varphi_Y$ according to the sum definition, and $(1+\varphi_X)\cdot(1+\varphi_Y)-1$ according to the product definition. To derive the expected double-shRNA phenotype from a linear fit, all single-shRNA phenotypes were plotted against the phenotypes of the same shRNAs paired with X, as in FIG. 29B, and fit by linear regression. The linear function $f_X$ was forced to assume $\varphi_X$ for a single-shRNA phenotype of 0 (WT). Thus, the only degree of freedom for each bait was the slope of the linear fit. Similarly, a linear function fY was fit describing the relationship between all single-shRNA phenotypes and the phenotypes of the same shRNAs paired with Y. $f_X(\varphi_Y)$ and $f_Y(\varphi_X)$ were generally similar, and the fit-based expected double-shRNA phenotype was defined as the average of $f_X(\varphi_Y)$ and $f_Y(\varphi_Y)$.

Definitions for GIs

"Raw" GIs:

GI=Observed double-shRNA phenotype−Expected double-shRNA phenotype

Buffering/synergistic GI Definition 1:

Buffering GI=sign(Expected double-shRNA phenotype)×(Expected double-shRNA phenotype−Observed double-shRNA phenotype)

Buffering/synergistic GI Definition 2:

Buffering GI=|Expected double-shRNA phenotype|−|Observed double-shRNA phenotype|

This study investigated whether clustering of genes according to the correlation of buffering/synergistic GIs, as opposed to "raw" GIs, would improve clustering of biologically meaningful groups of genes, but this was not the case for the data set. Therefore, GI maps were created by clustering genes based on "raw" GIs, but colored using a heatmap based on buffering/synergistic GIs (according to Definition 2) to make individual GIs interpretable.

Software

Custom scripts were developed in Python/Numpy for most data analysis and plotting. This study incorporated a Python module for logistic regression by Jeffrey Whitaker. This study used QVALUE (Storey and Tibshirani 2003) for Q value (FDR) calculation. Genes were clustered hierarchically based on Pearson correlation of GIs in Cluster (Eisen et al. 1998) and visualized by TreeView (Saldanha 2004).

REFERENCES

Abecasis, G. R., Auton, A., Brooks, L. D., DePristo, M. A., Durbin, R. M., Handsaker, R. E., Kang, H. M., Marth, G. T., and McVean, G. A. 2012. An integrated map of genetic variation from 1,092 human genomes. Nature 491(7422): 56-65.

Adamson, B., Smogorzewska, A., Sigoillot, F. D., King, R. W., and Elledge, S. J. 2012. A genome-wide homologous recombination screen identifies the RNA-binding protein RBMX as a component of the DNA-damage response. Nat Cell Biol 14(3): 318-328.

Ameres, S. L., Martinez, J., and Schroeder, R. 2007. Molecular basis for target RNA recognition and cleavage by human RISC. Cell 130(1): 101-112.

An, D. S., Qin, F. X., Auyeung, V. C., Mao, S. H., Kung, S. K., Baltimore, D., and Chen, I. S. 2006. Optimization and functional effects of stable short hairpin RNA expression in primary human lymphocytes via lentiviral vectors. Mol Ther 14(4): 494-504.

Bandyopadhyay, S., Mehta, M., Kuo, D., Sung, M. K., Chuang, R., Jaehnig, E. J., Bodenmiller, B., Licon, K., Copeland, W., Shales, M. et al. 2010. Rewiring of genetic networks in response to DNA damage. Science 330 (6009): 1385-1389.

Bassik, M. C., Lebbink, R. J., Churchman, L. S., Ingolia, N. T., Patena, W., Leproust, E. M., Schuldiner, M., Weissman, J. S., and McManus, M. T. 2009. Rapid creation and quantitative monitoring of high coverage shRNA libraries. Nat Methods.

Battle, A., Jonikas, M. C., Walter, P., Weissman, J. S., and Koller, D. 2010. Automated identification of pathways from quantitative genetic interaction data. Mol Syst Biol 6: 379.

Collins, S. R., Miller, K. M., Maas, N. L., Roguev, A., Fillingham, J., Chu, C. S., Schuldiner, M., Gebbia, M., Recht, J., Shales, M. et al. 2007. Functional dissection of protein complexes involved in yeast chromosome biology using a genetic interaction map. Nature 446(7137): 806-810.

Collins, S. R., Schuldiner, M., Krogan, N. J., and Weissman, J. S. 2006. A strategy for extracting and analyzing large-scale quantitative epistatic interaction data. Genome Biol 7(7): R63.

Drees, B. L., Thorsson, V., Carter, G. W., Rives, A. W., Raymond, M. Z., Avila-Campillo, I., Shannon, P., and Galitski, T. 2005. Derivation of genetic interaction networks from quantitative phenotype data. Genome Biol 6(4): R38.

Eisen, M. B., Spellman, P. T., Brown, P. O., and Botstein, D. 1998. Cluster analysis and display of genome-wide expression patterns. Proc Natl Acad Sci USA 95(25): 14863-14868.

Fellmann, C., Zuber, J., McJunkin, K., Chang, K., Malone, C. D., Dickins, R. A., Xu, Q., Hengartner, M. O., Elledge, S. J., Hannon, G. J. et al. 2011. Functional identification of optimized RNAi triggers using a massively parallel sensor assay. Mol Cell 41(6): 733-746.

Frost, A., Elgort, M. G., Brandman, O., Ives, C., Collins, S. R., Miller-Vedam, L., Weibezahn, J., Hein, M. Y., Poser, I., Mann, M. et al. 2012. Functional Repurposing Revealed by Comparing S. pombe and S. cerevisiae Genetic Interactions. Cell 149(6): 1339-1352.

Gelman, A. and Hill, J. 2007. Data analysis using regression and multilevel/hierarchical models. Cambridge University Press, Cambridge; New York.

Gu, S., Jin, L., Zhang, Y., Huang, Y., Zhang, F., Valdmanis, P. N., and Kay, M. A. 2012. The Loop Position of shRNAs and Pre-miRNAs Is Critical for the Accuracy of Dicer Processing In Vivo. Cell 151(4): 900-911.

Horn, T., Sandmann, T., Fischer, B., Axelsson, E., Huber, W., and Boutros, M. 2011. Mapping of signaling networks through synthetic genetic interaction analysis by RNAi. Nat Methods 8(4): 341-346.

Jonikas, M. C., Collins, S. R., Denic, V., Oh, E., Quan, E. M., Schmid, V., Weibezahn, J., Schwappach, B., Walter, P., Weissman, J. S. et al. 2009. Comprehensive characterization of genes required for protein folding in the endoplasmic reticulum. Science 323(5922): 1693-1697.

Kaelin, W. G., Jr. 2012. Molecular biology. Use and abuse of RNAi to study mammalian gene function. Science 337(6093): 421-422.

Khan, A. A., Betel, D., Miller, M. L., Sander, C., Leslie, C. S., and Marks, D. S. 2009. Transfection of small RNAs globally perturbs gene regulation by endogenous microRNAs. Nat Biotechnol 27(6): 549-555.

Lander, E. S. Linton, L. M. Birren, B. Nusbaum, C. Zody, M. C. Baldwin, J. Devon, K. Dewar, K. Doyle, M. FitzHugh, W. et al. 2001. Initial sequencing and analysis of the human genome. Nature 409(6822): 860-921.

Luo, B., Cheung, H. W., Subramanian, A., Sharifnia, T., Okamoto, M., Yang, X., Hinkle, G., Boehm, J. S., Beroukhim, R., Weir, B. A. et al. 2008. Highly parallel identification of essential genes in cancer cells. Proc Natl Acad Sci USA 105(51): 20380-20385.

Mani, R., St Onge, R. P., Hartman, J. L.t., Giaever, G., and Roth, F. P. 2008. Defining genetic interaction. Proc Natl Acad Sci USA 105(9): 3461-3466.

Mardis, E. R. 2012. Genome sequencing and cancer. Curr Opin Genet Dev 22(3): 245-250.

Markham, N. R. and Zuker, M. 2005. DINAMelt web server for nucleic acid melting prediction. Nucleic Acids Res 33(Web Server issue): W577-581.

Matveeva, O. V., Kang, Y., Spiridonov, A. N., Saetrom, P., Nemtsov, V. A., Ogurtsov, A. Y., Nechipurenko, Y. D., and Shabalina, S. A. 2010. Optimization of duplex stability and terminal asymmetry for shRNA design. PLoS One 5(4): e10180.

Paddison, P. J., Cleary, M., Silva, J. M., Chang, K., Sheth, N., Sachidanandam, R., and Hannon, G. J. 2004. Cloning of short hairpin RNAs for gene knockdown in mammalian cells. Nat Methods 1(2): 163-167.

Pan, X., Yuan, D. S., Xiang, D., Wang, X., Sookhai-Mahadeo, S., Bader, J. S., Hieter, P., Spencer, F., and Boeke, J. D. 2004. A robust toolkit for functional profiling of the yeast genome. Mol Cell 16(3): 487-496.

Phillips, P. C. 2008. Epistasis—the essential role of gene interactions in the structure and evolution of genetic systems. Nat Rev Genet 9(11): 855-867.

Phillips, P. C., Otto, S. P., and Whitlock, M. C. 2000. Beyond the Average—The Evolutionary Importance of Gene Interactions and Variability of Epistatic Effects. in Epistasis and the evolutionary process (ed. J. B. Wolf, E. D. Brodie, and M. J. Wade). Oxford University Press, Oxford [England]; New York.

Pierce, S. E., Davis, R. W., Nislow, C., and Giaever, G. 2007. Genome-wide analysis of barcoded *Saccharomyces cerevisiae* gene-deletion mutants in pooled cultures. Nat Protoc 2(11): 2958-2974.

Roguev, A., Bandyopadhyay, S., Zofall, M., Zhang, K., Fischer, T., Collins, S. R., Qu, H., Shales, M., Park, H. O., Hayles, J. et al. 2008. Conservation and rewiring of functional modules revealed by an epistasis map in fission yeast. Science 322(5900): 405-410.

Saldanha, A. J. 2004. Java Treeview—extensible visualization of microarray data. Bioinformatics 20(17): 3246-3248.

Schuldiner, M., Collins, S. R., Thompson, N. J., Denic, V., Bhamidipati, A., Punna, T., Ihmels, J., Andrews, B., Boone, C., Greenblatt, J. F. et al. 2005. Exploration of the function and organization of the yeast early secretory pathway through an epistatic miniarray profile. Cell 123 (3): 507-519.

Schultz, N., Marenstein, D. R., De Angelis, D. A., Wang, W. Q., Nelander, S., Jacobsen, A., Marks, D. S., Massague, J., and Sander, C. 2011. Off-target effects dominate a large-scale RNAi screen for modulators of the TGF-beta pathway and reveal microRNA regulation of TGFBR2. Silence 2: 3.

Segre, D., Deluna, A., Church, G. M., and Kishony, R. 2005. Modular epistasis in yeast metabolism. Nat Genet 37(1): 77-83.

Storey, J. D. and Tibshirani, R. 2003. Statistical significance for genomewide studies. Proc Natl Acad Sci USA 100 (16): 9440-9445.

Tan, X., Lu, Z. J., Gao, G., Xu, Q., Hu, L., Fellmann, C., Li, M. Z., Qu, H., Lowe, S. W., Hannon, G. J. et al. 2012. Tiling genomes of pathogenic viruses identifies potent antiviral shRNAs and reveals a role for secondary structure in shRNA efficacy. Proc Natl Acad Sci USA 109(3): 869-874.

Tong, A. H., Evangelista, M., Parsons, A. B., Xu, H., Bader, G. D., Page, N., Robinson, M., Raghibizadeh, S., Hogue, C. W., Bussey, H. et al. 2001. Systematic genetic analysis with ordered arrays of yeast deletion mutants. Science 294(5550): 2364-2368.

Tong, A. H., Lesage, G., Bader, G. D., Ding, H., Xu, H., Xin, X., Young, J., Berriz, G. F., Brost, R. L., Chang, M. et al. 2004. Global mapping of the yeast genetic interaction network. Science 303(5659): 808-813.

Venter, J. C. Adams, M. D. Myers, E. W. Li, P. W. Mural, R. J. Sutton, G. G. Smith, H. O. Yandell, M. Evans, C. A. Holt, R. A. et al. 2001. The sequence of the human genome. Science 291(5507): 1304-1351.

Weinreich, D. M., Watson, R. A., and Chao, L. 2005. Perspective: Sign epistasis and genetic constraint on evolutionary trajectories. Evolution 59(6): 1165-1174.

Example 6. A Systematic Mammalian Genetic Interaction Map Reveals Pathways Underlying Ricin Susceptibility Summary Genetic interaction (GI) maps, comprising pairwise measures of how strongly the function of one gene depends on the presence of a second, have enabled the systematic exploration of gene function in microorganisms. This example describes a two-stage strategy to construct high-density GI maps in mammalian cells. First, ultra-complex pooled shRNA libraries (25 shRNAs/gene) are used to identify high confidence hit genes for a given phenotype and effective shRNAs. Double-shRNA libraries are then constructed from these to systematically measure GIs between hits. As a non-limiting example, a GI map focused on ricin susceptibility broadly recapitulates known pathways and provides many unexpected insights. These include a noncanonical role for COPI, a novel protein complex (SRIC) affecting toxin clearance, a specialized role for the ribosomal protein RPS25, and functionally distinct mammalian TRAPP complexes. Thus, the ability to rapidly generate mammalian GI maps provides a transformative tool for defining gene function and designing combination therapies based on synergistic pairs.

Introduction

Analysis of mammalian genomic sequences provides a parts list of the proteins that comprise a cell. The remaining challenge is to define functions for these parts and understand how they act together. Work in model organisms, especially budding yeast, has demonstrated the broad utility of comprehensive genetic interaction (GI) maps in defining gene function in a systematic and unbiased manner (Collins et al., 2009; Dixon et al., 2009). GIs, which measure the extent to which the phenotype of a first mutation is modified by the presence of a second, reveal functional relationships between genes. Additionally, the pattern of GIs of a gene provides an information-rich description of its phenotype, which can be used to detect functional similarities between genes and reveal pathways without prior assumptions about cellular functions.

Systematic quantitative analysis of GIs in yeast has allowed rapid identification of new functional complexes, predicted roles for uncharacterized genes, revealed network rewiring in response to environmental changes, and demonstrated functional repurposing of complexes and interactions during evolution (Bandyopadhyay et al., 2010; Collins et al., 2009; Dixon et al., 2009; Frost et al., 2012). More recently, GI maps have also been used with great success in Gram-negative bacteria, fission yeast, and cultured cells from fruit flies (Butland et al., 2008; Frost et al., 2012; Horn et al., 2011; Ryan et al., 2012; Typas et al., 2008).

In mammalian cells, an approach for systematic mapping of GIs could have broad utility for unbiased functional annotation of the human genome as well as for targeted investigation of mammalian-specific pathways. More generally, a better understanding of the structure of GIs may clarify the complex heritability of common traits (Zuk et al., 2012). Furthermore, GIs are important in both the pathogenesis and treatment of a number of human diseases, such as cancer (Ashworth et al., 2011). For example, pairs of genes that exhibit synthetic lethality in cancer cells, but not healthy cells, are ideal targets for combination therapies aimed at limiting the emergence of drug resistance in rapidly evolving cells.

A number of challenges confront any effort to systematically quantify GIs. First, high-precision phenotypic measurements are needed to accurately determine GIs, which are quantified as the deviation of an observed double-mutant phenotype from that expected from two individual mutants. Second, GIs are typically rare (Collins et al., 2009; Dixon et al., 2009), and therefore a scalable high-throughput approach is required to generate large, high-density GI maps. At the same time, the large number of possible pairwise interactions in the human genome ($\sim 4 \times 10^8$) makes it necessary to focus on a subset of genes with common biological functions to create a sufficiently dense GI map to reveal meaningful insights.

Recent developments in screening technologies have laid the groundwork for systematic forward genetics in mammalian cells. Both short-hairpin (sh)RNA-based RNAi and haploid insertion approaches lend themselves to pooled screening, which, when combined with deep sequencing-based readouts (Bassik et al., 2009; Carette et al., 2011; Silva et al., 2008), allows massive multiplexing and provides a controlled, identical environment for all cells. Nevertheless, the extraction of robust biological information from genome-wide screening data is challenging (Kaelin, 2012); for RNAi-based screens in particular, the problems of false-positive hits caused by off-target effects and false-negative hits caused by ineffective RNAi agents can limit reliability. Despite these challenges, screens for modifiers of single genes have demonstrated the value of investigating GIs by RNAi (Barbie et al., 2009; Luo et al., 2009).

The present inventors have developed a scalable, high-precision pooled shRNA-based approach for robustly conducting RNAi-based screens and measuring GIs in high throughput in mammalian cells. The methods described herein were used to examine genetic modifiers of cellular susceptibility to ricin. Ricin is a member of a broad class of AB-type protein toxins that includes major human pathogens. Similar to many viral pathogens, these toxins enter cells by endocytosis and hijack intracellular trafficking pathways. While medically important in their own right, these agents have also been used with great success to probe various aspects of cell biology (Johannes and Popoff, 2008; Spooner and Lord, 2012). Since the general biology of ricin has been extensively studied, it is well-suited to evaluate screening approaches. Indeed, several recent screens have been conducted to identify factors whose depletion protects against AB-toxins (Carette et al., 2009; Guimaraes et al., 2011; Moreau et al., 2011; Pawar et al., 2011). Nonetheless, a comprehensive understanding of the pathways exploited by ricin is missing and little is known about factors whose loss enhances ricin toxicity.

In a primary genome-wide screen for modifiers of ricin susceptibility, ~200 known and novel factors which either sensitized or protected cells against ricin intoxication were found; with some interesting exceptions, these factors were remarkably well-focused on the retrograde transport pathway. Functional relationships among these genes were then defined in a GI map. These studies could broadly recapitulate existing complexes and pathways, functionally dissect multi-protein complexes, identify new complexes with uncharacterized components, and provide unexpected insights into the functions of well-characterized genes. More broadly, this work establishes a strategy that integrates a robust method for RNAi screening with scalable, systematic analysis of GIs, which should be applicable to diverse biological problems.

Results and Discussion

Strategy for Primary Screens Using Ultra-Complex shRNA Libraries

The first step in the strategy is to conduct a genome-wide screen to identify genes that function within a biological pathway of interest, and effective shRNAs that target them, using ultra-complex shRNA libraries. Ultra-complex libraries increase the likelihood of targeting each gene with several effective shRNAs, thus reducing the false-negative rate. Additionally, requiring several active shRNAs to identify a hit gene reduces the rate of false-positives, since it is unlikely that several shRNAs targeting a non-hit gene have off-target effects relevant to the phenotype of interest. Two key technical developments enable ultra-high-coverage screening: the ability to construct ultra-complex libraries using massively parallel oligonucleotide synthesis (Cleary et al., 2004; Silva et al., 2005), and the capacity of deep sequencing to monitor screening results (Bassik et al., 2009; Silva et al., 2008).

To determine the best design for a genome-wide ultra-complex shRNA library, a pilot screen was conducted with a limited library targeting 1,000 genes with 50 shRNAs each. Ricin was chosen as a selective agent for our screen, since it efficiently kills cells and relies on numerous host cell factors for its toxicity. In the pilot library, shRNAs targeting a number of genes that were previously reported to affect ricin sensitivity were included. In addition, more than 1,000 negative control shRNAs were included that had the same overall base composition as the other shRNAs in the library, but that did not match the sequence of any human transcript.

Figure 31A:
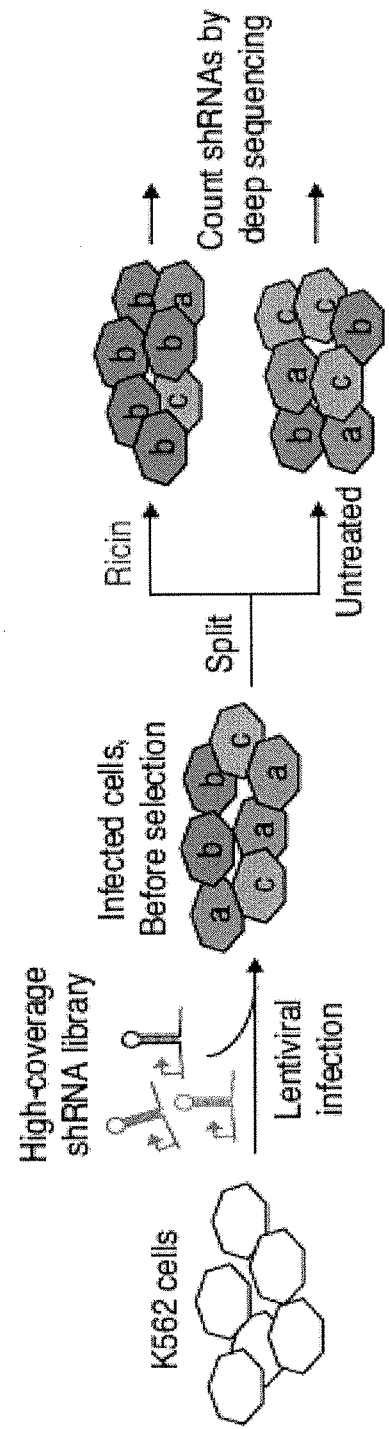
FIGS. 31A-D illustrate a pooled high-coverage RNAi screen for ricin resistance and sensitization. (A) Experimental strategy: A population of K562 cells was infected with a pooled high-coverage shRNA library and split into two subpopulations, one of which was treated with ricin. The frequency of shRNA-encoding constructs in each subpopulation was determined by deep sequencing. (B) Based on the frequency in the treated and untreated subpopulations, a quantitative resistance phenotype ρ was calculated for each shRNA. Comparing the distribution of ρs for shRNAs targeting a gene of interest to the ρ distribution for negative control shRNAs using the Mann-Whitney Utest yielded a P value for the gene. RAB1B knockdown protects cells from ricin ($P=6.9 \cdot 10^{-8}$) whereas knockdown of COPA sensitizes cells to ricin ($P=2.4 \cdot 10^{-8}$). (C, D) Increasing the coverage of the shRNA library improves the detection of hit genes above background. P values for each gene in a test library were calculated on the basis of random subsets of the data; the number of shRNAs included per gene was varied. Random subsampling was repeated 100 times; means of $-\log 10$ P values are shown. Gray dotted lines indicated a coverage of 25 shRNAs per gene, which we chose for our genome-wide library. (C) Means of $-\log 10$ P values +/−SD for three example genes: a strong hit (RAB1A), a moderate hit (STX16), and a non-hit (CRYAB). (D) Means of $-\log 10$ P values for all 1,079 genes targeted by the library (left panel) and for the top 50 hits based on the P value calculated from 45 shRNAs (right panel).

K562 human myelogenous leukemia cells were infected with these libraries and one half of the population was subjected to four pulses of ricin treatment, while the other half was grown in the absence of ricin. After 12 days, genomic DNA was isolated from cells of the treated and untreated populations, the shRNA-encoding cassettes were PCR-amplified, and their frequencies were quantified by deep sequencing (FIG. 31A).

Figure 31B:
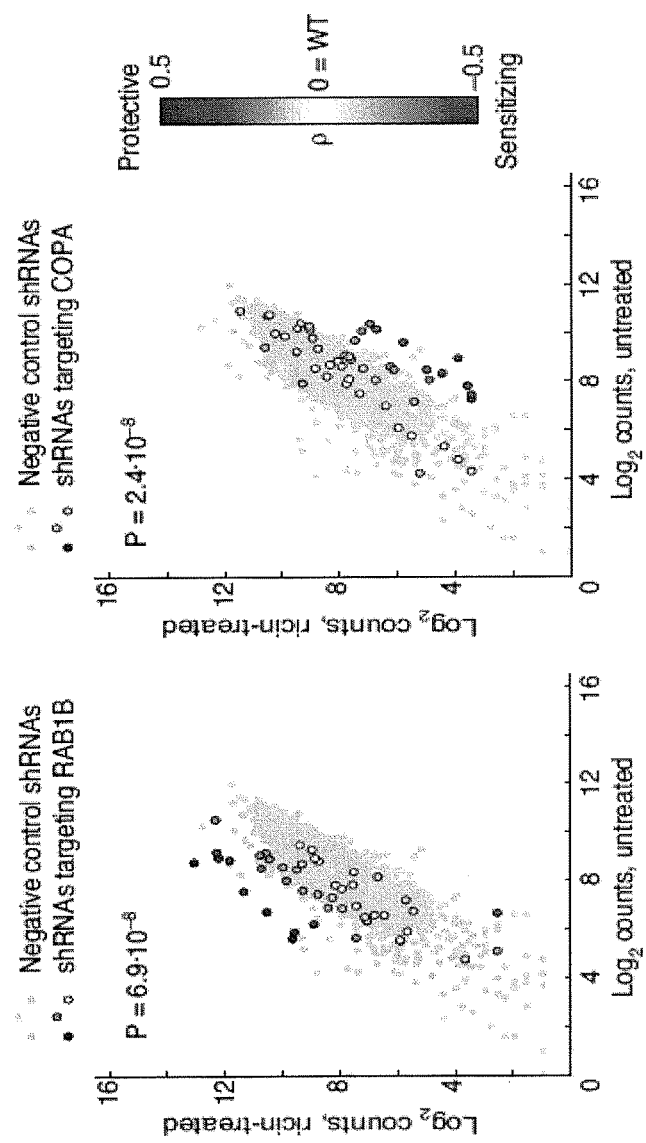

Comparison of the frequency of each shRNA in the treated and untreated populations yielded an enrichment ratio. To enable direct comparisons between different experiments, we defined a metric $\rho$ for ricin resistance, which quantifies the differential effect an shRNA has on cell growth in the presence versus absence of ricin. An shRNA without effect on ricin sensitivity has a $\rho$ of 0; shRNAs conferring ricin resistance have positive $\rho$ values; and shRNAs sensitizing cells to ricin have negative $\rho$ values. The criterion for hit genes was based on a P value which reports on the probability that the distribution of $\rho$s for all shRNAs targeting a given gene was significantly different from the distribution for negative control shRNAs (reflecting both random noise and off-target effects), as tested by the Mann-Whitney U test (FIG. 31B). The robustness of this approach is supported by the agreement of hit genes obtained when two independent shRNA libraries targeting the same genes but using different shRNA designs and target sites were constructed and screened.

Figures 31C, 31D:
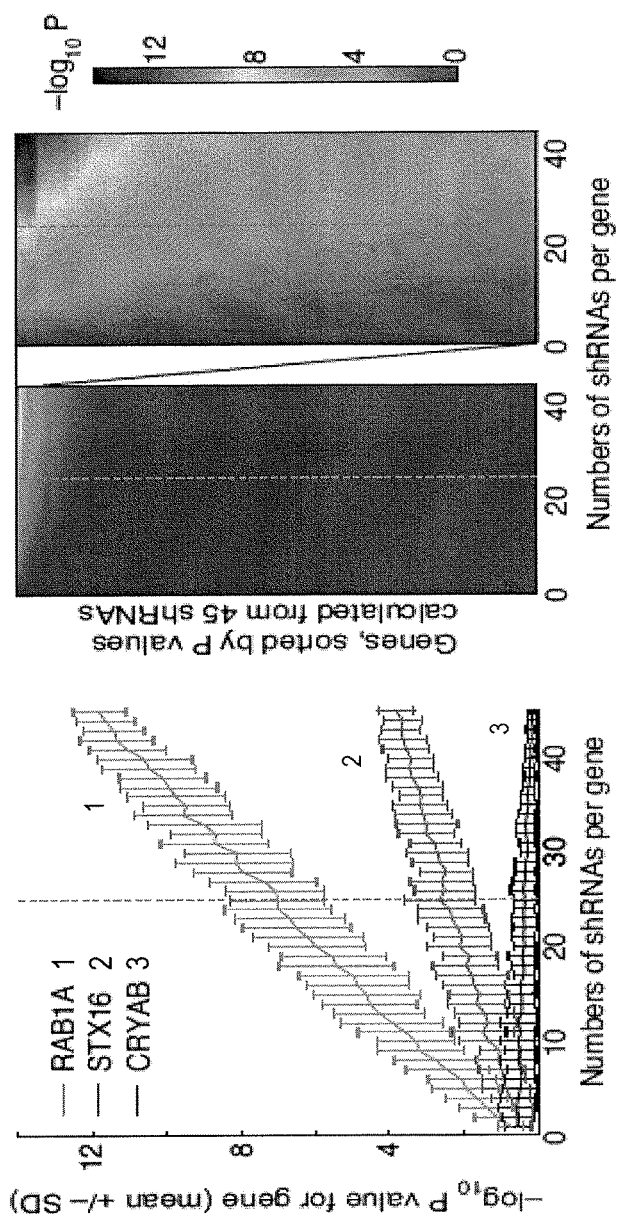

To identify an appropriate complexity for a genome-wide library, the present study examined how the number of shRNAs targeting each gene affects the confidence of hit detection. Specifically, this study calculated P values based on random subsets of shRNAs for each gene, and determined the effect of subset size on the P value for three example genes: the strong hit gene RAB1A, the weaker hit gene STX16, and the non-hit gene CRYAB (FIG. 31C). In this experimental system, the ability to confidently resolve STX16 from background began at ~15 shRNAs per gene and increased steadily as more shRNAs were included. These examples are representative of the entire spectrum of genes (FIG. 31D): increasing the coverage of shRNAs per gene improved the signal for hits without spuriously increasing P values for non-hits. Based on these results, a coverage of 25 shRNAs per gene was chosen for a genome-wide library.

Reproducibility and Performance of Ultra-Complex Libraries in a Pilot Ricin Screen To test the ability of the screening approach to identify effective shRNAs targeting hit genes, the ricin resistance pilot screen was carried out in duplicate. The quantitative phenotypes of shRNAs targeting hit genes correlated reasonably well between replicates. A main source of noise in pooled screens is thought to be Poisson sampling error originating from repeated passaging of cells through a population bottleneck (Pierce et al., 2007). Indeed, conducting a batch retest of shRNAs chosen based on primary screen results with a coverage of ~50,000 cells per shRNA species, as compared with 1,000 cells per shRNA during the primary screen, strongly suppressed the level of observed variability. In future screens, a small-scale (2 liter) bioreactor should allow one to conduct an entire primary genome-wide screen in a single batch of suspension cells with 4,000-fold coverage of cells per shRNA.

The phenotypes for individual shRNAs were validated in a pooled batch retest, or in individual competitive growth assays. These two quantitative assays gave highly correlated results. Generally, the phenotypic strength of shRNAs targeting a given hit gene also correlated well with the efficiency of target mRNA knockdown, indicating that shRNAs were predominantly acting through the intended target.

A Genome-Wide, High-Coverage shRNA Screen for Modifiers of Ricin Toxicity Yields Diverse Hits Focused on Key Pathways Next, a library targeting each annotated human protein-coding gene was designed with 25 independent shRNAs on average, as well as at least 500 negative control shRNAs per experiment. The shRNAs were grouped in 9 sublibraries of 55,000 shRNAs each, based on annotated biological functions.

For a first application of the genome-wide screening approach, ricin was also used, as it should give access to the rich biology of host pathways exploited by this toxin (Lord et al., 2005; Sandvig et al., 2010; Spooner and Lord, 2012). Specifically, ricin is internalized by endocytosis and traffics retrogradely through the secretory pathway to the ER, where its A and B subunits are dissociated. The catalytic A subunit is then retrotranslocated to the cytoplasm where it depurinates a single base in the 28S rRNA, shutting down translation and leading to apoptosis (FIG. 18A).

A set of hit genes was defined based on false discovery rate (FDR, Storey and Tibshirani, 2003); this set contained the 73 strongest protective hits (FDR<0.05) and the 83 strongest sensitizing hits (FDR<0.02). These hits were strongly enriched for genes related to trafficking along the secretory pathway (FIG. 18B). FIG. 18C displays the top hits in their canonical cellular context. A large fraction of characterized hits were either genes acting in the secretory pathway, or otherwise expected based on known ricin biology. In addition, several poorly characterized hit genes were tagged with GFP, expressed from their native chromosomal context in BACs (Poser et al., 2008), and confirmed that they were localized to secretory pathway organelles. It was found that many of the top hits in the screen are also known to exist in physical complexes with each other, with strong protection upon knockdown of components of COPII, TRAPP, and GARP, and strong sensitization upon knockdown of components of COPI, the ribosome, and the proteasome. Taken together, the above results illustrate the specificity and robustness of the hits identified by this approach.

Consistent with the results from previous ricin screens and individual gene studies, it was found that the early endocytic factors clathrin and Rab5 (Moreau et al., 2011) were required for ricin toxicity, as well as STX16, a snare protein involved in vesicle fusion at the TGN (Amessou et al., 2007). Among the most strongly enriched were components of the GARP complex, known to be required for tethering endosome-derived vesicles to the Golgi (Bonifacino and Hierro, 2011). Knockdown of several (but not all, see below) components of the vesicle tethering TRAPP complex were among the most strongly protective factors.

Surprisingly, a large number of components of the COPII machinery required for anterograde vesicle budding from the ER were strongly protective against ricin when knocked down, which has not been previously observed. It is likely that shutdown of ER-Golgi trafficking (and consequent Golgi collapse) prevents ER delivery of ricin.

Depletion of ribosomal components and ribosome biogenesis factors sensitized cells to the toxin, as expected given that ricin targets the ribosome. A notable exception was RPS25, whose knockdown was strongly protective against ricin, as discussed below.

Identification of Atorvastatin as a Small-Molecule Inhibitor of Ricin Transport to the ER One goal of RNAi-based forward genetic screens is to identify therapeutically valuable targets for small molecule inhibitors. Consistent with previous studies (Grimmer et al., 2000), this primary screen identified components of the cholesterol biosynthesis pathway, including HMG-CoA reductase (HMGCR). A dose-dependent protection of ricin-treated cells by the HMGCR inhibitor atorvastatin was observed (FIG. 32A), confirming the role of HMGCR in modulating the toxicity of ricin, and demonstrating that the primary screen could identify effective pharmacological targets.

To assess whether inhibition of HMGCR by atorvastatin affected delivery of ricin to the ER, an ER-targeted SNAP protein (Geiger et al., 2011) was expressed in cells and benzylguanine (BG)-coupled ricin was added to measure ricin flux into the ER. Upon delivery of toxin to the ER, an irreversible bond can form between ricin-BG and ER-SNAP, which could be quantified as an increase in molecular weight by Western blot (FIG. 32B). The fraction of SNAP present in ricin conjugates was reduced by ~80% upon treatment with atorvastatin (FIG. 32B-C), indicating that toxin traffic to the ER was blocked upon HMGCR inhibition.

A Paradoxical Role for COPI in Diverting Ricin from the ER

One of the more surprising results from the primary screen was a profound sensitization to ricin upon depletion of COPI components (FIG. 18C), which are normally involved in retrograde endosome-Golgi and Golgi-ER transport (Popoff et al., 2011). Several groups have observed a lack of requirement for retrograde COPI components in trafficking of ricin or Shiga toxin (Chen et al., 2002; Girod et al., 1999; Llorente et al., 2003). However, sensitization by COPI depletion or inactivation has not been described previously.

Primary hits from the ricin screen were retested in batch in a second cell type (Raji B) for their effects on sensitivity to both ricin and Shiga toxin, a similar AB toxin. Again, sensitization to ricin upon COPI knockdown was observed, but strong protection against Shiga toxin, revealing an unexpected difference between the trafficking pathways of these two well-studied toxins. Individual shRNAs targeting COPI components ARCN1 or COPZ1 confirmed this finding (FIG. 32D). This divergent set of requirements was the exception, rather than the rule: ARF1 is a representative factor that protected against both toxins (FIG. 32D). COPI depletion enhanced delivery of toxin to the ER based on the SNAP assay (FIG. 32E). It may be that COPI knockdown upregulates a compensatory alternative pathway, or that it normally functions in transport steps that divert ricin from ER.

A Strategy for Generating High-Density GI Maps Based on Double-shRNA Screens

Figure 33A:
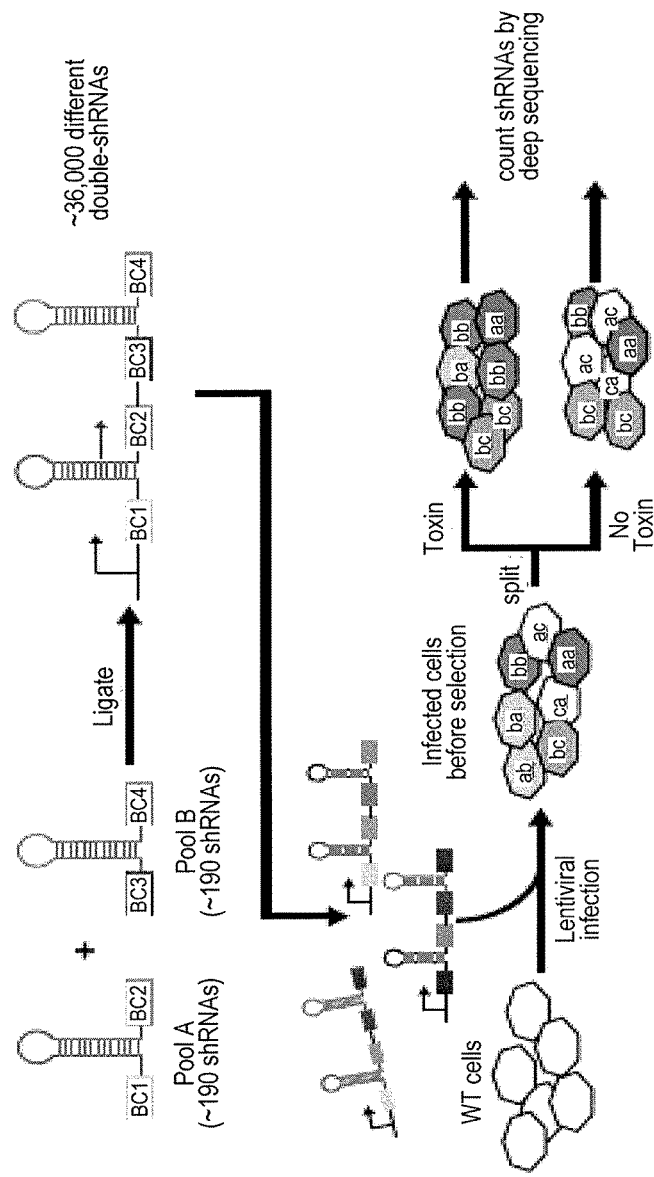

While the screen described herein accurately identified genes important for ricin pathology, the large number of hits makes individual validation and characterization challenging. Indeed, the difficulty in pinpointing promising hits for in-depth follow up represents a general bottleneck for the interpretation of RNAi screens. To address this issue, a strategy was developed to systematically determine GIs between the hits based on double-knockdown phenotypes. For this purpose, a double-shRNA library was created based on effective shRNAs identified from the primary screen. shRNA-encoding cassettes were individually barcoded, pooled and ligated to obtain all pairwise combinations (FIG. 33A). This double-shRNA library was introduced into cells and subjected to a ricin resistance screen under the same conditions as those in the primary screen to quantify double-shRNA phenotypes.

In order to obtain single-shRNA phenotypes from the same screen, 12 negative control shRNAs were included in the double-shRNA library pool. Importantly, phenotypes of single shRNAs as quantified by batch retest were in excellent agreement with phenotypes of double shRNAs combining the same shRNAs with negative control shRNAs (FIG. 33B). Moreover, the presence of a second shRNA and the order of shRNAs within the double-shRNA construct had minimal impact on the measured phenotypes (FIG. 33C) or knockdown efficiency.

It was found that the typical phenotype of a given double shRNA could be reliably predicted by a linear relationship of the phenotypes of the two individual shRNAs (FIG. 33D). GIs were thus quantified as deviations from the linear fit of this typical double-mutant phenotype. Deviations towards the phenotype of WT cells were defined as buffering GIs, and deviations away from WT were defined as synergistic GIs. As expected, two shRNAs targeting the same gene typically showed buffering GIs (e.g., SEC23B in FIG. 33D), whereas synergistic GIs could be observed for some shRNAs targeting genes acting in parallel (e.g., shRNAs targeting SEC23A and SEC23B, two isoforms with partially distinct functions (Fromme et al., 2008; Schwarz et al., 2009), in FIG. 33D). GIs observed in the pooled double-shRNA screen could also be reproduced in individual validation experiments. For example, SEC23A and SEC23B knockdown (whose specificity was validated by rescue experiments) synergized to create highly ricin-resistant cells as monitored by the competitive growth assay (FIG. 33E). A similar synergistic effect was seen when the amount of ricin reaching the ER was assessed by ER-SNAP assay (FIG. 33F).

Construction and Benchmarking of a Ricin GI Map

A major motivation for systematic GI mapping beyond the direct analysis of pairwise interactions between genes is the possibility to analyze the correlation of global GI patterns between different genes. Genes with highly correlated GI patterns tend to be functionally related (Collins et al., 2009; Dixon et al., 2009).

Figures 20A, 20B:
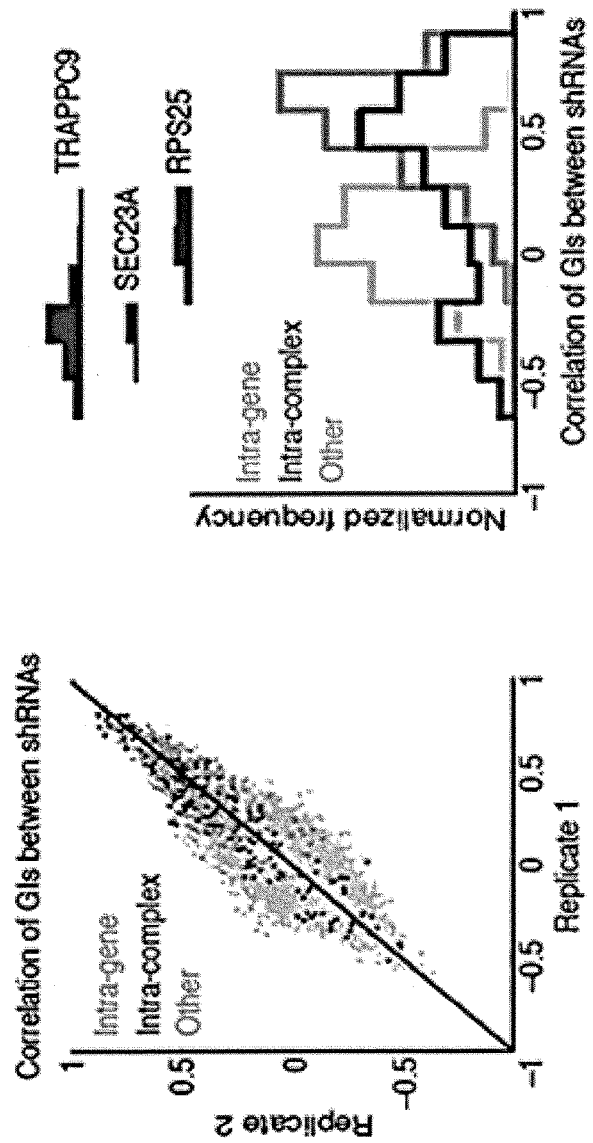
FIGS. 20A-C show that a GI map reveals functionally and physically interacting genes. (A,B) Correlations of GI patterns between shRNA pairs: shRNAs targeting the same gene, shRNAs targeting different genes in previously known physical complexes, other pairs of shRNAs. (A) Reproducibility of GI correlations between shRNA pairs in two experimental replicates. (B) High inter-gene and inter-complex correlation of GIs. Distribution of correlation coefficients between shRNA pairs are shown for the three classes of shRNA pairs. The anti-correlated part of the bimodal distribution of intra-complex shRNA pairs is fully accounted for by pairs including shRNAs targeting TRAPPC9, SEC23A, and RPS25. (C) GIs for all gene pairs were calculated (shown as a heatmap) and genes were clustered hierarchically based on the correlation of their GIs. Individual phenotypes are indicated by sidebars using a heatmap. Genes marked with asterisks were imported from a separate double-shRNA screen conducted with a partially overlapping gene set. Known physically or functionally interacting groups of genes are labeled by vertical lines; diamonds mark interactions defined in this study.
Figure 21:
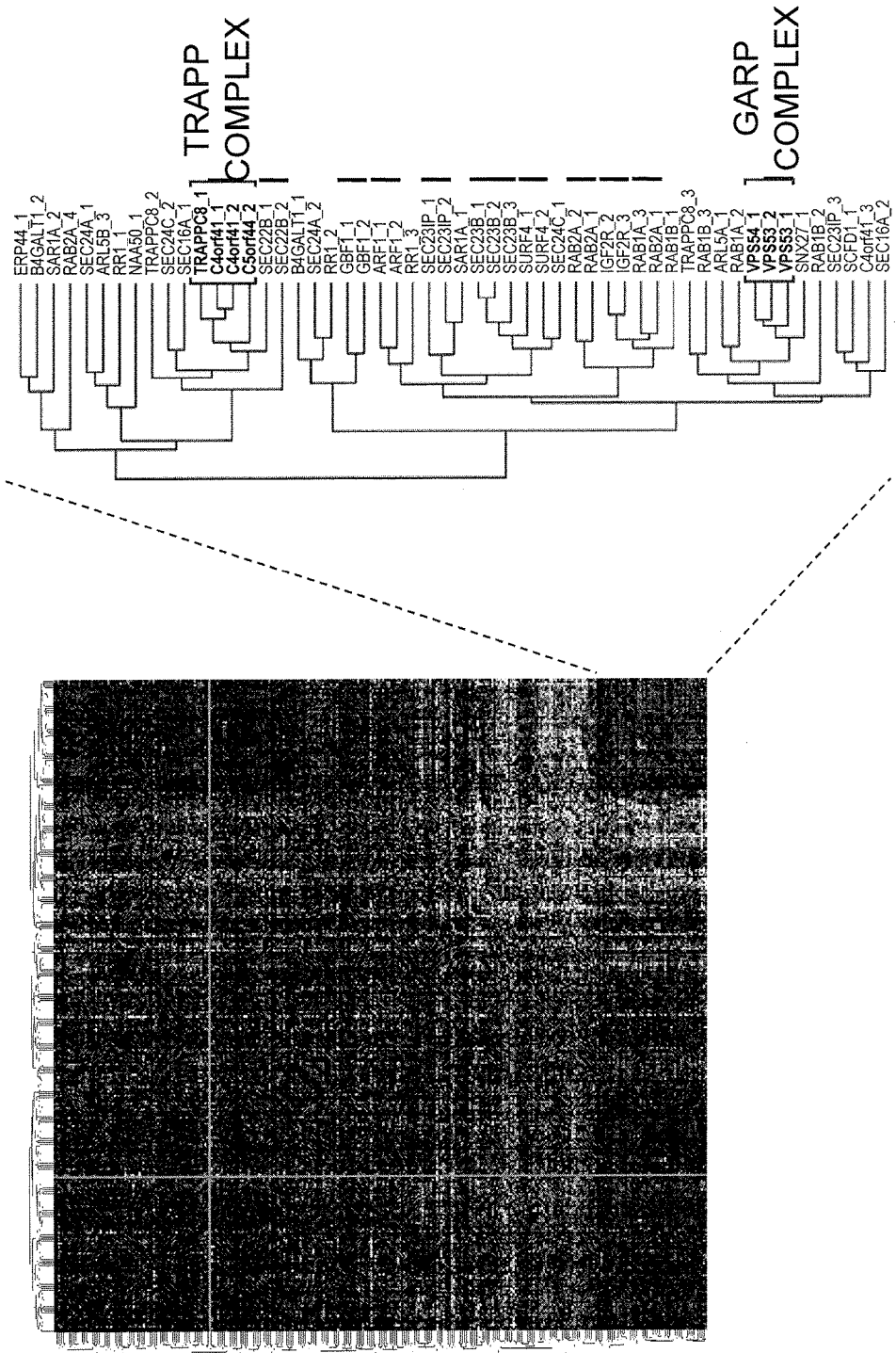
FIG. 21 illustrates an exemplary mammalian epistasis map (EMAP) generated using the methods of the present invention.

Correlations between shRNA GI patterns derived from double-shRNA screens were highly reproducible between independent experimental replicates (FIG. 20A). As expected, shRNAs targeting the same gene had more correlated GI patterns than other shRNAs (FIG. 20B), indicating that their phenotypes were mostly due to on-target knockdown. Similarly, shRNA pairs targeting different members of the same protein complex had highly correlated GI patterns, which were clearly distinct from the bulk of shRNA pairs. This result demonstrates the ability of the present approach to broadly identify genes encoding members of the same physical complex. Interestingly, shRNAs targeting a small set of genes produced GI patterns that were anti-correlated with those targeting other components of the same physical complex (FIG. 20B), causing an overall bimodal distribution of intra-complex GIs. These genes also had the opposite phenotype in the primary screen: TRAPPC9 (anti-correlated with other members of the TRAPP complex), SEC23A (anti-correlated with other COPII components) and RPS25 (uncorrelated with ribosomal proteins of the large subunit). The unusual behavior of these three genes is robustly observed for all three shRNAs targeting each of them, and therefore likely to reflect the functional differences. These findings illustrate that these genetic results can functionally dissect known physical complexes, which are explored below in more detail for RPS25 and the TRAPP complex.

A possible source of noise in an RNAi-based GI map is the fact that an effective on-target shRNA can have partial off-target effects, which can confound its GI pattern. To minimize this effect, each gene in the GI map was required to be targeted by at least two (and typically three) shRNAs whose GI patterns were sufficiently correlated (Kampmann et al, MS in review), and averaged the GIs of these highly correlated shRNAs for each gene. Using these stringent criteria, the resulting GI map (FIG. 20C) encompassed pairwise interactions between 60 genes, each represented by 3 shRNAs on average, and was based on the pooled measurement of >36,000 double-shRNA phenotypes. The main limitation for increasing the scale of GI maps is the availability of highly validated shRNAs, as a single bioreactor run can measure >500,000 shRNA pairs.

Functional Predictions from the Ricin GI Map

Figure 20C:
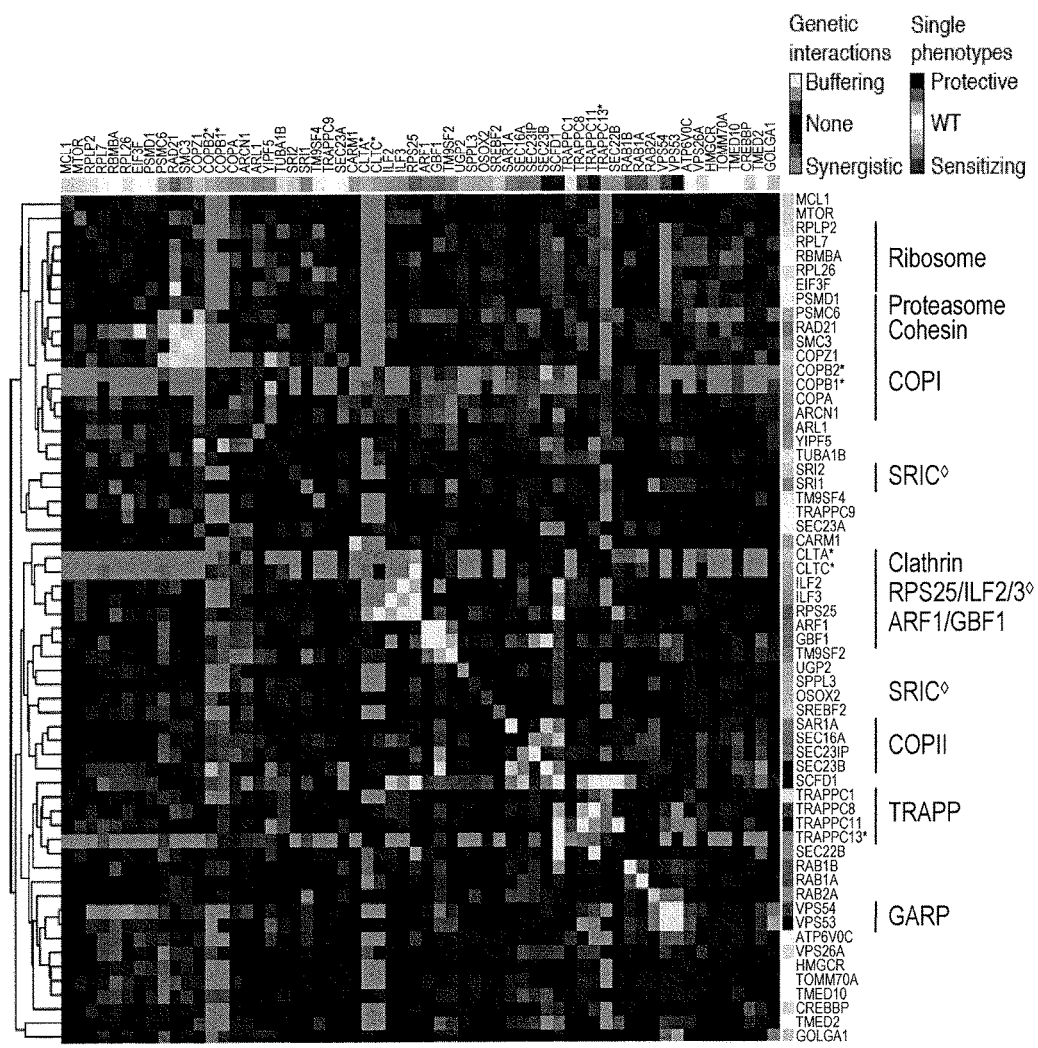

Hierarchical clustering of genes based on the correlation of their GIs was remarkably successful at recapitulating a number of well-characterized complexes, including the COPI and COPII vesicle coats, clathrin, GARP and the ribosome, as well as complexes with unknown roles in ricin biology, such as the cohesins (FIG. 20C). In addition, the map demonstrated clustering of functionally interacting proteins, such as the small GTPase ARF1 and its guanine nucleotide exchange factor GBF1.

The GI maps also lead to numerous novel functional predictions, three of which are highlighted below.

An Unexpected Role for Ribosomal Protein RPS25.

Figure 34A:
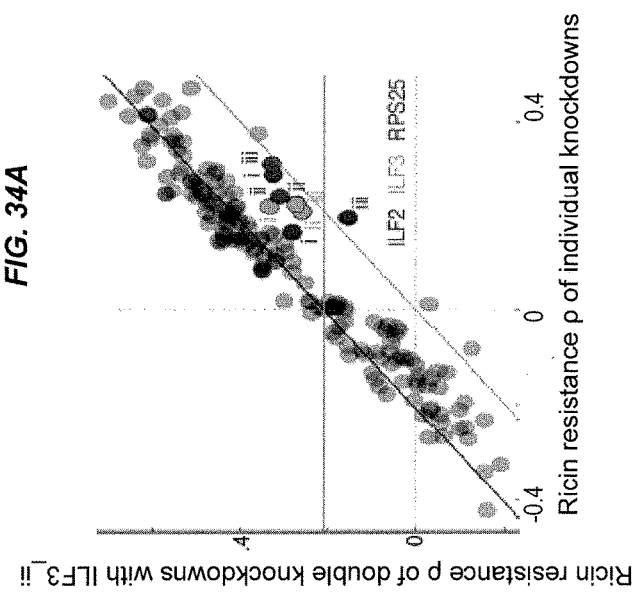
Figure 34B:
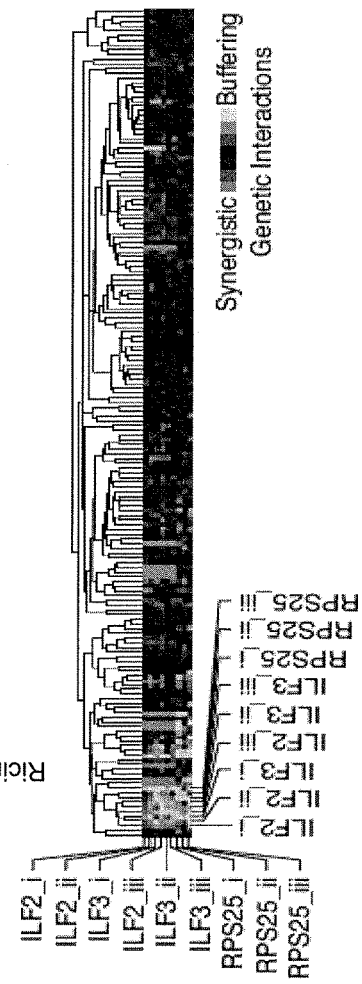

Remarkably, this study found that RPS25 knockdown conferred ricin resistance. By contrast, all other ribosomal hits sensitized cells to ricin, as expected, since ribosome inactivation is the basis for ricin cytotoxicity. The GI map provided a clue to the divergent role of RPS25: RPS25 formed a cluster with ILF2 and ILF3 (FIG. 20C). ILF2 and ILF3 encode the two subunits of NFAT, a transcription factor (Wu et al., 2007). NFAT knockdown protected against ricin, and this study confirmed that the shRNAs against RPS25 and NFAT acted through their intended target genes. As expected for proteins in a physical complex, shRNAs targeting ILF2 showed buffering GIs with shRNAs targeting ILF3 (FIG. 34A, B). Surprisingly, very strong buffering interactions between NFAT and RPS25 was also observed, which was consistent for all combinations of the 9 shRNAs targeting ILF2, ILF3, and RPS25 (FIG. 34B).

Previous literature has implicated both RPS25 and NFAT in translational control: RPS25 has been shown to be required for translation of IRES-containing mRNAs in cricket paralysis virus (Landry et al., 2009), while NFAT can bind viral IRES and control translation (Merrill and Gromeier, 2006). Therefore, NFAT/RPS25 may work together to control translation of certain transcripts that affect ricin sensitivity, possibly under particular stress conditions.

Identification of the SRI (Sensitization to Ricin) Complex.

One unexpected prediction was the interaction between WDR11 and C17orf75, two poorly characterized genes. Both sensitized cells to ricin when depleted, exhibited highly correlated profiles in the GI map, and showed buffering interactions with each other, which is often a signature for genes encoding proteins in the same pathway or physical complex. This study found indeed that the encoded proteins interacted in reciprocal immunoprecipitation experiments (FIG. 34C-D). Since the proteins appear to form a complex and sensitize cells to ricin when depleted, it is proposed that they be named SRI1 and SRI2 (Sensitization to RIcin), for WDR11 and C17orf75, respectively.

Previously SRI1 (WDR11) was suggested to interact with a transcription factor (Kim et al., 2010), as well as to impact flux through the autophagy pathway (Behrends et al., 2010). Consistent with the latter observation, this study found that GFP-tagged SRI1 partially colocalized with the autophagosome marker LC3 (FIG. 34E). This suggests a potential role for SRI in toxin degradation. Indeed, depletion of SRI1 or BECN1, a regulator of autophagy, caused an increase in total cellular ricin (FIG. 34F). By contrast, other genes that sensitized (COPZ1) or protected (TRAPPC8) cells against ricin had an insignificant effect on total toxin levels (although they do affect toxin delivery to the ER, FIG. 34G). When degradation pathways are inhibited, more ricin can enter the productive intoxication pathway (FIG. 34H), which provides a potential explanation for the observed increase in delivery of toxin to the ER upon depletion of SRI1 (FIG. 34G).

Functional Dissection of the Mammalian TRAPP Complex.

Figures 35A, 35B, 35C:
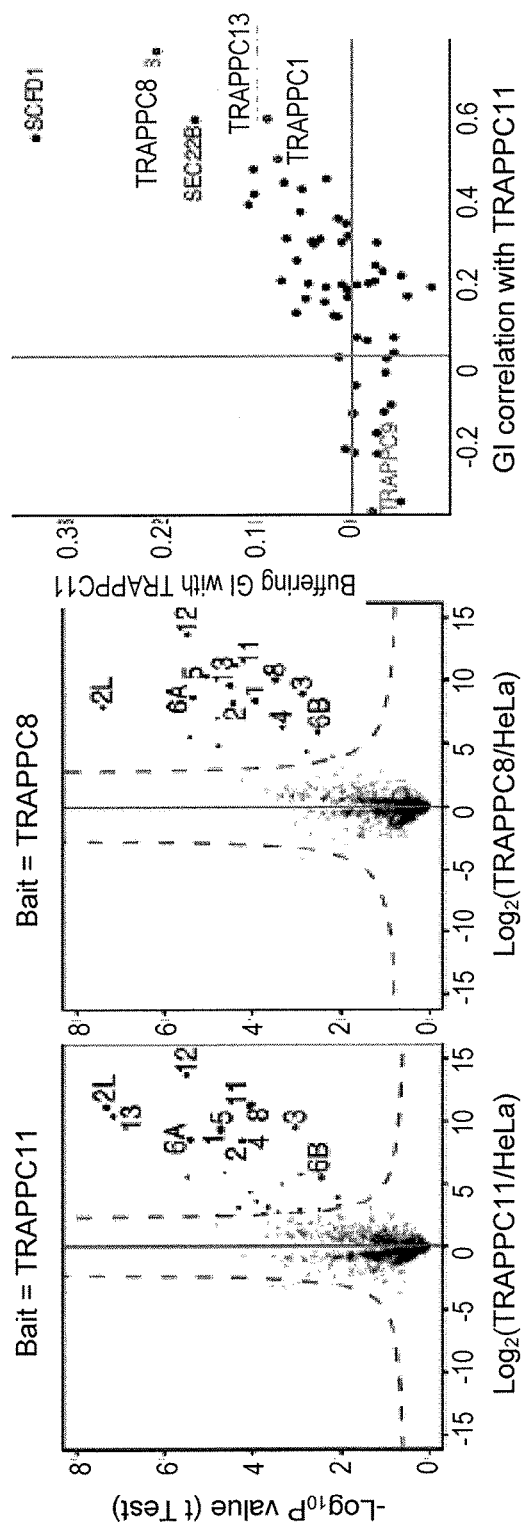

Two of the most strongly protective hits from the primary screen, C4orf41 and KIAA1012, were poorly characterized at the onset of our studies. In the GI map, these genes formed a highly correlated cluster connected by buffering GIs with another poorly characterized gene, C5orf44, and with TRAPPC1, a member of the TRAPP complex, a highly conserved multi-subunit complex involved in ER-Golgi, endosome-Golgi, and autophagosome transport (Barrowman et al., 2010). Based on this pattern, C4orf41, KIAA1012 and C5orf44 were predicted function as TRAPP complex components. To test this, these components were GFP-tagged and immunoprecipitated (FIG. 35A-B). This study could identify most TRAPP components described to date in both immunoprecipitations, as well as C5orf44. C4orf41 and KIAA1012 were previously identified as TRAPP3 interactors in a high-throughput immunoprecipitation study (Gavin et al., 2002), and concurrent with these studies, were independently identified as TRAPP components and designated TRAPPC8 and TRAPPC11, respectively (Scrivens et al., 2011). Additionally, C5orf44 was recently shown to exhibit homology to yeast Trs65 and physically interact with other TRAPP components (Choi et al., 2011). Based on these observations, C5orf44 was designated as TRAPPC13.

In yeast, several TRAPP complexes have been identified (Barrowman et al., 2010) with distinct roles in ER-Golgi traffic (TRAPPI), intra-Golgi and endosome-Golgi traffic (TRAPPII), and autophagy (TRAPPIII). In mammalian cells, TRAPP has been suggested to form a single large complex (Scrivens et al., 2011), and it has been unclear whether this complex is responsible for all observed TRAPP activities.

Figure 35D:
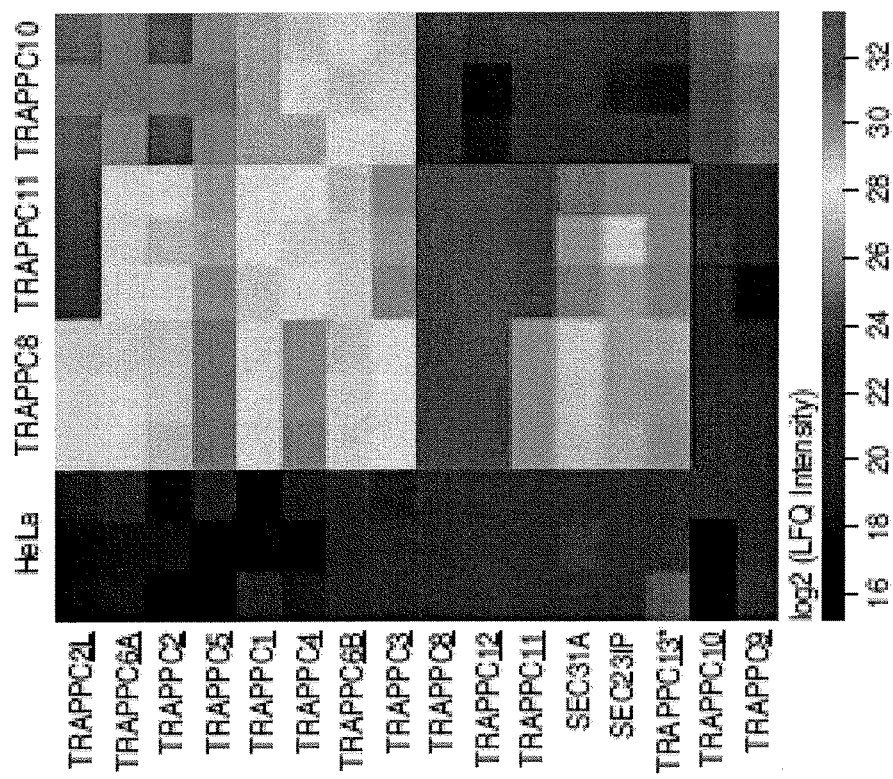

The present data revealed a clear functional distinction between different TRAPP components. This study found only a subset of TRAPP components as strongly protective hits, while other components had either no phenotype or, in the case of TRAPPC9, were mildly sensitizing. Moreover, the genetic interaction pattern of TRAPPC9 showed a striking anti-correlation with TRAPPC11 (FIG. 35C), indicating that complexes containing these proteins are distinct, and have opposing roles in ricin trafficking. Indeed, it was found that immunoprecipitation of either TRAPPC8 or TRAPPC11 pulled down the COPII components SEC31A and SEC23IP as well as the other known TRAPP components, with the prominent exception of TRAPPC9 and TRAPPC10 (FIG. 35D). Similarly, previous immunoprecipitation experiments found that TRAPPC9 did not recover TRAPPC8 (Zong et al., 2011). Conversely, this study found that immunoprecipitation of TRAPPC10 pulled down core TRAPP components, but not TRAPPC8/11/12/13, SEC31 or SEC23IP (FIG. 35D). Based on this, the migration properties of the various TRAPP components were examined by size exclusion chromatography. These studies directly established the existence of two physically distinct complexes: a larger complex containing TRAPPC8 and TRAPPC11 and a smaller one containing TRAPPC10 (FIG. 35E).

To further define mammalian TRAPP complexes, their interactions were examined with COPII components. The yeast TRAPPI complex is a COPII vesicle tethering factor (Sacher et al., 2001), and COPII and TRAPPC3 interact in yeast and mammalian cells (Cai et al., 2007). Consistent with this, GFP-labeled TRAPPC8 and TRAPPC11 colocalized with SEC31A. The finding that TRAPPC8 and TRAPPC11, but not TRAPPC10, coimmunoprecipitated the COPII component SEC31A (FIG. 35F), indicates that differential interaction with COPII may functionally distinguish the two mammalian TRAPP complexes. Indeed, knockdown of TRAPC11 or TRAPC12 but not TRAPPC9 disrupted the interaction of TRAPPC8 with SEC31A (FIG. 35F). Thus the two distinct mammalian TRAPP complexes, defined by the presence of TRAPPC9/10 or TRAPPC8/11/12/13, differentially interact with COPII (FIG. 35H).

The two TRAPP complexes seem to have opposing roles in ricin transport. Since protection against ricin was observed with COPII or TRAPP8/11/12/13 knockdowns, and these components interact physically, this complex may function similarly to yeast TRAPPI in COPII vesicle tethering. Additionally, TRAPPC8 knockdown has been reported to impact flux through the autophagy pathway (Behrends et al., 2010), and a mild enhancement of toxin degradation was observed upon TRAPPC8 knockdown (FIG. 34H), raising the possibility that the TRAPPC8/11/12/13 complex functions in both COPII-mediated trafficking and autophagy. By contrast, TRAPPC9/10 was previously reported to interact with COPI components (Yamasaki et al., 2009). Moreover, this study found that both COPI and TRAPPC9 knockdown sensitize cells to ricin, indicating that the TRAPPC9/10 containing complex may function in tethering of COPI vesicles. More generally, these findings establish that there are functionally distinct mammalian TRAPP complexes and lay the groundwork for a mechanistic understanding of their specialized functions.

Perspective

Building on previous pooled shRNA strategies (e.g., Moffat et al., 2006; Silva et al., 2005), an integrated platform has been developed to functionally dissect complex biological processes in mammalian cells using high-density genetic interaction maps. This strategy opens mammalian cell biology to the types of systematic genetic analyses that have been highly successful in microorganisms (Collins et al., 2009; Dixon et al., 2009).

The first application of the platform elucidated key cellular pathways and revealed how they modulate ricin susceptibility. The studies of the TRAPP complex, in particular, illustrate how genetic and physical interactions provide complementary approaches to understand the functions of multiprotein complexes as these studies revealed two functionally distinct mammalian TRAPP complexes.

A key aspect of the primary screening platform of the invention is the ability to identify hit genes based on the likelihood that shRNAs act through the intended target gene rather than solely the strength and reproducibility of observed shRNA phenotypes. This is facilitated by the use of ultra-complex shRNA libraries that include a large number of negative controls. This approach also provides a principled way to benchmark shRNA library design and screening systems based not only on the strength of on-target mRNA knockdown, but also by the ability to distinguish true hits from background (e.g., off-target effects or statistical noise). Another important feature of ultra-complex libraries is that they target each gene with a wide spectrum of shRNAs with different knockdown strengths, effectively creating an allelic series. This will facilitate the study of essential genes, as well as gene dosage effects. While the genetic interaction maps are currently based on shRNAs identified in a primary screen, a growing library of validated shRNAs enables mapping of interactions between genes that do not have an individual phenotype, and the detection of synergistic genetic interactions between them. Ongoing efforts by several groups to identify effective shRNAs (Cheung et al., 2011; Fellmann et al., 2011; Marcotte et al., 2012) will greatly facilitate the construction of larger GI maps.

This approach is broadly applicable to the study of complex biological systems. While a pooled screening strategy based on cell growth and viability is presented herein, other phenotypic readouts that physically separate cell populations can be used, such as fluorescence-activated cell sorting or migration assays. In addition, the ability to rapidly generate and screen a double-shRNA library allows one to explore conservation and rewiring of genetic interactions in diverse cell types and under different conditions (Bandyopadhyay et al., 2010).

The systematic exploration of genetic interactions in human cells also has broad medical relevance, especially for cancer biology and therapy. Functional surveys of genes in cancer cells can distinguish oncogenic drivers from mere passengers. Genetic interactions are thought to be crucial determinants of properties of individual cancer cells (Ashworth et al., 2011), such as their resistance to therapeutic agents. A better understanding of resistance pathways in specific genetic backgrounds could pave the way for personalized combination therapies that preemptively block the cancer's escape routes. More generally, as demonstrated for HIV, combination therapy is a promising strategy to counter the problem of rapidly evolving drug resistance in tumors. The ability to identify rare synthetic lethal interactions between huge numbers of gene pairs maximizes the opportunity to identify pairs of drugs that synergistically target a disease state.

Experimental Procedures shRNA Libraries.

To express shRNAs from a PolII promoter in a miR30-derived context, strategies developed by the Hannon and Elledge groups (Paddison et al., 2004; Silva et al., 2005) were adapted. Construction of pooled libraries was conducted essentially as previously described (Bassik et al., 2009). The genome-wide library was divided into 9 sublibraries with 55,000 shRNA each and targeted each human protein-coding gene with ~25 independent shRNAs. Each sublibrary also contained 500 or more negative control shRNAs, which were designed to match the base composition of targeted shRNAs within the same sublibrary, without targeting any transcript in the human genome.

Ricin Resistance Screening.

For pooled screens, cells were seeded at $0.5 \times 10^6$/ml at a representation of 1000 cells/library element, and treated with 0.5 ng/ml ricin (Vector labs), which reduced cell number by ~50% compared with untreated cells, due to a combination of cell death and reduced growth rate. This selective pressure represents a compromise between stronger selection, which can increase the dynamic range of observed phenotypes, and weaker selection, which reduces population bottlenecks and thus reduces Poisson sampling noise. After 24 h, ricin was washed out. Each day during the screen, cells were diluted to to $0.5 \times 10^6$/ml. After 2-3 days of recovery when treated cells were again doubling at WT rate, a new cycle of ricin treatment was initiated (total of 4 pulses). For competitive growth assays, cells were infected with lentivirus encoding individual shRNAs. After 3 days, cells were seeded in 24-well plates at $0.5 \times 10^6$/ml and treated with 0.5 ng/ml ricin. After 24 h, ricin was washed out, and cells were adjusted to $0.5 \times 10^6$/ml. Percentages of mCherry-positive cells were assessed by FACS 24-48 h later.

Pooled shRNA Libraries for Primary Screens.

shRNAs against all protein-targeting transcripts in human cells were designed using the shRNA retriever program (Paddison et al., 2004), which generates shRNAs with 22-nucleotide guide strands, and the si-shRNA Selector program (Matveeva et al., 2010), which generates shRNAs with 21-nucleotide guide strands. Any shRNAs whose target sites were less than 3 substitutions away from a site in a human transcript derived from a gene other than the intended target gene were excluded. To generate matched negative control shRNAs, the base frequency at each guide strand position for the set of 21-mer and 22-mer shRNAs in each sublibrary was determined, and sets of random shRNAs with the same base frequencies were generated. From these sets, any shRNAs whose target sites were less than 3 substitutions away from any site in a human transcript were excluded. Oligonucleotides encoding shRNAs in a sublibrary of 55,000 sequences were synthesized by Agilent, and used to generate shRNA libraries essentially as previously described (Bassik et al., 2009). 9 sublibraries were generated where genes were organized into functionally related groups, using GO annotation, curated localization, and data from various proteomic surveys of organelles. shRNAs were cloned into our vector pMK1047, for which a detailed map will be provided on request. This vector was derived from pMCB-BSTX-DSH, which is a modification of the lentiviral pSicoR vector (Jacks lab, MIT) in which: 1) the U6 promoter and downstream MCS were removed, 2) an EF1A promoter was used to drive expression of an mRNA encoding a puromycin resistance marker, the ribosomal skipping peptide T2A, mCherry, and the shRNA, 3) an shRNA cassette was inserted in a modified minimal mir30 context in which BstXI sites allow cloning of shRNAs (described below) (mir30 modified from (Silva et al., 2005), and 4) restriction sites allow subsequent shRNA concatenation (described in detail below).

Construction of Individually Barcoded shRNA Vectors.

The barcoding vector pMK1098, a lentiviral expression vector containing two random 10-basepair barcodes flanking a miR30-context sequence, was prepared as follows. A short PCR product was generated using pMK1047 as a template with primers oMK194 and oMK195, which each contain a randomized 10-mer random barcode. The resulting insert was digested with MfeI and XbaI and ligated into the pSicoR-derivative pMK1040 (digested with EcoRI+XbaI) to obtain the barcoding vector pMK1098. Pairs of oligonucleotides encoding shRNA were annealed and ligated into the pMK1098 backbone, which was cut with BstXI and gel-purified. The mir30-based format for the oligos was as follows for an example target site TTTCTTACTCACCCTAAGAACT:

Top Oligonucleotide:

CGTTCTTAGGGTGAGTAAGAAATAGTGAAGCCACAGATGTATTTCTTACT

CACCCTAAGAACTTGCC

Bottom Oligonucleotide:

AGTTCTTAGGGTGAGTAAGAAATACATCTGTGGCTTCACTATTTCTTACT

CACCCTAAGAACGCGCT

Resulting plasmids were sequenced using 5' pSico-Eco-insert-seq or 3' pSico-Pci-insert-seq to ascertain accuracy of the clone and to determine the pairing between barcodes and shRNAs. A clone was accepted if the insert and backbone sequences were correct, the barcodes were at least 2 substitutions away from all other previously accepted barcodes in our library, the downstream barcode did not end in GA (since this creates a dam methylation site that interferes with XbaI cleavage) and the barcodes did not create additional cleavage sites for the enzymes PvuII, AvrI, XbaI or KpnI, which are used in subsequent steps.

Construction of Double-shRNA Libraries.

The plasmids to be included in the double-shRNA interaction map were pooled—either at stoichiometric amounts, or in ratios that partially compensate for the expected phenotypes. In the pMK1098-derived plasmids, the barcoded miR30-shRNA cassette was flanked by sites for cleavage by a pair of restriction enzymes, AvrII and XbaI, that create compatible ends. This enabled the digest of a pool of shRNA-encoding plasmids with KpnI in combination with either AvrII or XbaI in two separate reactions, and the ligation of products from the two reactions to create all pairwise combinations of double-shRNA vectors, in which two shRNAs are expressed within the same PolII-driven transcript within short miR30 contexts. At the junction between the two, a combinatorial barcode is created that can be monitored by deep sequencing and uniquely identifies the double shRNA (FIG. 33). The ligation mixture was transformed into bacteria to prepare a pooled library for lentiviral infection, as for primary screens (Bassik et al., 2009).

Computational Data Analysis.

For primary screens, the sequences of the guide strands of the shRNA-encoding constructs were detected by deep sequencing and aligned to the known library sequences using Bowtie (Langmead et al., 2009); only perfect matches to a guide strand sequence from our library were counted. For batch retest d double-shRNA screens, the frequency of shRNAs and double-shRNAs, respectively, was determined by deep sequencing of the associated barcodes. From the deep sequencing data, the phenotypic metric $\rho_X$ for the ricin resistance conferred by an shRNA X was calculated as:

$$\rho_X = \frac{1}{kt}\log_2 \frac{N_X^R/N_{WT}^R}{N_X^U/N_{WT}^U}$$

where kt is the difference in cell doublings between the untreated WT cells and the ricin-treated WT cells during the screen, $N_X$ denotes the frequency of shRNA X and $N_{WT}$ denotes the median frequency of negative control shRNAs in untreated (U) or ricin-treated (R) populations. The genome-wide screen was carried out in two independent replicates and shRNA phenotypes from the replicates were averaged before calculating a P value for each gene.

To identify hit genes in the genome-wide primary screen, the concept of taking into account the full spectrum of shRNA phenotypes targeting a gene, first explored by the RIGER algorithm (Luo et al., 2008), was further developed. The statistical significance for each gene was quantified by comparing the set of ρs for shRNAs targeting it with the set of ρs for negative control shRNAs using the Mann-Whitney U test, which performed most robustly for the dataset. Testing against a large set of negative controls, as opposed to the entire set of targeted shRNAs increased the sensitivity of hit detection. To correct for multiple hypothesis testing, the false discovery rate (FDR) was calculated based on the genome-wide distribution of P values (Storey and Tibshirani, 2003). Sets of top protective and sensitizing hits were defined based on FDR cutoffs.

The set of hit genes was tested for enrichment of GO terms using DAVID (Huang da et al., 2009a, b). In FIG. 18B, GO terms up to an FDR of 5% are displayed. In cases where different GO-terms encompassing the same subset of hit genes were found, only one is displayed. Similarly, in cases where a GO term described a subset of hit genes of those described by another GO term that had a more significant P value, only the more significant GO term describing a larger set of hit genes is displayed.

For the double-shRNA screen, a library was constructed expressing all pairwise combinations of 184 targeted shRNAs and 12 negative control shRNAs. Combinations of negative control shRNA served as negative control distribution, combinations of a negative control and a targeted shRNA were used to calculate single-shRNA phenotypes, and combinations of two targeted shRNAs yielded double-mutant phenotypes. GIs were quantified as deviation of double-mutant phenotypes from the expected phenotypes, which are defined as the linear fit of combinations involving a given "bait" shRNAs with all other shRNAs versus the single phenotypes of the other shRNAs. GIs were averaged between independent experimental replicates and Pearson correlations between GI profiles of individual shRNAs were calculated. If shRNAs targeting the same gene did not have a correlation with other shRNAs targeting the same gene that was at least 0.8 standard deviations above the mean correlation, they were excluded from further analysis. After this filtering step, GIs for shRNAs targeting the same gene were averaged. For display purposes, GIs for gene pairs with a double-mutant phenotype closer to WT than expected were defined as buffering GIs and gene pairs with a double-mutant phenotype further from WT than expected were defined as synergistic.

To construct GI maps, GIs between shRNA pairs were calculated for two experimental replicates separately. Then GIs for shRNA pairs in the two possible orientations were averaged and the experimental replicates were averaged. After filtering out uncorrelated shRNAs for each gene, GI patterns for shRNAs targeting the same gene were averaged. For the GI map presented in FIG. 20C, data for five genes not present in the final double-shRNA library were imported from an earlier experiment that used a partially overlapping double-shRNA library. Genes were hierarchically clustered based on the uncentered Pearson correlations of their GI profile and displayed using Java TreeView software (Eisen et al., 1998).

Cell Culture and Lentiviral Infection.

K562 and Raji B cells were grown in RPMI medium supplemented with glutamine, penicillin/streptomycin, and 10% FBS. HeLa cells and 293T cells were grown in DMEM medium with high glucose, further supplemented with glutamine, penicillin/streptomycin, and 10% FBS. For individual gene infections, virus was produced in 6-well plates, and 1 ml viral supernatant adjusted to 8 μg/ml polybrene was used to infect 100,000 cells by spin infection at 1,000×g for 2 h at 33° C. For library infections, virus was produced in 15-cm plates of 293T cells. Library infections were performed on 35×10⁶ cells in 70 ml virus supernatant with 8 μg/ml polybrene, divided into wells of a 6-well plate, and spin-infected as above to get a target infect ion of ~30-40%. 3 days after infection, cells were selected with puromycin at 0.7 μg/ml for 3 days, and then washed into fresh medium and allowed to recover for 2 days.

Sample Preparation for Deep Sequencing.

Following each screen, 100×10⁶ cells were lysed and genomic DNA was purified using 1 column of a Qiagen Blood Maxi kit. 500 μg–1 mg of genomic DNA was digested for 16 h with PvuII (NEB). Then the entire genomic digest was loaded onto a 0.8% agarose gel using custom gel combs in an Owl A1 gel rig, and run at 220V for 1.5 h. Genomic DNA in the expected size range (1.2 kb) was excised, and gel-purified. The eluted DNA was used as a template for PCR, where 1.5 μg genomic DNA was used per 100 μl PCR reaction (usually 20-25 reactions), using Phusion polymerase (NEB) and buffer HF. The following primer pairs were used for PCR: For primary screens: oMCB800 in combination with oMK196, oMK197, oMK205, oMK206, oMK254, oMK255, oMK256 or oMK257 (which contain distinct 4-nucleotide indices to allow sample identification after multiplexed deep sequencing); for batch retest experiments: oMCB922 in combination with oMK198, oMK199, oMK200, oMK201, oMK258, oMK259, oMK260 or oMK261 (which again contain different 4-nucleotide indices); for double-shRNA libraries: oMCB847 in combination with oMK198, oMK199, oMK200, oMK201, oMK258, oMK259, oMK260 or oMK261. PCR products were purified on Qiagen gel extraction columns using buffer PB, and then run on 20% polyacrylamide gels in 0.5×TBE. Bands of the correct size were excised, electroeluted, purified on a gel extraction column, and then quantitated using an Agilent bioanalyzer. Deep sequencing was carried out on an Illumina HiSeq 2000, using the following sequencing primers: for primary screens, oMK132; for batch retests and double-shRNA screens, Illumina genomic sequencing primer.

Antibodies.

Antibodies were obtained against SNAP (NEB), SEC31A (BD Transduction labs), TRAPPC00 and ricin (Santa Cruz), TRAPPC8 and TRAPPC11 (Sigma), and TRAPPC3 (Protein Tech), and were used accord in g to manufacturer's specifications.

Microscopy. HeLa-Kyoto cells expressing GFP-tagged genes of interest were generated as previously described (Poser et al., 2008). These cells were maintained in 400 μg/ml G418. Constructs expressing full length human MAP1LC3B or LAMP1 were fused to mCherry in a lentiviral construct. HeLa cells were infected with these and selected with 1 μg/ml puromycin. Cells were plated in a 24-well glassbottom plate (MatTek). Hoechst stain was added to growth medium just before cells were examined with a Nikon Ti-E spinning disk microscope at 63× or 100× magnification. For immunofluorescence, cells were fixed with 4% paraformaldehyde in PBS for 10 min, washed in PBS, permeabilized/blocked in 0.1% Triton/PBS/5% normal goat serum (NGS Block) for 30 min, and then probed with the indicated antibodies in NGS Block. Cells were then washed in 0.1% Triton/PBS 3×10 min, re-probed with secondary antibody 30 min in NGS Block, washed again as above, and then mounted in VectaShield (Vector Labs).

Immunoprecipitation, Mass Spectrometry, and Fractionation.

Immunoprecipitation and mass spectrometry was performed essentially as previously described (Frost et al., 2012). GFP-tagged TRAPP constructs were expressed in HeLa cells, or FLAG-tagged WDR11 and C17orf75 constructs were expressed in K562 cells. 75×10⁶ cells were collected and washed with PBS, and then lysed in 3 ml digitonin lysis buffer (50 mM HEPES, pH 6.8, 150 mM potassium acetate, 2 mM Mg-acetate, 1 mM $CaCl_2$, 15% glycerol, 1.5% digitonin, and protease inhibitor cocktail, EDTA-free, Roche) by nutating for 45 min at 4° C. Lysates were clarified at 82,000×g for 20 min in a Ti50.2 rotor. Lysates were immunoprecipitated using anti-GFP beads (Chromotek) or anti-flag beads (Sigma) for 1 h, and then lysates were washed 3× with 12 ml wash buffer (lysis buffer with 0.1% digitonin). Bound proteins were then digested on the beads with trypsin and prepared for mass spectrometry. Alternatively, proteins were boiled on beads in 1× NuPage sample buffer and loaded on an 8-12% acrylamide gel before western blotting with the indicated antibodies.

For fractionation of extracts, 200 million K562 or HeLa cells were collected, washed in PBS, and lysed in 2.5 mL 1.5% digitonin buffer (as above). 100 uL of cleared lysate was loaded on a 24 mL Superose 6 column (Amersham), and 0.5 mL fractions were collected in 0.1% digitonin wash buffer (as above). Every other fraction was TCA precipitated, washed, and ½ was loaded on a gel for western blotting.

qPCR.

For qPCR, 1-2×10⁶ cells were collected and RNA was purified using an RNeasy kit (Qiagen). 1-2 μg total RNA was used for reverse transcription using AMV RT (Roche) and oligo dT. Samples were then quantitated by qPCR using Go-Taq polymerase (Promega) and SYBR green using a LightCycler 480 (Roche).

SNAP Transport Assay.

ER-targeted SNAP was a kind gift of Ari Helenius, and stable K562 cell lines were generated that express this construct under G418 selection (750 μg/ml). NHS-BG (NEB) was conjugated to ricin (Vector labs) as described (Geiger et al., 2011), and washed into PBS. For transport assays, 1.5 ml of cells at 0.75×10⁶/ml were plated in a 24-well plate, and 17.5 µg of purified BG-NHS-ricin was added in 35 µl. After 8 h, cells were washed in PBS and lysed in RIPA buffer. Lysates were run on 4-12% PAGE and western blots were performed using anti-myc 9E10 (Covance) or anti-snap (NEB) antibodies.

Total Cellular Ricin Measurements.

To measure total cellular ricin, $1.1 \times 10^6$ cells were plated in 1.5 ml RPMI medium, and 5 µg ricin was added. After 1.5 h, cells were washed and replated in 1.5 ml RPMI medium. After a 16 h incubation, cells were washed in PBS and lysed in 30 µl RIPA buffer. Lysates were run on 4-12% PAGE and western blots were performed u sing anti-ricin A chain antibody (Santa Cruz).

REFERENCES

Amessou, M., Fradagrada, A., Falguieres, T., Lord, J. M., Smith, D. C., Roberts, L. M., Lamaze, C., and Johannes, L. (2007). Syntaxin 16 and syntaxin 5 are required for efficient retrograde transport of several exogenous and endogenous cargo proteins. J Cell Sci 120, 1457-1468.

Ashworth, A., Lord, C. J., and Reis-Filho, J. S. (2011). Genetic interactions in cancer progression and treatment. Cell 145, 30-38.

Bandyopadhyay, S., Mehta, M., Kuo, D., Sung, M. K., Chuang, R., Jaehnig, E. J., Bodenmiller, B., Licon, K., Copeland, W., Shales, M., et al. (2010). Rewiring of genetic networks in response to DNA damage. Science 330, 1385-1389.

Barbie, D. A., Tamayo, P., Boehm, J. S., Kim, S. Y., Moody, S. E., Dunn, I. F., Schinzel, A. C., Sandy, P., Meylan, E., Scholl, C., et al. (2009). Systematic RNA interference reveals that oncogenic KRAS-driven cancers require TBK1. Nature 462, 108-112.

Barrowman, J., Bhandari, D., Reinisch, K., and Ferro-Novick, S. (2010). TRAPP complexes in membrane traffic: convergence through a common Rab. Nat Rev Mol Cell Biol 11, 759-763.

Bassik, M. C., Lebbink, R. J., Churchman, L. S., Ingolia, N. T., Patena, W., LeProust, E. M., Schuldiner, M., Weissman, J. S., and McManus, M. T. (2009). Rapid creation and quantitative monitoring of high coverage shRNA libraries. Nat Methods 6, 443-445.

Behrends, C., Sowa, M. E., Gygi, S. P., and Harper, J. W. (2010). Network organization of the human autophagy system. Nature 466, 68-76.

Bonifacino, J. S., and Hierro, A. (2011). Transport according to GARP: receiving retrograde cargo at the trans-Golgi network. Trends Cell Biol 21, 159-167.

Butland, G., Babu, M., Diaz-Mejia, J. J., Bohdana, F., Phanse, S., Gold, B., Yang, W., Li, J., Gagarinova, A. G., Pogoutse, O., et al. (2008). eSGA: E. coli synthetic genetic array analysis. Nat Methods 5, 789-795.

Cai, H., Yu, S., Menon, S., Cai, Y., Lazarova, D., Fu, C., Reinisch, K., Hay, J. C., and Ferro-Novick, S. (2007). TRAPPI tethers COPII vesicles by binding the coat subunit Sec23. Nature 445, 941-944.

Carette, J. E., Guimaraes, C. P., Varadarajan, M., Park, A. S., Wuethrich, I., Godarova, A., Kotecki, M., Cochran, B. H., Spooner, E., Ploegh, H. L., et al. (2009). Haploid genetic screens in human cells identify host factors used by pathogens. Science 326, 1231-1235.

Carette, J. E., Guimaraes, C. P., Wuethrich, I., Blomen, V. A., Varadarajan, M., Sun, C., Bell, G., Yuan, B., Muellner, M. K., Nijman, S. M., et al. (2011). Global gene disruption in human cells to assign genes to phenotypes by deep sequencing. Nat Biotechnol 29, 542-546.

Chen, A., Hu, T., Mikoryak, C., and Draper, R. K. (2002). Retrograde transport of protein toxins under conditions of COPI dysfunction. Biochim Biophys Acta 1589, 124-139.

Cheung, H. W., Cowley, G. S., Weir, B. A., Boehm, J. S., Rusin, S., Scott, J. A., East, A., Ali, L. D., Lizotte, P. H., Wong, T. C., et al. (2011). Systematic investigation of genetic vulnerabilities across cancer cell lines reveals lineage specific dependencies in ovarian cancer. Proc Natl Acad Sci USA 108, 12372-12377.

Choi, C., Davey, M., Schluter, C., Pandher, P., Fang, Y., Foster, L. J., and Conibear, E. (2011). Organization and assembly of the TRAPPII complex. Traffic 12, 715-725.

Cleary, M. A., Kilian, K., Wang, Y., Bradshaw, J., Cavet, G., Ge, W., Kulkarni, A., Paddison, P. J., Chang, K., Sheth, N., et al. (2004). Production of complex nucleic acid libraries using highly parallel in situ oligonucleotide synthesis. Nat Methods 1, 241-248.

Collins, S. R., Weissman, J. S., and Krogan, N. J. (2009). From information to knowledge: new technologies for defining gene function. Nat Methods 6, 721-723.

Dixon, S. J., Costanzo, M., Baryshnikova, A., Andrews, B., and Boone, C. (2009). Systematic mapping of genetic interaction networks. Annu Rev Genet 43, 601-625.

Fellmann, C., Zuber, J., McJunkin, K., Chang, K., Malone, C. D., Dickins, R. A., Xu, Q., Hengartner, M. O., Elledge, S. J., Hannon, G. J., et al. (2011). Functional identification of optimized RNAi triggers using a massively parallel sensor assay. Mol Cell 41, 733-746.

Fromme, J. C., Orci, L., and Schekman, R. (2008). Coordination of COPII vesicle trafficking by Sec23. Trends in cell biology 18, 330-336.

Frost, A., Elgort, M. G., Brandman, O., Ives, C., Collins, S. R., Miller-Vedam, L., Weibezahn, J., Hein, M. Y., Poser, I., Mann, M., et al. (2012). Functional Repurposing Revealed by Comparing S. pombe and S. cerevisiae Genetic Interactions. Cell 149, 1339-1352.

Gavin, A. C., Bosche, M., Krause, R., Grandi, P., Marzioch, M., Bauer, A., Schultz, J., Rick, J. M., Michon, A. M., Cruciat, C. M., et al. (2002). Functional organization of the yeast proteome by systematic analysis of protein complexes. Nature 415, 141-147.

Geiger, R., Andritschke, D., Friebe, S., Herzog, F., Luisoni, S., Heger, T., and Helenius, A. (2011). BAP31 and BiP are essential for dislocation of SV40 from the endoplasmic reticulum to the cytosol. Nat Cell Biol 13, 1305-1314.

Girod, A., Storrie, B., Simpson, J. C., Johannes, L., Goud, B., Roberts, L. M., Lord, J. M., Nilsson, T., and Pepperkok, R. (1999). Evidence for a COP-I-independent transport route from the Golgi complex to the endoplasmic reticulum. Nat Cell Biol 1, 423-430.

Grimmer, S., Iversen, T. G., van Deurs, B., and Sandvig, K. (2000). Endosome to Golgi transport of ricin is regulated by cholesterol. Mol Biol Cell 11, 4205-4216.

Guimaraes, C. P., Carette, J. E., Varadarajan, M., Antos, J., Popp, M. W., Spooner, E., Brummelkamp, T. R., and Ploegh, H. L. (2011). Identification of host cell factors required for intoxication through use of modified cholera toxin. J Cell Biol 195, 751-764.

Horn, T., Sandmann, T., Fischer, B., Axelsson, E., Huber, W., and Boutros, M. (2011). Mapping of signaling networks through synthetic genetic interaction analysis by RNAi. Nat Methods 8, 341-346.

Johannes, L., and Popoff, V. (2008). Tracing the retrograde route in protein trafficking. Cell 135, 1175-1187.

Kaelin, W. G., Jr. (2012). Molecular biology. Use and abuse of RNAi to study mammalian gene function. Science 337, 421-422.

Kim, H. G., Ahn, J. W., Kurth, I., Ullmann, R., Kim, H. T., Kulharya, A., Ha, K. S., Itokawa, Y., Meliciani, I., Wenzel, W., et al. (2010). WDR11, a WD protein that interacts with transcription factor EMX1, is mutated in idiopathic hypogonadotropic hypogonadism and Kallmann syndrome. Am J Hum Genet 87, 465-479.

Landry, D. M., Hertz, M. I., and Thompson, S. R. (2009). RPS25 is essential for translation initiation by the Dicistroviridae and hepatitis C viral IRESs. Genes Dev 23, 2753-2764.

Llorente, A., Lauvrak, S. U., van Deurs, B., and Sandvig, K. (2003). Induction of direct endosome to endoplasmic reticulum transport in Chinese hamster ovary (CHO) cells (LdlF) with a temperature-sensitive defect in epsilon-coatomer protein (epsilon-COP). J Biol Chem 278, 35850-35855.

Lord, J. M., Roberts, L. M., and Lencer, W. I. (2005). Entry of protein toxins into mammalian cells by crossing the endoplasmic reticulum membrane: co-opting basic mechanisms of endoplasmic reticulum-associated degradation. Curr Top Microbiol Immunol 300, 149-168.

Luo, J., Emanuele, M. J., Li, D., Creighton, C. J., Schlabach, M. R., Westbrook, T. F., Wong, K. K., and Elledge, S. J. (2009). A genome-wide RNAi screen identifies multiple synthetic lethal interactions with the Ras oncogene. Cell 137, 835-848.

Marcotte, R., Brown, K. R., Suarez, F., Sayad, A., Karamboulas, K., Krzyzanowski, P. M., Sircoulomb, F., Medrano, M., Fedyshyn, Y., Koh, J. L., et al. (2012). Essential gene profiles in breast, pancreatic, and ovarian cancer cells. Cancer Discov 2, 172-189.

Merrill, M. K., and Gromeier, M. (2006). The double-stranded RNA binding protein 76:NF45 heterodimer inhibits translation initiation at the rhinovirus type 2 internal ribosome entry site. J Virol 80, 6936-6942.

Moffat, J., Grueneberg, D. A., Yang, X., Kim, S. Y., Kloepfer, A. M., Hinkle, G., Piqani, B., Eisenhaure, T. M., Luo, B., Grenier, J. K., et al. (2006). A lentiviral RNAi library for human and mouse genes applied to an arrayed viral high-content screen. Cell 124, 1283-1298.

Moreau, D., Kumar, P., Wang, S. C., Chaumet, A., Chew, S. Y., Chevalley, H., and Bard, F. (2011). Genome-wide RNAi screens identify genes required for Ricin and PE intoxications. Dev Cell 21, 231-244.

Paddison, P. J., Cleary, M., Silva, J. M., Chang, K., Sheth, N., Sachidanandam, R., and Hannon, G. J. (2004). Cloning of short hairpin RNAs for gene knockdown in mammalian cells. Nat Methods 1, 163-167.

Pawar, V., De, A., Briggs, L., Omar, M. M., Sweeney, S. T., Lord, J. M., Roberts, L. M., Spooner, R. A., and Moffat, K. G. (2011). RNAi screening of *Drosophila* (Sophophora) *melanogaster* S2 cells for ricin sensitivity and resistance. J Biomol Screen 16, 436-442.

Pierce, S. E., Davis, R. W., Nislow, C., and Giaever, G. (2007). Genome-wide analysis of barcoded *Saccharomyces cerevisiae* gene-deletion mutants in pooled cultures. Nat Protoc 2, 2958-2974.

Popoff, V., Adolf, F., Brugger, B., and Wieland, F. (2011). COPI budding within the Golgi stack. Cold Spring Harb Perspect Biol 3, a005231.

Ryan, C. J., Roguev, A., Patrick, K., Xu, J., Jahari, H., Tong, Z., Beltrao, P., Shales, M., Qu, H., Collins, S. R., et al. (2012). Hierarchical modularity and the evolution of genetic interactomes across species. Mol Cell 46, 691-704.

Sacher, M., Barrowman, J., Wang, W., Horecka, J., Zhang, Y., Pypaert, M., and Ferro-Novick, S. (2001). TRAPP I implicated in the specificity of tethering in ER-to-Golgi transport. Molecular cell 7, 433-442.

Sandvig, K., Torgersen, M. L., Engedal, N., Skotland, T., and Iversen, T. G. (2010). Protein toxins from plants and bacteria: probes for intracellular transport and tools in medicine. FEBS Lett 584, 2626-2634.

Schwarz, K., Iolascon, A., Verissimo, F., Trede, N. S., Horsley, W., Chen, W., Paw, B. H., Hopfner, K. P., Holzmann, K., Russo, R., et al. (2009). Mutations affecting the secretory COPII coat component SEC23B cause congenital dyserythropoietic anemia type II. Nature genetics 41, 936-940.

Scrivens, P. J., Noueihed, B., Shahrzad, N., Hul, S., Brunet, S., and Sacher, M. (2011). C4orf41 and TTC-15 are mammalian TRAPP components with a role at an early stage in ER-to-Golgi trafficking. Mol Biol Cell 22, 2083-2093.

Silva, J. M., Li, M. Z., Chang, K., Ge, W., Golding, M. C., Rickles, R. J., Siolas, D., Hu, G., Paddison, P. J., Schlabach, M. R., et al. (2005). Second-generation shRNA libraries covering the mouse and human genomes. Nat Genet 37, 1281-1288.

Silva, J. M., Marran, K., Parker, J. S., Silva, J., Golding, M., Schlabach, M. R., Elledge, S. J., Hannon, G. J., and Chang, K. (2008). Profiling essential genes in human mammary cells by multiplex RNAi screening. Science 319, 617-620.

Spooner, R. A., and Lord, J. M. (2012). How ricin and Shiga toxin reach the cytosol of target cells: retrotranslocation from the endoplasmic reticulum. Curr Top Microbiol Immunol 357, 19-40.

Storey, J. D., and Tibshirani, R. (2003). Statistical significance for genomewide studies. Proc Natl Acad Sci USA 100, 9440-9445.

Typas, A., Nichols, R. J., Siegele, D. A., Shales, M., Collins, S. R., Lim, B., Braberg, H., Yamamoto, N., Takeuchi, R., Wanner, B. L., et al. (2008). High-throughput, quantitative analyses of genetic interactions in *E. coli*. Nat Methods 5, 781-787.

Wu, H., Peisley, A., Graef, I. A., and Crabtree, G. R. (2007). NFAT signaling and the invention of vertebrates. Trends Cell Biol 17, 251-260.

Yamasaki, A., Menon, S., Yu, S., Barrowman, J., Meerloo, T., Oorschot, V., Klumperman, J., Satoh, A., and Ferro-Novick, S. (2009). mTrs130 is a component of a mammalian TRAPPII complex, a Rab1 GEF that binds to COPI-coated vesicles. Molecular biology of the cell 20, 4205-4215.

Zong, M., Wu, X. G., Chan, C. W., Choi, M. Y., Chan, H. C., Tanner, J. A., and Yu, S. (2011). The adaptor function of TRAPPC2 in mammalian TRAPPs explains TRAPPC2-associated SEDT and TRAPPC9-associated congenital intellectual disability. PLoS One 6, e23350.

Zuk, O., Hechter, E., Sunyaev, S. R., and Lander, E. S. (2012). The mystery of missing heritability: Genetic interactions create phantom heritability. Proc Natl Acad Sci USA 109, 1193-1198.

Bassik, M. C., Lebbink, R. J., Churchman, L. S., Ingolia, N. T., Patena, W., LeProust, E. M., Schuldiner, M., Weissman, J. S., and McManus, M. T. (2009). Rapid creation and quantitative monitoring of high coverage shRNA libraries. Nat Methods 6, 443-445.

Castro, C. P., Piscopo, D., Nakagawa, T., and Derynck, R. (2007). Cornichon regulates transport and secretion of TGFalpha-related p roteins in metazoan cells. J Cell Sci 120, 2454-2466.

Eisen, M. B., Spellman, P. T., Brown, P. O., and Botstein, D. (1998). Cluster analysis and display of genome-wide expression patterns. Proc Natl Acad Sci USA 95, 14863-14868.

Frost, A., Elgort, M. G., Brandman, O., Ives, C., Collins, S. R., Miller-Vedam, L., Weibezahn, J., Hein, M. Y., Poser, I., Mann, M., et al. (2012). Functional Repurposing Revealed by Comparing S. pombe and S. cerevisiae Genetic Interactions. Cell 149, 1339-1352.

Geiger, R., Andritschke, D., Friebe, S., Herzog, F., Luisoni, S., Heger, T., and Helenius, A. (2011). BAP31 and BiP are essential for dislocation of SV40 from the endoplasmic reticulum to the cytosol. Nat Cell Biol 13, 1305-1314.

Huang da, W., Sherman, B. T., and Lempicki, R. A. (2009a). Bioinformatics enrichment tools: paths toward the comprehensive functional analysis of large gene lists. Nucleic Acids Res 37, 1-13.

Huang da, W., Sherman, B. T., and Lempicki, R. A. (2009b). Systematic and integrative analysis of large gene lists u sing DAVID bioinformatics resources. Nat Protoc 4, 44-57.

Langmead, B., Trapnell, C., Pop, M., and Salzberg, S. L. (2009). Ultrafast and memory-efficient alignment of short DNA sequences to the human genome. Genome Biol 10, R25.

Linford, A., Yoshimura, S., Nunes Bastos, R., Langemeyer, L., Gerondopoulos, A., Rigden, D. J., and Barr, F. A. (2012). Rab14 and its exchange factor FAM116 link endocytic recycling and adherens junction stability in migrating cells. Developmental cell 22, 952-966.

Lozupone, F., Perdicchio, M., Brambilla, D., Borghi, M., Meschini, S., Barca, S., Marino, M. L., Logozzi, M., Federici, C., Iessi, E., et al. (2009). The human homologue of Dictyostelium discoideum phg1A is expressed by human metastatic melanoma cells. EMBO Rep 10, 1348-1354.

Luo, B., Cheung, H. W., Subramanian, A., Sharifnia, T., Okamoto, M., Yang, X., Hinkle, G., Boehm, J. S., Beroukhim, R., Weir, B. A., et al. (2008). Highly parallel identification of essential genes in cancer cells. Proc Natl Acad Sci USA 105, 20380-20385.

Matveeva, O. V., Kang, Y., Spiridonov, A. N., Saetrom, P., Nemtsov, V. A., Ogurtsov, A. Y., Nechipurenko, Y. D., and Shabalina, S. A. (2010). Optimization of duplex stability and terminal asymmetry for shRNA design. PLoS One 5, e10180.

Paddison, P. J., Cleary, M., Silva, J. M., Chang, K., Sheth, N., Sachidanandam, R., and Hannon, G. J. (2004). Cloning of short hairpin RNAs for gene knockdown in mammalian cells. Nat Methods 1, 163-167.

Poser, I., Sarov, M., Hutchins, J. R., Heriche, J. K., Toyoda, Y., Pozniakovsky, A., Weigl, D., N itzsche, A., Hegemann, B., Bird, A. W., et al. (2008). BAC TransgeneOmics: a high-throughput method for exploration of p rotein function in mammals. Nat Methods 5, 409-415.

Silva, J. M., Li, M. Z., Chang, K., Ge, W., Golding, M. C., Rickles, R. J., Siolas, D., Hu, G., Paddison, P. J., Schlabach, M. R., et al. (2005). Second-generation shRNA libraries covering the mouse and human genomes. Nat Genet 37, 1281-1288.

Sohaskey, M. L., Jiang, Y., Zhao, J. J., Mohr, A., Roemer, F., and Harland, R. M. (2010). Osteopotentia regulates osteoblast maturation, bone formation, and skeletal integrity in mice. J Cell Biol 189, 511-525.

Storey, J. D., and Tibshirani, R. (2003). Statistical significance for genomewide studies. Proc Natl Acad Sci USA 100, 9440-9445.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying a first and a second modulating nucleic acid element that target a first and a second genetic element, said method comprising:
   (a) cloning a first modulating nucleic acid element with a second modulating nucleic acid element to form a double-modulating viral vector comprising said first modulating nucleic acid element linked to said second modulating nucleic acid element, wherein said first modulating nucleic acid element targets a first genetic element and said second modulating nucleic acid element targets a second genetic element and wherein said first modulating nucleic acid element and said second modulating nucleic acid element are an interfering RNA, and further wherein said first genetic element is phenotypically responsive to said first modulating nucleic acid element and said second genetic element is phenotypically responsive to said second modulating nucleic acid element;
   (b) repeating step (a) using a plurality of different first modulating nucleic acid elements and a plurality of different second modulating nucleic acid elements, thereby forming a plurality of different double-modulating viral vectors;
   (c) infecting a plurality of mammalian cells with said plurality of different double-modulating viral vectors, thereby forming a plurality of double-modulating viral vector-infected mammalian cells;
   (d) separating a selected pool of said plurality of double-modulating viral vector-infected mammalian cells expressing a detectable phenotype from a non-selected pool of said plurality of double-modulating viral vector-infected mammalian cells not expressing said detectable phenotype;
   (e) quantitating the frequencies of said first modulating nucleic acid element linked to said second modulating nucleic acid element in said selected pool relative to the frequencies of said first modulating nucleic acid element linked to said second modulating nucleic acid element in said non-selected pool, thereby identifying a first and a second modulating nucleic acid element that target a first and a second genetic element;
   (f) cloning a first non-modulating nucleic acid element with a second non-modulating nucleic acid element to form a double non-modulating viral vector comprising said first non-modulating nucleic acid element linked to said second non-modulating nucleic acid element, wherein said first non-modulating nucleic acid element and said second modulating nucleic acid element do not target a genetic element and wherein said first non-modulating nucleic acid element and said second non-modulating nucleic acid element are an interfering RNA;

(g) repeating step (f) using a plurality of different first non-modulating nucleic acid elements and a plurality of different second non-modulating nucleic acid elements, thereby forming a plurality of different double non-modulating viral vectors;

(h) infecting a plurality of mammalian cells with said plurality of different double non-modulating viral vectors, thereby forming a plurality of double non-modulating viral vector-infected mammalian cells;

(i) separating a selected pool of said plurality of double non-modulating viral vector-infected mammalian cells expressing a detectable phenotype from a non-selected pool of said plurality of double non-modulating viral vector-infected mammalian cells not expressing said detectable phenotype; and (j) quantitating the frequencies of said first non-modulating nucleic acid element linked to said second non-modulating nucleic acid element in said selected pool relative to the frequencies of said first non-modulating nucleic acid element linked to said second non-modulating nucleic acid element in said non-selected pool.

2. The method of claim 1, further comprising:
detecting differences between said frequencies of said first modulating nucleic acid element linked to said second modulating nucleic acid element in said selected pool relative to a calculated control frequency and based at least in part on said differences detecting a genetic interaction between said first and second genetic elements.

3. The method of claim 2, wherein said genetic interaction corresponds to a buffering genetic interaction or a synergistic genetic interaction.

4. The method of claim 3, wherein the presence of a synergistic genetic interaction indicates that said first and second genetic elements act in parallel pathways.

5. The method of claim 3, wherein the presence of a buffering genetic interaction indicates that said first and second genetic elements act in a linear pathway.

6. The method of claim 5, further comprising screening said double-modulating viral vector for different phenotypes and/or in different cell lines.

7. The method of claim 6, wherein said double-modulating viral vector comprises a unique barcode for each of said first and second modulating nucleic acid elements.

8. The method of claim 7, wherein step (j) comprises quantitating the frequencies of said first and second modulating nucleic acid elements by deep sequencing.

9. A method for identifying a first and a second modulating nucleic acid element that target a first and a second genetic element, said method comprising:

(a) cloning a first modulating nucleic acid element with a second modulating nucleic acid element to form a double-modulating viral vector comprising said first modulating nucleic acid element linked to said second modulating nucleic acid element, wherein said first modulating nucleic acid element targets a first genetic element and said second modulating nucleic acid element targets a second genetic element and wherein said first modulating nucleic acid element and said second modulating nucleic acid element are an interfering RNA, and further wherein said first genetic element is phenotypically responsive to said first modulating nucleic acid element and said second genetic element is phenotypically responsive to said second modulating nucleic acid element;

(b) repeating step (a) using a plurality of different first modulating nucleic acid elements and a plurality of different second modulating nucleic acid elements, thereby forming a plurality of different double-modulating viral vectors;

(c) infecting a plurality of mammalian cells with said plurality of different double-modulating viral vectors, thereby forming a plurality of double-modulating viral vector-infected mammalian cells;

(d) separating a selected pool of said plurality of double-modulating viral vector-infected mammalian cells expressing a detectable phenotype from a non-selected pool of said plurality of double-modulating viral vector-infected mammalian cells not expressing said detectable phenotype;

(e) quantitating the frequencies of said first modulating nucleic acid element linked to said second modulating nucleic acid element in said selected pool relative to the frequencies of said first modulating nucleic acid element linked to said second modulating nucleic acid element in said non-selected pool, thereby identifying a first and a second modulating nucleic acid element that target a first and a second genetic element;

(f) cloning said first or second modulating nucleic acid element with a first non-modulating nucleic acid element to form a mixed-modulating/non-modulating viral vector comprising said first or second modulating nucleic acid element linked to said first non-modulating nucleic acid element, wherein said first non-modulating nucleic acid element does not target a genetic element and wherein said first non-modulating nucleic acid element is an interfering RNA;

(g) repeating step (f) using a plurality of different first or second modulating nucleic acid elements and a plurality of different first non-modulating nucleic acid elements, thereby forming a plurality of different mixed-modulating/non-modulating viral vectors;

(h) infecting a plurality of mammalian cells with said plurality of different mixed-modulating/non-modulating viral vectors, thereby forming a plurality of mixed-modulating/non-modulating viral vector-infected mammalian cells;

(i) separating a selected pool of said plurality of mixed-modulating/non-modulating viral vector-infected mammalian cells expressing a detectable phenotype from a non-selected pool of said mixed-modulating/non-modulating viral vector-infected mammalian cells not expressing said detectable phenotype; and (j) quantitating the frequencies of said first or second modulating nucleic acid element linked to said first non-modulating nucleic acid element in said selected pool relative to the frequencies of said first or second modulating nucleic acid element linked to said first non-modulating nucleic acid element in said non-selected pool.

10. A method for identifying a first and a second modulating nucleic acid element that target a first and a second genetic element, said method comprising:

(a) providing a plurality of modulating nucleic acid elements comprising two or more modulating nucleic acid elements that each target a first genetic element, two or more modulating nucleic acid elements that each target a second genetic element; and further providing one or a plurality of non-modulating nucleic acid elements, wherein said plurality of modulating nucleic acid elements are interfering RNA and wherein said one or said plurality of non-modulating nucleic acid elements is/are an interfering RNA;

(b) cloning a first modulating nucleic acid element that targets the first genetic element with a second modulating nucleic acid element that targets the second genetic element to form a double-modulating viral vector comprising said first modulating nucleic acid element linked to said second modulating nucleic acid element, wherein said first genetic element is phenotypically responsive to said first modulating nucleic acid element and said second genetic element is phenotypically responsive to said second modulating nucleic acid element;

(c) repeating step (b) to clone all of the pairwise combinations of (1) the two or more modulating nucleic acid elements that each target a first genetic element with the two or more modulating nucleic acid elements that each target a second genetic element to form a plurality of different double-modulating viral vectors, and (2) the one or a plurality of non-modulating nucleic acid elements with (i) at least one of the two or more modulating nucleic acid elements that each target the first genetic element or (ii) at least one of the two or more modulating nucleic acid elements that each target the second genetic element, to form a plurality of different mixed-modulating/non-modulating viral vectors; thereby forming a plurality of viral vectors containing all pairwise combinations of said modulating and non-modulating nucleic acid elements;

(d) infecting a plurality of mammalian cells with said plurality of different double-modulating viral vectors and/or said plurality of different mixed-modulating/non-modulating viral vectors, thereby forming a plurality of double-modulating viral vector-infected mammalian cells and a plurality of mixed-modulating/non-modulating viral vector-infected mammalian cells;

(e) separating a selected pool of said plurality of double-modulating viral vector-infected mammalian cells expressing a detectable phenotype from a non-selected pool of said plurality of double-modulating viral vector-infected mammalian cells not expressing said detectable phenotype;

(f) quantitating the frequencies of said first modulating nucleic acid element linked to said second modulating nucleic acid element in said selected pool relative to the frequencies of said first modulating nucleic acid element linked to said second modulating nucleic acid element in said non-selected pool, thereby identifying a first and a second modulating nucleic acid element that target a first and a second genetic element;

(g) separating a selected pool of said plurality of mixed-modulating/non-modulating viral vector-infected mammalian cells expressing a detectable phenotype from a non-selected pool of said mixed-modulating/non-modulating viral vector-infected mammalian cells not expressing said detectable phenotype; and (h) quantitating the frequencies of said first or second modulating nucleic acid element linked to said first non-modulating nucleic acid element in said selected pool relative to the frequencies of said first or second modulating nucleic acid element linked to said first non-modulating nucleic acid element in said non-selected pool.

* * * * *